US008337905B2

(12) United States Patent
Dicosimo et al.

(10) Patent No.: US 8,337,905 B2
(45) Date of Patent: Dec. 25, 2012

(54) MULTI-COMPONENT PERACID GENERATION SYSTEM

(75) Inventors: Robert Dicosimo, Chadds Ford, PA (US); Arie Ben-Bassat, Wilmington, DE (US); William R. Cahill, Hockessin, DE (US); David George Dipietro, Mullica Hill, NJ (US); Eugenia Costa Hann, Carneys Point, NJ (US); Mark S. Payne, Wilmington, DE (US); Richard Alan Reynolds, Middletown, DE (US); Raymond Richard Zolandz, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 451 days.

(21) Appl. No.: 12/572,107

(22) Filed: Oct. 1, 2009

(65) Prior Publication Data
US 2010/0086621 A1    Apr. 8, 2010

Related U.S. Application Data

(60) Provisional application No. 61/102,505, filed on Oct. 3, 2008, provisional application No. 61/102,512, filed on Oct. 3, 2008, provisional application No. 61/102,514, filed on Oct. 3, 2008, provisional application No. 61/102,520, filed on Oct. 3, 2008, provisional application No. 61/102,531, filed on Oct. 3, 2008, provisional application No. 61/102,539, filed on Oct. 3, 2008.

(51) Int. Cl.
| A01N 39/00 | (2006.01) |
| C12P 7/40 | (2006.01) |
| C12N 9/00 | (2006.01) |
| D06L 1/02 | (2006.01) |
| C11D 7/18 | (2006.01) |
| C07H 21/04 | (2006.01) |

(52) U.S. Cl. ........ 424/616; 435/136; 435/183; 510/281; 510/305; 536/23.2

(58) Field of Classification Search .......... None
See application file for complete search history.

(56) References Cited

U.S. PATENT DOCUMENTS

| 3,974,082 A | 8/1976 | Weyn |
| 4,444,886 A | 4/1984 | Esders et al. |
| 4,585,150 A | 4/1986 | Beacham et al. |
| 4,678,103 A | 7/1987 | Dirksing |
| 5,116,575 A | 5/1992 | Badertscher et al. |
| 5,152,461 A | 10/1992 | Proctor |
| 5,281,525 A | 1/1994 | Mitsushima et al. |
| 5,296,161 A | 3/1994 | Wiersema et al. |
| 5,338,676 A | 8/1994 | Mitsushima et al. |
| 5,364,554 A | 11/1994 | Stanislowski et al. |
| 5,398,846 A | 3/1995 | Corba et al. |
| 5,528,152 A | 6/1996 | Hinoshita et al. |
| 5,532,157 A | 7/1996 | Fink |
| 5,605,793 A | 2/1997 | Stemmer |
| 5,624,634 A | 4/1997 | Brougham et al. |
| 5,683,724 A | 11/1997 | Hei et al. |
| 5,811,238 A | 9/1998 | Stemmer et al. |
| 5,830,721 A | 11/1998 | Stemmer et al. |
| 5,837,458 A | 11/1998 | Minshull et al. |
| 5,862,949 A | 1/1999 | Markey et al. |
| 5,932,532 A | 8/1999 | Ghosh et al. |
| 5,954,213 A | 9/1999 | Gerhart et al. |
| 6,183,807 B1 | 2/2001 | Gutzmann et al. |
| 6,210,639 B1 | 4/2001 | Vlass et al. |
| 6,223,942 B1 | 5/2001 | Markey et al. |
| 6,319,888 B2 | 11/2001 | Wei et al. |
| 6,391,840 B1 | 5/2002 | Thompson et al. |
| 6,465,233 B1 | 10/2002 | Knauseder et al. |
| 6,518,307 B2 | 2/2003 | McKenzie et al. |
| 6,545,047 B2 | 4/2003 | Gutzmann et al. |
| 6,635,286 B2 | 10/2003 | Hei et al. |
| 6,645,233 B1 | 11/2003 | Ayers et al. |
| 6,758,411 B2 | 7/2004 | Conway et al. |
| 6,995,125 B2 | 2/2006 | Dasque et al. |
| 7,448,556 B2 | 11/2008 | Muehlhausen et al. |
| 2002/0030063 A1 | 3/2002 | Leray et al. |
| 2004/0127381 A1 | 7/2004 | Scialla et al. |
| 2005/0008526 A1 | 1/2005 | Bianchetti et al. |
| 2008/0176299 A1 | 7/2008 | Dicosimo et al. |
| 2008/0176783 A1 | 7/2008 | DiCosimo et al. |
| 2009/0005590 A1 | 1/2009 | DiCosimo et al. |

FOREIGN PATENT DOCUMENTS

| EP | 0807156 B1 | 11/1997 |
| WO | WO96/32149 | 10/1996 |
| WO | WO97/41833 | 11/1997 |
| WO | WO99/03984 | 1/1999 |
| WO | WO00/61713 | 10/2000 |
| WO | WO02/22467 | 3/2002 |
| WO | WO2005/035705 A2 | 4/2005 |
| WO | WO2007/070609 A2 | 6/2007 |
| WO | WO2007/106293 A1 | 9/2007 |
| WO | WO2008/073139 A1 | 6/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Witkowski et al. Biochemistry. Sep. 7, 1999; 38(36): 11643-50.*
Copending U.S. Appl. No. 12/572,086, filed Oct. 1, 2009.
Belghitih, Stabilization of Penicillium Occitanis Cellulases by Sray Drying in Presence . . . , Enzyme and Microbial Tech., 28 (2001) 253-258, XP-002558791.
Justus Liebigs Annalen der Chemie; 105:206 (1858).
Wurtz, Annales de Chimie; 55:443 (1859).
Seelig, Univ. of Berlin Laboratory; 24: 3466 (1891).
Stöchiometrie und Verwandtschaftslehre vol. 183, [K. Loskit, On the Knowledge of Triglycerides, pp. 135-155], vol. 134, Nos. 1 and 2, May 1928.

(Continued)

Primary Examiner — Christian Fronda

(57) ABSTRACT

Disclosed herein are multi-component peroxycarboxylic acid generation systems for enzymatically producing aqueous formulations of peroxycarboxylic acids suitable for use in, e.g., disinfectant and/or bleaching applications. The multi-component peroxycarboxylic acid generation systems comprise at least one carbohydrate esterase family 7 enzyme having perhydrolytic activity.

11 Claims, 4 Drawing Sheets

OTHER PUBLICATIONS

Abbot et al., Physical Properties and Kinetic Behavior of a Cephalosporin . . . , Appl. Microbiol. 30(3):413-419 (1975).
Funasaki, N. et al., Intramolecular Hydrophobic Association of Two Alkyl Chains of Oligoethylene Glycol Diethers and Diesters in Water, J. Phys. Chem. 88:5786-5790 (1984).
C. Laane et al., Rules for Optimization of Biocatalysis in Organic Solvents, Biotechnol. Bioeng. 30:81-87 (1987).
Cowan et al., Biocatalysis in Organic Phase Media., Ch. 7 in Biocatalysis at Extreme Temperatures . . . , Amer. Chem. Soc. Symposium Series 498, pp. 86-107 (1992).
Lee, Y.E. et al., Genetic Organization, Sequence and Biochemical Characterization of Recombinant . . . , J Gen Microbiol. (1993), 139:1235-1243.
Mitsushima et al Gene Cloning, Nucleotide Sequence, and Expression . . . , Appl. Env. Microbiol. 61(6):2224-2229, (1995).
Fromant et al., Direct Random Mutagenesis of Gene-Sized DNA Fragments Using Polymerase Chain Reaction, Analytical Biochemistry 224, 347-353 (1995).
Kobayashi et al., Purification and Properties of an Alkaline Protease from Alkalophilic *Bacillus* sp. KSM-K16, Appl. Microbiol. Biotechnol. 43 (3), 473-481 (1995).
Kuo, S-J. et al., Solvent Polarity Influences Product Selectivity of Lipase-Mediated Esterification Reactions in Microaqueous Media, J. Am. Oil Chem. Soc. 73:1427-1433 (1996).
Pinkernell, U. et al., Simultaneous HPLC Determination of Peroxyacetic Acid and Hydrogen Peroxide, Anal. Chem., 69(17):3623-3627 (1997).
Kunst et al., The Complete Genome Sequence of the Gram-Positive Bacterium *Bacillus subtilis*, Nature 390:249-256 (1997).
Lin-Goerke et al., PCR-based Random Mutagenesis Using Manganese and Reduced dNTP Concentration, Biotechniques, 23(3):409-12 (1997).
Nixon et al., Assembly of an Active Enzyme by the Linkage of Two Protein Modules, PNAS, 94:1069-1073 (1997).
Lorenz et al., Isolation, Analysis and Expresion of Two Genes from Thermoanaerobacterium . . . , J. Bacteriol 179:5436-5441 (1997).
Politino et al., Purification and Characterization of a Cephalosporin Esterase . . . , Appl. Environ. Microbiol., 63(12):4807-4811 (1997).
Sakai et al., Purification and Properties of Cephalosporing-C Deacetylase from the Yeast . . . , J. Ferment. Bioeng. 85:53-57 (1998).
Gilbert et al. Recent Advances in Carbohydrate Bioengineering, The Royal Society of Chemistry, Cambridge, pp. 3-12. (1999).
Nelson et al., Evidence for Lateral Gene Transfer Between Archaea and Bacteria From Genome Sequence of *Thermotoga maritime*, Nature, 399:323-329 (1999).
Melnikov et al., Random Mutagenesis by Recombinational Capture of PCR Products in *Bacillus subtilis* and *Acinetobacter calcoaceticus*, Nucleic Acids Res. 27(4):1056-62 (1999).
Cardoza et al., A Cephalosporin C Acetylhydrolase is Present in the Cultures of *Nocardia lactamdurans*, Appl. Microbiol. Biotechnol., 54(3):406-412 (2000).
Berman, H.M. et al., The Protein Data Bank. Nucleic Acids Research, 28 pp. 235-242 (2000).

Degrassi et al., The Acetyl Xyland Esterase of *Bacillus pumilus* Belongs to a Family . . . , Microbiology., 146:1585-1591 (2000).
Takami et al., Complete Genome Sequences of the Alkaliphilic Bacterium *Bacillus halodurans* and . . . , NAR, 28(21):4317-4331 (2000).
Gunning, Y. M. et al., Phase Behavior and Component Partitioning in Low Water Content Amorphous Carbohydrates . . . , J. Agric. Food Chem. 48:395-399 (2000).
Vincent et al., Multifunctional Xylooligosaccharide/Cephalosporin C Deacetylase . . . , J. Mol. Biol., 330:593-606 (2003).
Ru et al, On the Salt-Induced Activation of Lyophilized Enzyme in Organic Solvents, J. Am. Chem. Soc. vol. 122, No. 8, pp. 1465-1571, Feb. 9, 2000.
Ikeda et al., Complete Genome Sequence and Comparative Analysis of the Industrial Microorganism *Streptomyces avermitilis*, Nat. Biotechnol. 21 (5), 526-531 (2003).
H.M. Berman, Announcing the Worldwide Protein Data Bank, Nature Structural Biology 10 (12), p. 980 (2003).
Rey et al., Complete Genome Sequence of the Industrial Bacterium *Bacillus licheniformis* and . . . , Genome Biol., 5(10): article 77, R77.1-R77-12, (2004).
Braeken, L. et al., Modeling of the Adsorption of Organic Compounds on Polymeric Nanofiltration Membranes in Solutions Containing . . . , Chem Phys Chem, 6:1606-1612 (2005).
Castillo et al., On the Activity Loss of Hydrolases in Organic Solvents . . . , J. Mol. Catalysis Elsevier, vol. 35, No. 4-6, pp. 147-153, Sep. 1, 2005.
Krastanova et al., Heterologous Expression, Purificaiton, Crystallization, X-Ray Analysis and . . . , Biochimica ET Biophysica Acta, vol. 1748, No. 2, May 2005, pp. 222-230.
Serdakowski et al., Enzyme Activation for Organic Solvents Made Easy, Treads in Biotechnology, Trends in Biotechnology, Review, vol. 26, No. 1, pp. 48-54, Nov. 26, 2007.
Siezen et al., Genome-Scale Genotype-Phenotype Matching of Two *Lactococcus lactis* Isolates from Plants Identifies . . . , Appl. Environ. Microbiol. (2008) 74(2): 424-436).
Yoshii et al., Effects of protein on Retention of ADH enzyme Activity Encapsulated . . . , Journal of Food Engr., vol. 87, No. 1, pp. 34-39, Feb. 23, 2008.
Dicosimo, Thermophilic Perhydrolases for Peracetic Acid Production, Sim Annual Meeting and Exhibition, XP0002557717, Jul. 30, 2009.
Copending U.S. Appl. No. 11/638,635, filed Dec. 12, 2006.
Copending U.S. Appl. No. 12/143,375, filed Jun. 20, 2008.
Copending U.S. Appl. No. 12/539,025, filed Aug. 11, 2009.
Copending U.S. Appl. No. 12/571,702, filed Oct. 1, 2009.
Copending U.S. Appl. No. 12/572,059, filed Oct. 1, 2009.
Copending U.S. Appl. No. 12/572,070, filed Oct. 1, 2009.
Copending U.S. Appl. No. 12/572,094, filed Oct. 1, 2009.
Copending U.S. Appl. No. 12/572,115, filed Oct. 1, 2009.
Corresponding International Search Report and Written Opinion (PCT/US2009/059227) dated Dec. 16, 2009.

* cited by examiner

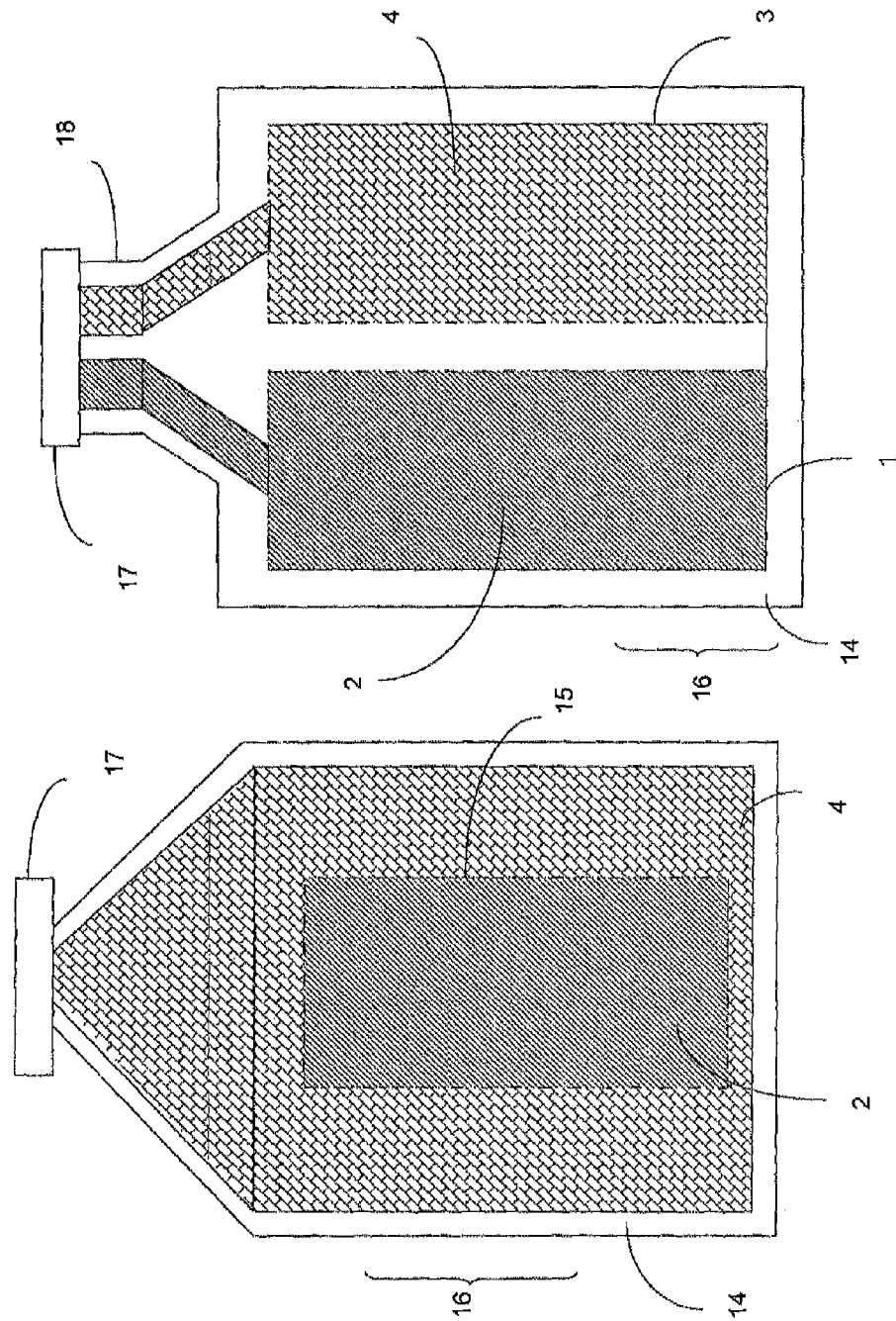

MULTI-COMPONENT PERACID GENERATION SYSTEM

CROSS-REFERENCE TO RELATED APPLICATIONS

This application claims the benefit of U.S. Provisional Patent Application Nos. 61/102,505; 61/102,512; 61/102,514; 61/102,520; 61/102,531; and 61/102,539; each filed Oct. 3, 2008, each of which incorporated by reference herein in their entireties.

FIELD OF THE INVENTION

This invention relates to the field of enzymatic peroxycarboxylic acid synthesis and in situ enzyme catalysis. Specifically, a multi-component peroxycarboxylic acid generation system is provided for enzymatically producing aqueous solutions of peroxycarboxylic acids upon mixing the components from a first compartment with the components of a second compartment. At least one peroxycarboxylic acid is produced at sufficient concentrations as to be efficacious for the disinfection or sanitization of surfaces, medical instrument sterilization, food processing equipment sterilization, and suitable for use in laundry care applications such as bleaching, destaining, deodorizing, and sterilization.

BACKGROUND OF THE INVENTION

Peroxycarboxylic acid compositions have been reported to be effective antimicrobial agents. Methods to clean, disinfect, and/or sanitize hard surfaces, meat products, living plant tissues, and medical devices against undesirable microbial growth have been described (e.g., U.S. Pat. Nos. 6,545,047; 6,183,807; 6,518,307; 5,683,724; and U.S. Patent Application Publication No. 2003/0026846). Peroxycarboxylic acids have also been reported to be useful in preparing bleaching compositions for laundry detergent applications (e.g., U.S. Pat. Nos. 3,974,082; 5,296,161; and 5,364,554).

Peroxycarboxylic acids can be prepared by the chemical reaction of a carboxylic acid and hydrogen peroxide (see *Organic Peroxides*, Daniel Swern, ed., Vol. 1, pp 313-516; Wiley Interscience, New York, 1971). The reaction is usually catalyzed by a strong inorganic acid, such as concentrated sulfuric acid. The reaction of hydrogen peroxide with a carboxylic acid is an equilibrium reaction, and the production of peroxycarboxylic acid is favored by the use of an excess concentration of peroxide and/or carboxylic acid, or by the removal of water.

Some peroxycarboxylic acid-based disinfectants or bleaching agents are comprised of an equilibrium mixture of peroxycarboxylic acid, hydrogen peroxide, and the corresponding carboxylic acid. One disadvantage of these commercial peroxycarboxylic acid cleaning systems is that the peroxycarboxylic acid is oftentimes unstable in solution over time. One way to overcome the stability problem is to generate the peroxycarboxylic acid prior to use by combining multiple reaction components that are individually stable for extended periods of time. Preferably, the individual reaction components are easy to store, relatively safe to handle, and capable of quickly producing an efficacious concentration of peroxycarboxylic acid upon mixing.

One way to overcome the disadvantages of chemical peroxycarboxylic acid production is to use an enzyme catalyst having perhydrolysis activity. U.S. patent application Ser. No. 11/638,635 and U.S. Patent Application Publication Nos. 2008/0176783, 2008/0176299, and 2009/0005590 to DiCosimo et al. disclose enzymes structurally classified as members of the CE-7 family of carbohydrate esterases cephalosporin C deacetylases [CAHs] and acetyl xylan esterases [AXEs]) that are characterized by significant perhydrolysis activity for converting carboxylic acid esters (in the presence of a suitable source of peroxygen, such as hydrogen peroxide) into peroxycarboxylic acids at concentrations sufficient for use as a disinfectant and/or a bleaching agent. Some members of the CE-7 family of carbohydrate esterases have been demonstrated to have perhydrolytic activity sufficient to produce 4000-5000 ppm peracetic acid from acetyl esters of alcohols, diols, and glycerols in 1 minute and up to 9000 ppm between 5 minutes and 30 minutes once the reaction components were mixed (DiCosimo et al., U.S. 2009/0005590).

Enzymatic peroxycarboxylic acid generation systems may be based on a two-component system, where each component is stored in a separate compartment until use. Typically, the enzyme catalyst having perhydrolysis activity is stored in one compartment with the carboxylic acid ester substrate and the source of peroxygen (typically an aqueous solution of hydrogen peroxide) is stored in a second compartment. The components of the two compartments are mixed to produce the desired aqueous solution of peroxycarboxylic acid.

However, multi-component enzymatic peracid generation systems may also suffer from certain problems. One problem may be the use of one or more carboxylic acid ester substrates that are insoluble or partially insoluble in water after mixing of the two components. The limited solubility of certain carboxylic acid ester substrates can result in at least three conditions that interfere with the ability to efficaciously produce and deliver a peroxycarboxylic acid product: first, the viscosity of the enzyme catalyst/substrate constituent can be too high to permit efficient mixing with a second constituent comprising a source of peroxygen, which decreases the rate of production of peroxycarboxylic acid; second, the viscosity of the enzyme catalyst/substrate constituent can be too high to permit certain modes of delivery of a product comprising a mixture of the enzyme catalyst/substrate constituent and the source of peroxygen, such as spraying; third, the dissolution rate of the substrate in the enzyme/substrate component after mixing with a second component comprising a source of peroxygen in aqueous solution is too low to permit a satisfactory rate of production of peroxycarboxylic acid. The carboxylic acid ester solubility problems also become evident in situations where use of a particular ratio of a component comprising an aqueous source of peroxygen to a component comprising an enzyme catalyst/substrate constituent is desired. As such, commercial uses of multi-component systems that involve the storage of the enzyme catalyst having perhydrolysis activity and substrate separately from a source of peroxygen until a desired time of reaction have remained impracticable for some applications.

The use of organic cosolvents to enhance mixing and/or alter the viscosity of the carboxylic acid ester in water may be problematic. Organic solvents can be deleterious to the activity of enzymes, either when enzymes are suspended directly in organic solvents, or when miscible organic/aqueous single phase solvents are employed. Two literature publications that review the effects of organic solvents on enzyme activity and structure are: (a) C. Laane et al., *Biotechnol. Bioeng.* 30:81-87 (1987) and (b) Cowan, D. A. and Plant, A., *Biocatalysis in Organic Phase Systems.*, Ch. 7 in *Biocatalysis at Extreme Temperatures*, Kelly, R. W. W. and Adams, M., eds., Amer. Chem. Soc. Symposium Series, Oxford University Press, New York, N.Y., pp 86-107 (1992). Cowan and Plant note (on page 87) that there is little or no value in using organic solvents having a log $P \leq 2$ to stabilize intracellular enzymes in an organic phase system. Organic solvents having a log P between two and four can be used on a case-by-case basis dependent on enzyme stability, and those having a log P>4 are generally useful in organic phase systems.

Cowan and Plant, supra, further note (on page 91) that the effect of direct exposure of an enzyme dissolved in a single-phase organic-aqueous solvent depends on solvent concentration, solvent/enzyme surface group interactions, and solvent/enzyme hydration shell interactions. Because a solvent's log P value must be sufficiently low so that the solvent is fully miscible with the aqueous phase to produce a single-phase, a single-phase organic-aqueous solvent containing a low log P organic solvent usually has a negative effect on enzyme stability except in low organic solvent concentration applications.

The storage stability of a CE-7 enzyme having perhydrolysis activity is a concern when stored in a carboxylic acid ester substrate or a mixture of the carboxylic acid ester and one or more cosolvents having a partition coefficient (as measured by a log P value, i.e., the logarithm of the partition coefficient of a substance between octanol and water, where P equals $[\text{solute}]_{octanol}/[\text{solute}]_{water}$) of two or less. Several of the organic ester substrates described by DiCosimo et al., in U.S. 2009/0005590 have log P values of less than two. For example, triacetin is reported to have a log P of 0.25 (Y. M. Gunning, et al., *J. Agric. Food Chem.* 48:395-399 (2000)), similar to that of ethanol (log P −0.26) and isopropanol (log P 0.15) (Cowan and Plant); therefore the storage of enzyme powder in triacetin would be expected to result in unacceptable loss of enzyme activity, as would the use of additional cosolvents with log P<2 (e.g., cyclohexanone, log P=0.94) (Cowan and Plant); 1,2-propanediol, log P=−1.41 (Gunning, et al.); 1,3-propanediol, log P=−1.3 (S-J. Kuo, et al., *J. Am. Oil Chem. Soc.* 73:1427-1433 (1996); diethylene glycol butyl ether, log P=0.56 (N. Funasaki, at al., *J. Phys. Chem.* 88:5786-5790 (1984); triethyleneglycol, log P=−1.75 (L. Braeken, et al., *ChemPhysChem* 6:1606-1612 (2005)).

Co-owned, co-filed, and copending U.S. patent application under attorney docket number CL4205 US NA entitled "ENZYMATIC PERACID PRODUCTION USING A COSOLVENT" describes the use of organic co-solvents having a log P value of about 2 or less to control the viscosity of a substrate-containing component and to enhance the solubility of the substrate in an aqueous reaction mixture without causing substantial loss of perhydrolytic activity of the enzyme catalyst.

Co-owned, co-filed, and copending U.S. patent applications under attorney docket numbers CL4386 US NA and CL4387 US NA, each having the title "STABILIZATION OF PERHYDROLASES", describe various ways to stabilize enzymatic perhydrolysis activity of enzyme powders when present in the carboxylic acid ester substrate component of a multi-component peroxycarboxylic acid generation system.

Co-owned, co-filed, and copending U.S. patent application under attorney docket number CL4392 US NA entitled "IMPROVED PERHYDROLASES FOR ENZYMATIC PERACID GENERATION" describes variant CE-7 enzymes having improved perhydrolytic activity.

The problem to be solved is to provide multi-component peroxycarboxylic acid generation systems comprising a combination of ingredients characterized by enhanced storage stability of the CE-7 catalyst's perhydrolytic activity and/or improved mixing and/or viscosity characteristics of the carboxylic acid ester substrate-containing component. In a further embodiment, the multi-component peroxycarboxylic acid generation system preferably comprises a variant CE-7 enzyme having improved perhydrolytic activity.

SUMMARY OF THE INVENTION

The stated problem has been solved by providing a multi-component peroxycarboxylic acid generating system comprising a first compartment and a second compartment, wherein the components in the respective compartments provide enhanced storage stability and/or improved mixing characteristics.

In one embodiment, a multi-component peroxycarboxylic acid generation system is provided comprising: a first compartment comprising a first component and a second compartment comprising a second component and means for mixing the first component and the second component to produce an aqueous solution of peracetic acid; wherein the first component comprises (i) an enzyme powder comprising a formulation of:
  (a) at least one enzyme catalyst having perhydrolysis activity, wherein said enzyme catalyst comprises an enzyme having a carbohydrate esterase family 7 (CE-7) signature motif that aligns with SEQ ID NO: 1 using CLUSTALW, said signature motif comprising:
    (1) an RGQ motif at amino acid positions aligning with 118-120 of SEQ ID NO:1;
    (2) a GXSQG motif at amino acid positions aligning with 179-183 of SEQ ID NO:1; and
    (3) an HE motif at amino acid positions aligning with 298-299 of SEQ ID NO:1;
    said enzyme comprising at least 30% amino acid identity to SEQ ID NO: 1; and
  (b) at least one excipient;
(ii) a carboxylic acid ester substrate selected from the group consisting of
  (a) one or more esters having the structure $[X]_m R_5$ wherein
    X is an ester group of the formula $R_6C(O)O$;
    $R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
    $R_5$ is a C1 to C6 linear, branched, or cyclic hydrocarbyl moiety optionally substituted with a hydroxyl group,
    wherein each carbon atom in $R_5$ individually comprises no more than one hydroxyl group or no more than one ester group, and wherein $R_5$ optionally comprises one or more ether linkages;
    m is 1 to the number of carbon atoms in $R_5$,
    said one or more esters having solubility in water of at least 5 ppm at 25° C.;
  (b) one or more glycerides having the structure

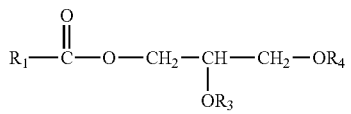

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;

(c) one or more esters of the formula

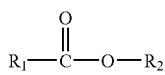

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10;

(d) one or more acetylated monosaccharides, acetylated disaccharides, or acetylated polysaccharides; and (e) any combination of (a) through (d);

wherein the amount of the carboxylic acid ester substrate in the first component is designed to provide a final concentration of 0.5 wt % to 10 wt % in a reaction formulation formed by combining the first and second components;

(iii) a buffer selected from the group consisting of bicarbonate, citrate, acetate, phosphate, pyrophosphate, methylphosphonate, succinate, malate, fumarate, tartrate, and maleate;

(iv) a cosolvent selected from the group consisting of tripropylene glycol methyl ether, dipropylene glycol methyl ether, propylene glycol methyl ether, diethylene glycol butyl ether, dipropylene glycol, triethylene glycol, 1,2-propanediol, N-ethyl-2-pyrroldinone, isopropanol, ethanol, ethyl lactate, 1,3-propanediol, and any combination thereof; and (v) optionally at least one surfactant;

wherein the second component comprises water, hydrogen peroxide and a hydrogen peroxide stabilizer.

In another aspect, a multi-component peroxycarboxylic acid generation system is provided comprising a first compartment comprising a first component and a second compartment comprising a second component and means for mixing the first and second component to produce an aqueous solution of peracetic acid wherein the first component comprises (i) an enzyme powder comprising a formulation of
    (a) at least one CE-7 enzyme having perhydrolysis activity, wherein said at least one CE-7 enzyme comprises an amino acid sequence selected from the group consisting of SEQ ID NO: 6, SEQ ID NO: 7, SEQ ID NO: 19 and SEQ ID NO: 20 or an amino acid sequence substantially similar to SEQ ID NO: 6, SEQ ID NO: 7, SEQ ID NO: 19 or SEQ ID NO: 20; and
    (b) at least one excipient;

(ii) a carboxylic acid ester substrate selected from the group consisting of monoacetin, diacetin, triacetin, and a mixtures thereof; wherein the amount of the carboxylic acid ester substrate in the first component is designed to provide a final concentration of 0.5 wt % to 10 wt % in a reaction formulation formed by combining the first and second components;

(iii) a buffer selected from the group consisting of bicarbonate, citrate, acetate, phosphate, pyrophosphate, methylphosphonate, succinate, malate, fumarate, tartrate, and maleate;

(iv) a cosolvent selected from the group consisting of tripropylene glycol methyl ether, dipropylene glycol methyl ether, propylene glycol methyl ether, diethylene glycol butyl ether, dipropylene glycol, triethylene glycol, 1,2-propanediol, N-ethyl-2-pyrroldinone, isopropanol, ethanol, ethyl lactate, 1,3-propanediol, and any combination thereof; and (v) optionally at least one surfactant;

wherein the second component comprises water, hydrogen peroxide and a hydrogen peroxide stabilizer.

In another aspect, the multi-component peroxycarboxylic acid generation system above is provided wherein:

(i) the at least one CE-7 enzyme comprises an amino acid sequence selected from the group consisting of SEQ ID NO: 6, SEQ ID NO: 7, SEQ ID NO: 19 and SEQ ID NO: 20, wherein amino acid residue 277 of SEQ ID NO: 19 or SEQ ID NO: 20 is selected from the group consisting of alanine, valine, serine, and threonine;

(ii) the carboxylic acid ester substrate is triacetin; wherein the amount of triacetin in the first component is designed to provide a final concentration of 0.5 wt % to 10 wt % in a reaction formulation formed by combining the first and second components;

(iii) the buffer is in a concentration of about 0.1 wt % to about 10% wt of the first component and said buffer is selected from the group consisting of sodium bicarbonate, potassium bicarbonate, a mixture of sodium bicarbonate and potassium bicarbonate, sodium phosphate, potassium phosphate, and a mixture of sodium phosphate and potassium phosphate;

(iv) the cosolvent is tripropylene glycol methyl ether and is in a concentration of up to 80 wt % of the first component;

(vi) the surfactant is present and is polysorbate 80; and (vi) the hydrogen peroxide in the second component is present in an amount that provides a final concentration in a reaction formulation formed by combining the first and second components of from 0.33 wt % to about 30 wt %.

In another aspect, the multi-component peroxycarboxylic acid generation system further comprises means for applying the aqueous solution of peracetic acid produced by mixing the first and second components to a surface for bleaching or disinfection.

In addition, a method of using the multi-component peroxycarboxylic acid generation system is provided comprising
    (a) employing the means for mixing the first and second components whereby an aqueous formulation comprising peracetic acid is produced; and
    (b) applying the aqueous formulation comprising peracetic acid produced in (a) to a surface, an article of clothing or a textile for bleaching, stain removal, odor reduction, sanitization, disinfection, or a combination thereof.

BRIEF DESCRIPTION OF THE FIGURES

Referring to FIG. 1a, the generic spray bottle system comprises a first chamber [1] containing a first component [2] and a second chamber [3] containing a second component [4]. Transfer tubing [5] is used to transport the first and second components to a flow control elements [6] and [7], preferably having a single adjustment control knob [8] that allows the two components to be mixed at a desired v/v or w/w ratio. FIG. 1a depicts a pump [9] that pumps and mixes both liquid components prior to exiting the spray nozzle [10]. FIG. 1b is similar to FIG. 1a except that the pump [9] and nozzle [10] are configured to delay mixing of the first and second components at the spray nozzle or on the target surface.

Referring to FIG. 2a, the delivery system comprises a dissolvable package comprising a breakable exterior barrier [11] and an internal compartment having an internal compartment barrier [12] comprising a first component [2] that is surrounded by a second component [4]. The internal compartment barrier [12] is designed to be breakable and/or degradable to mix the two components to produce the desired peroxycarboxylic acid. FIG. 2b illustrates a dissolvable packet having the two compartments separated in parallel. As depicted in FIG. 2b, the 2 compartment packet comprises a dissolvable and/or breakable exterior barrier [11] and a first and second compartments [1] and [3] containing components [2], [4] respectively. The first and second compartments separated using a barrier [13].

FIGS. 3a and 3b depict an exemplary system for producing peroxycarboxylic acid according to the present invention using a multi-compartment, flexible squeeze packet/bottle. Referring to FIG. 3a, a manually deformable container [16] comprises a non-rigid wall [14]. Within container [16] is a manually disruptable/breakable internal compartment [15] containing a first component, wherein compartment [15] is surrounded by a second component [4]. Disruption of the internal compartment [15] permits mixing and generation of the activate material. As shown in FIG. 3a, the manually deformable container (e.g., a plastic squeeze bottle) further comprises a directional spout with a removable stopper [17]. FIG. 3b depicts a non-rigid container [16] comprising a first compartment [1] comprising a first component [2] and a second compartment [3] comprising a second component [4] wherein the two compartments are separated in a parallel configuration. The manually deformable bottle in FIG. 3b is also depicted to have a directional spout [18] and a removable stopper [17], wherein the two components are mixed outside of the bottle.

BRIEF DESCRIPTION OF THE BIOLOGICAL SEQUENCES

Figure 1A:
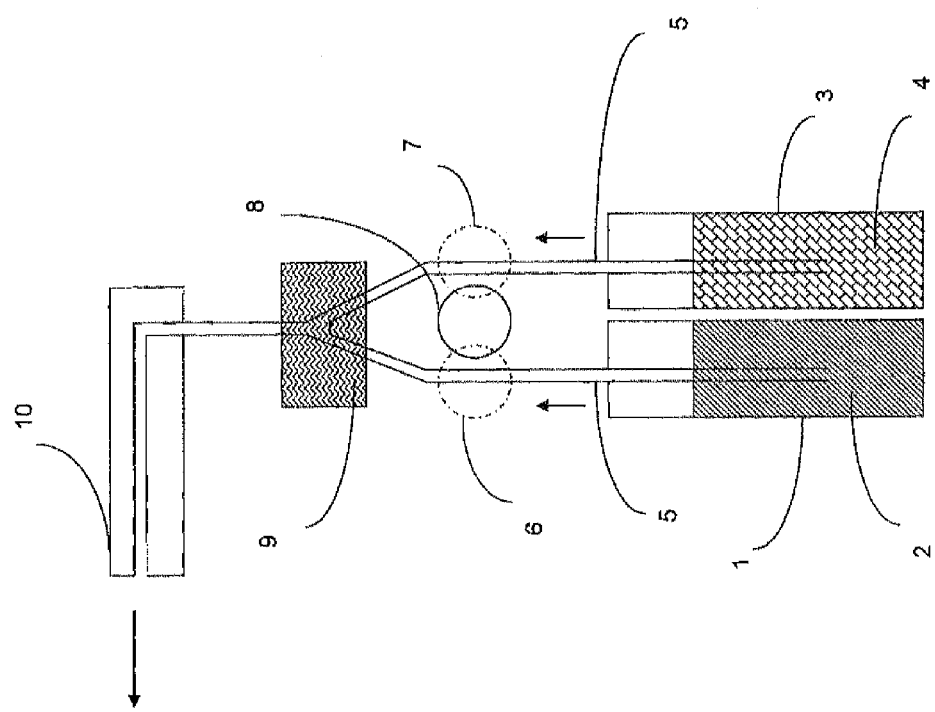
FIGS. 1a and 1b depict an exemplary system for producing peroxycarboxylic acid in accordance with the present invention using a two compartment spray bottle.
Figure 1B:
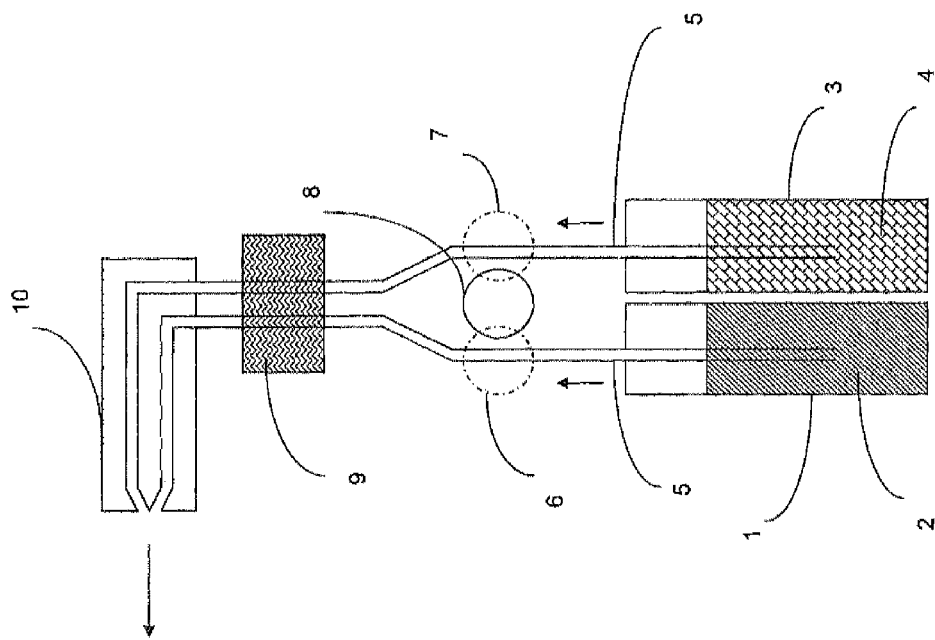
Figure 2A:
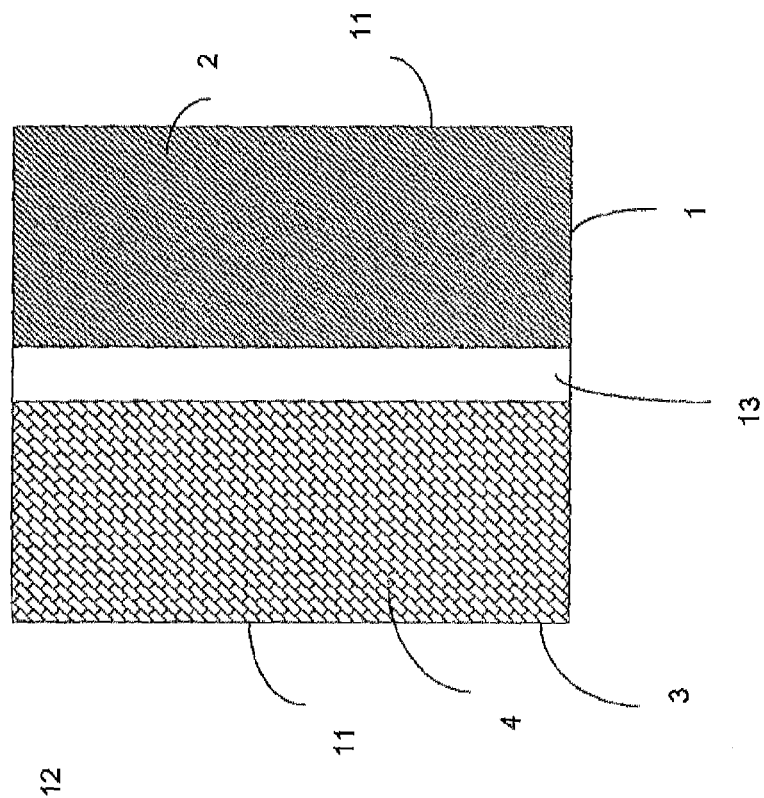
FIGS. 2a and 2b depict an exemplary system for producing peroxycarboxylic acid using multi-compartment packets. The barrier materials form the exterior barrier of the multi-compartment system [11] and/or the internal compartment barrier [12] separating the first component [2] and the second component [4] are designed to be easily degradable and/or breakable (mechanically, chemically, and/or thermally) to generate the aqueous peroxycarboxylic acid mixture.
Figure 2B:
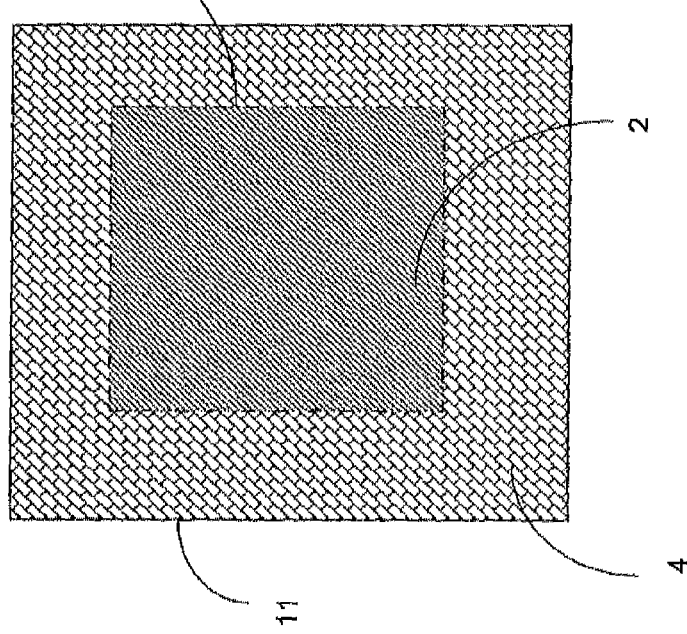

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO:1 is the deduced amino acid sequence of a cephalosporin C deacetylase from *Bacillus subtilis* ATCC® 31954™.

SEQ ID NO:2 is the deduced amino acid sequence of a cephalosporin C deacetylase from *B. subtilis* ATCC® 6633™.

SEQ ID NO:3 is the deduced amino acid sequence of a cephalosporin C deacetylase from *B. licheniformis* ATCC® 14580™.

SEQ ID NO:4 is the deduced amino acid sequence of an acetyl xylan esterase from *B. pumilus* PS213.

SEQ ID NO:5 is the deduced amino acid sequence of an acetyl xylan esterase from *Clostridium thermocellum* ATCC®27405™.

SEQ ID NO:6 is the deduced amino acid sequence of an acetyl xylan esterase from *Thermotoga neapolitana*.

SEQ ID NO:7 is the deduced amino acid sequence of an acetyl xylan esterase from *Thermotoga maritima* MSB8.

SEQ ID NO:8 is the deduced amino acid sequence of an acetyl xylan esterase from *Thermoanaerobacterium* sp. JW/SL YS485.

SEQ ID NO:9 is the deduced amino acid sequence of a cephalosporin C deacetylase from *Bacillus* sp. NRRL B-14911. It should be noted that the nucleic acid sequence encoding the cephalosporin C deacetylase from *Bacillus* sp. NRRL B-14911 as reported in GENBANK® Accession number ZP_01168674 appears to encode a 15 amino acid N-terminal addition that is likely incorrect based on sequence alignments with other cephalosporin C deacetylases and a comparison of the reported length (340 amino acids) versus the observed length of other CAH enzymes (typically 318-325 amino acids in length; see co-owed, co-filed, and copending U.S. patent application under attorney docket number CL4205 US NA entitled "ENZYMATIC PERACID PRODUCTION USING A COSOLVENT"; herein incorporated by reference). As such, the deduced amino acid sequence reported herein for the cephalosporin C deacetylase sequence from *Bacillus* sp. NRRL B-14911 does not include the N-terminal 15 amino acids as reported under GENBANK® Accession number ZP_01168674.

SEQ ID NO:10 is the deduced amino acid sequence of a cephalosporin C deacetylase from *Bacillus halodurans* C-125.

SEQ ID NO:11 is the deduced amino acid sequence of a cephalosporin C deacetylase from *Bacillus clausii* KSM-K16.

SEQ ID NO:12 is the deduced amino acid sequence of a *Bacillus subtilis* ATCC® 29233™ cephalosporin C deacetylase (CAH).

SEQ ID NO:13 is the deduced amino acid sequence of a *Thermoanaerobacterium saccharolyticum* cephalosporin C deacetylase.

SEQ ID NO:14 is the deduced amino acid sequence of a *Thermotoga lettingae* acetyl xylan esterase.

SEQ ID NO:15 is the deduced amino acid sequence of a *Thermotoga petrophila* acetyl xylan esterase.

SEQ ID NO:16 is the deduced amino acid sequence of a first acetyl xylan esterase from *Thermotoga* sp. RQ2 described herein as "RQ2(a)".

SEQ ID NO:17 is the deduced amino acid sequence of a second acetyl xylan esterase from *Thermotoga* sp. RQ2 described herein as "RQ2(b)".

SEQ ID NO:18 is the amino acid sequence of the region encompassing amino acids residues 118 through 299 of SEQ ID NO:1.

SEQ ID NO:19 is the deduced amino acid sequence of a *Thermotoga neapolitana* acetyl xylan esterase variant from co-owned, co-filed, and copending U.S. patent application Attorney Docket No. CL4392 US NA entitled "IMPROVED PERHYDROLASES FOR ENZYMATIC PERACID GENERATION" (incorporated herein by reference in its entirety), where the Xaa residue at position 277 is Ala, Val, Ser, or Thr.

SEQ ID NO:20 is the deduced amino acid sequence of a *Thermotoga maritima* MSB8 acetyl xylan esterase variant from co-owned, co-filed, and copending U.S. patent application Attorney Docket No. CL4392 US NA, where the Xaa residue at position 277 is Ala, Val, Ser, or Thr.

SEQ ID NO:21 is the deduced amino acid sequence of a *Thermotoga lettingae* acetyl xylan esterase variant from co-owned, co-filed, and copending U.S. patent application Attorney Docket No. CL4392 US NA, where the Xaa residue at position 277 is Ala, Val, Ser, or Thr.

SEQ ID NO:22 is the deduced amino acid sequence of a *Thermotoga petrophila* acetyl xylan esterase variant from co-owned, co-filed, and copending U.S. patent application Attorney Docket No. CL4392 US NA, where the Xaa residue at position 277 is Ala, Val, Ser, or Thr.

SEQ ID NO:23 is the deduced amino acid sequence of a *Thermotoga* sp. RQ2 acetyl xylan esterase variant derived from "RQ2(a)" from co-owned, co-filed, and copending U.S. patent application Attorney Docket No. CL4392 US NA, where the Xaa residue at position 277 is Ala, Val, Ser, or Thr.

SEQ ID NO:24 is the deduced amino acid sequence of a *Thermotoga* sp. RQ2 acetyl xylan esterase variant derived from "RQ2(b)" from co-owned, co-filed, and copending U.S. patent application Attorney Docket No. CL4392 US NA, where the Xaa residue at position 278 is Ala, Val, Ser, or Thr.

SEQ ID NO:25 is the deduced amino acid sequence of an acetyl xylan esterase from *Thermoanaerobacterium* sp. JW/SL YS485.

SEQ ID NO:26 is the coding region of a kanamycin resistance gene (kan) from *Streptomyces kanamyceticus*.

SEQ ID NO:27 is plasmid pKD13, which contains the kanamycin resistance gene.

SEQ ID NO:28 is a forward primer used to clone katG from plasmid pKD13.

SEQ ID NO:29 is a reverse primer used to clone katG from plasmid pKD13.

SEQ ID NO:30 is the PCR product of the katG amplification from plasmid pKD13 using the primers of SEQ ID NO:28 and SEQ ID NO:29.

SEQ ID NO:31 is the coding region of the catalase-peroxidase gene (katG).

SEQ ID NO:32 is the deduced amino acid sequence of katG.

SEQ ID NO:33 is plasmid pKD46, which contains the λ-Red recombinase genes.

SEQ ID NO:34 is a forward primer used to confirm disruption of katG.

SEQ ID NO:35 is a reverse primer used to confirm disruption of katG.

SEQ ID NO:36 is the temperature-sensitive plasmid pCP20, which contains the FLP recombinase.

SEQ ID NO:37 is a forward primer used to clone katE from plasmid pKD13.

SEQ ID NO:38 is a reverse primer used to clone katE from plasmid pKD13.

SEQ ID NO:39 is the PCR product of the katE amplification from plasmid pKD13 using the primers of SEQ ID NO:37 and SEQ ID NO:38.

SEQ ID NO:40 is the coding region of the catalase HPII gene (katE).

SEQ ID NO:41 is the deduced amino acid sequence of katE.

SEQ ID NO:42 is a forward primer used to confirm disruption of katE.

SEQ ID NO:43 is a reverse primer used to confirm disruption of katE.

SEQ ID NO:44 is a coding region of a gene encoding acetyl xylan esterase from *Thermotoga neapolitana* as reported in GENBANK® (accession No. AE000512).

SEQ ID NO:45 is a forward primer used to amplify the acetyl xylan esterase gene from *Thermotoga neapolitana*.

SEQ ID NO:46 is a reverse primer used to amplify the acetyl xylan esterase gene from *Thermotoga neapolitana*.

SEQ ID NO:47 is the PCR product of the acetyl xylan esterase amplification using the primers of SEQ ID NO:45 and SEQ ID NO:46.

SEQ ID NO:48 is a gene encoding acetyl xylan esterase from *Thermotoga maritima* as reported in GENBANK® (accession No. NP_227893.1).

SEQ ID NO:49 is a forward primer used to amplify the acetyl xylan esterase gene from *Thermotoga maritima*.

SEQ ID NO:50 is a reverse primer used to amplify the acetyl xylan esterase gene from *Thermotoga maritima*.

SEQ ID NO:51 is the PCR product of the acetyl xylan esterase amplification using the primers of SEQ ID NO:49 and SEQ ID NO:50.

SEQ ID NOs: 52 and 53 are forward and reverse primers as described in Example 25.

SEQ NO: 54 is the nucleic acid sequence of the nucleic acid product amplified by SEQ ID NO: 52 and 53 that was used to prepare plasmid pSW207.

SEQ ID NOs: 55 and 56 are forward and reverse primers as described in Example 25.

SEQ NO: 57 is the codon optimized *Thermotoga maritima* coding sequence used to prepare plasmid pSW228.

SEQ ID NOs 58-65 are forward and reverse primers used to prepare the coding sequences of the *Thermotoga maritima* variants in Example 26.

DETAILED DESCRIPTION OF THE INVENTION

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "substrate", "suitable substrate", and "carboxylic acid ester substrate" interchangeably refer specifically to:
(a) one or more esters having the structure

wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
m is 1 to the number of carbon atoms in $R_5$,
said one or more esters having solubility in water of at least 5 ppm at 25° C.; or
(b) one or more glycerides having the structure

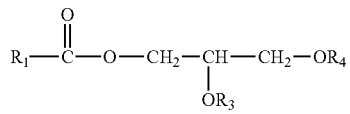

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or
(c) one or more esters of the formula

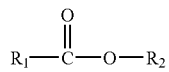

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; or
(d) one or more acetylated monosaccharides, acetylated disaccharides, or acetylated polysaccharides; or
(e) any combination of (a) through (d).

Examples of said carboxylic acid ester substrate may include monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; or any combination thereof.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to, glucose pentaacetate; xylose tetraacetate; acetylated xylan; acetylated xylan fragments; β-D-ribofuranose-1,2,3,5-tetraacetate; tri-O-acetyl-D-galactal; and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof, refer to said compounds comprising at least one ester group of the formula $RC(O)O$, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peroxycarboxylic acid", "suitable reaction components", "suitable aqueous reaction mixture", and "reaction mixture" refer to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peroxycarboxylic acid in situ upon combining the reaction components. As such, the reaction components may be provided as a multicomponent system wherein the reaction components remains separated until use. The design of systems and means for separating and means for mixing the first and second components and means for applying the reaction mixture formed by mixing or combining the components are known in the art and generally will depend upon the physical form of the individual reaction components. For example, multiple active fluids (liquid-liquid) systems typically use multi-chamber dispenser bottles or two-phase systems (U.S. Patent Application Publication No. 2005/0139608; U.S. Pat. Nos. 5,398, 846; 5,624,634; 6,391,840; E.P. Patent 0807156B1; U.S. Patent Application Publication No. 2005/0008526; and PCT Publication No. WO 00/61713) such as found in some bleaching applications wherein the desired bleaching agent is produced upon mixing the reactive fluids. Other forms of multicomponent systems used to generate peroxycarboxylic acid may include, but are not limited to, those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

In another embodiment, the carboxylic acid ester in the first component is selected from the group consisting of monoacetin, diacetin, triacetin, and combinations thereof. In another embodiment, the carboxylic acid ester in the first component is an acetylated saccharide. In another embodiment, the enzyme catalyst in the first component is a particulate solid. In another embodiment, the first reaction component is a solid tablet or powder.

As used herein, the term "perhydrolysis" is defined as the reaction of a selected substrate with peroxide to form a peroxycarboxylic acid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 µmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, all of the present enzymes having perhydrolysis activity are structurally members of the carbohydrate family esterase family 7 (CE-7 family) of enzymes (Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peroxycarboxylic acids from a variety of carboxylic acid ester substrates when combined with a source of peroxygen (WO2007/070609 and U.S. Patent Application Publication Nos. 2008/0176299, 2008/176783, and 2009/0005590 to DiCosimo et al.; each herein incorporated by reference in their entirety).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). Perhydrolases comprising the CE-7 signature motif and/or a substantially similar structure are suitable for use in the present invention. Means to identify substantially similar biological molecules are well known in the art (e.g., sequence alignment protocols, nucleic acid hybridizations and/or the presence of a conserved signature motif). In one aspect, the perhydrolase includes an enzyme comprising the CE-7 signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to one of the sequences provided herein.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229). As described herein, several cephalosporin C deacetylases are provided having significant perhydrolysis activity.

As used herein, "acetyl xylan esterases" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolysis activity.

As used herein, the term "*Bacillus subtilis* ATCC® 31954™" refers to a bacterial cell deposited to the American Type Culture Collection (ATCC) having international depository accession number ATCC® 31954™. *Bacillus subtilis* ATCC® 31954™ has been reported to have an ester hydrolase ("diacetinase") activity capable of hydrolyzing glycerol esters having 2 to 8 carbon acyl groups, especially diacetin (U.S. Pat. No. 4,444,886; herein incorporated by reference in its entirety). As described herein, an enzyme having significant perhydrolase activity has been isolated from *B. subtilis* ATCC® 31954™ and is provided as SEQ ID NO:1. The amino acid sequence of the isolated enzyme has 100% amino acid identity to the cephalosporin C deacetylase provided by GENBANK® Accession No. BAA01729.1.

As used herein, the term "*Bacillus subtilis* ATCC® 29233™" refers to a strain of *Bacillus subtilis* deposited to the American Type Culture Collection (ATCC) having international depository accession number ATCC® 29233™. As described herein, an enzyme having significant perhydrolase activity has been isolated and sequenced from *B. subtilis* ATCC® 29233™ and is provided as SEQ ID NO:12.

As used herein, the term "*Clostridium thermocellum* ATCC® 27405™" refers to a strain of *Clostridium thermocellum* deposited to the American Type Culture Collection (ATCC) having international depository accession number ATCC® 27405™. The amino acid sequence of the enzyme having perhydrolase activity from *C. thermocellum* ATCC® 27405™ is provided as SEQ ID NO:5.

As used herein, the term "*Bacillus subtilis* ATCC® 6633™" refers to a bacterial cell deposited to the American Type Culture Collection (ATCC) having international depository accession number ATCC® 6633™. *Bacillus subtilis* ATCC® 6633™ has been reported to have cephalosporin acetylhydrolase activity (U.S. Pat. No. 6,465,233). The amino acid sequence of the enzyme having perhydrolase activity from *B. subtilis* ATCC® 6633™ is provided as SEQ ID NO:2.

As used herein, the term "*Bacillus licheniformis* ATCC® 14580™" refers to a bacterial cell deposited to the American Type Culture Collection (ATCC) having international depository accession number ATCC® 14580. *Bacillus licheniformis* ATCC® 14580™ has been reported to have cephalosporin acetylhydrolase activity. The amino acid sequence of the enzyme having perhydrolase activity from *B. licheniformis* ATCC® 14580™ is provided as SEQ ID NO:3.

As used herein, the term "*Bacillus pumilus* PS213" refers to a bacterial cell reported to have acetyl xylan esterase activity (GENBANK® AJ249957). The amino acid sequence of the enzyme having perhydrolase activity from *Bacillus pumilus* PS213 is provided as SEQ ID NO:4.

As used herein, the term "*Thermotoga neapolitana*" refers to a strain of *Thermotoga neapolitana* reported to have acetyl xylan esterase activity (GENBANK® AAB70869). The amino acid sequence of the enzyme having perhydrolase activity from *Thermotoga neapolitana* is provided as SEQ ID NO: 6.

As used herein, the term "*Thermotoga maritima* MSB8" refers to a bacterial cell reported to have acetyl xylan esterase activity (GENBANK® NP_227893.1). The amino acid sequence of the enzyme having perhydrolase activity from *Thermotoga maritima* MSB8 is provided as SEQ ID NO: 7.

As used herein, the term "*Bacillus clausii* KSM-K16" refers to a bacterial cell reported to have cephalosporin-C deacetylase activity (GENBANK® YP_175265). The amino acid sequence of the enzyme having perhydrolase activity from *Bacillus clausii* KSM-K16 is provided as SEQ ID NO: 11.

As used herein, the term "*Thermoanearobacterium saccharolyticum*" refers to a bacterial strain reported to have acetyl xylan esterase activity (GENBANK® S41858). The amino acid sequence of the enzyme having perhydrolase activity from *Thermoanearobacterium saccharolyticum* is provided as SEQ ID NO: 13.

As used herein, the term "*Thermotoga lettingae*" refers to a bacterial cell reported to have acetyl xylan esterase activity (GENBANK® CP000812). The deduced amino acid sequence of the enzyme having perhydrolase activity from *Thermotoga lettingae* is provided as SEQ ID NO: 14.

As used herein, the term "*Thermotoga petrophila*" refers to a bacterial cell reported to have acetyl xylan esterase activity (GENBANK® CP000702). The deduced amino acid sequence of the enzyme having perhydrolase activity from *Thermotoga petrophila* is provided as SEQ ID NO: 15.

As used herein, the term "*Thermotoga sp.* RQ2" refers to a bacterial cell reported to have acetyl xylan esterase activity (GENBANK® CP000969). Two different acetyl xylan esterases have been identified from *Thermotoga sp.* RQ2 and are referred to herein as "RQ2(a)" (the deduced amino acid sequence provided as SEQ ID NO: 16) and "RQ2(b)" (the deduced amino acid sequence provided as SEQ ID NO: 17).

As used herein, an "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

As used herein, "substantially similar" refers to nucleic acid molecules wherein changes in one or more nucleotide bases results in the addition, substitution, or deletion of one or more amino acids, but does not affect the functional properties (i.e., perhydrolytic activity) of the protein encoded by the DNA sequence. As used herein, "substantially similar" also refers to an enzyme having an amino acid sequence that is at least 30%, preferably at least 33%, more preferably at least 40%, more preferably at least 50%, even more preferably at least 60%, even more preferably at least 70%, even more preferably at least 80%, yet even more preferably at least 90%, 91%, 92%, 93%, 94%, 95%, 96%, 97%, 98%, or 99% identical to the sequences reported herein wherein the resulting enzyme retains the present functional properties (i.e., perhydrolytic activity). "Substantially similar" may also refer to an enzyme having perhydrolytic activity encoded by nucleic acid molecules that hybridize under stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under stringent conditions (0.1×SSC, 0.1% SDS, 65° C. and washed with 2×SSC, 0.1% SDS followed by 0.1×SSC, 0.1% SDS, 65° C.) with the sequences exemplified herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to, those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gannet (e.g., Gonnet250), protein END-GAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 30%, preferably at least 33%, preferably at least 40%, preferably at least 50%, preferably at least 60%, more preferably at least 70%, more preferably at least 80%, even more preferably at least 85%, even more preferably at least 90%, 91%, 92%, 93%, 94%, 95%, 96%, 97%, 98%, or 99% identical to the amino acid sequences reported herein. Suitable nucleic acid molecules not only have the above homologies, but also typically encode a polypeptide having about 300 to about 340 amino acids, more preferably about 310 to about 330 amino acids, and most preferably about 318 to about 325 amino acids.

As used herein, the terms "signature motif", "CE-7 signature motif", and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence.

As described herein, the present enzymes having perhydrolysis activity ("perhydrolases") belong to the family of CE-7 carbohydrate esterases (DiCosimo et al., U.S. Patent Application Publication No. 2009/0005590). As used herein, the phrase "enzyme is structurally classified as a CE-7 enzyme", "CE-7 perhydrolase" or "structurally classified as a carbohydrate esterase family 7 enzyme" will be used to refer to enzymes having perhydrolysis activity which are structurally classified as a CE-7 carbohydrate esterase. This family of enzymes can be defined by the presence of a signature motif (Vincent et al., supra). The signature motif for CE-7 esterases comprises three conserved motifs (residue position numbering relative to reference sequence SEQ ID NO: 1):

a) Arg118-Gly119-Gln120;
b) Gly179-Xaa180-Ser181-Gln182-Gly183; and
c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO:1) that may be used to further to define a perhydrolase belonging to the CE-7 carbohydrate esterase family. In a further embodiment, the signature motif defined above includes a fourth conserved motif defined as:

Leu267-Xaa268-Asp269.

The Xaa at amino acid residue position 268 is typically isoleucine, valine, or methionine. The fourth motif includes the aspartic acid residue (bold) belonging to the catalytic triad (Ser181-Asp269-His298).

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO:1) to determine the existence of the signature motif. In one embodiment, a CLUSTAL alignment (such as CLUSTALW) using a reference amino acid sequence (as used herein the perhydrolase sequence (SEQ ID NO:1) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (for example, five amino acids of less) within the aligned sequence.

Examples of other suitable algorithms that may be used to identify sequences comprising the present signature motif (when compared to the reference sequence) include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

A comparison of the overall percent identity among perhydrolases exemplified herein indicates that enzymes having as little as 33% identity to SEQ ID NO: 1 (while retaining the signature motif) exhibit significant perhydrolase activity and are structurally classified as CE-7 carbohydrate esterases. In one embodiment, suitable perhydrolases include enzymes comprising the CE-7 signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to SEQ ID NO: 1.

Alternatively, a contiguous amino acid sequence comprising the region encompassing the conserved motifs may also be used to identify CE-7 family members.

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in theft entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

As used herein, the term "expression" refers to the transcription and stable accumulation of sense (mRNA) or anti-sense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. The process produces an efficacious concentration of at least one percarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "disinfection" refers to the act or process of disinfecting. As used herein, the term "antiseptic" refers to a chemical agent that inhibits the growth of disease-carrying microorganisms. In one aspect, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizer" refers to a sanitizing agent. As used herein the term "sanitization" refers to the act or process of sanitizing.

As used herein, the term "virucide" refers to an agent that inhibits or destroys viruses, and is synonymous with "viricide". An agent that exhibits the ability to inhibit or destroy viruses is described as having "virucidal" activity. Peroxycarboxylic acids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peroxycarboxylic acids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction formulation is initially at least 1 mM or more upon combining the reaction components. In one embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g., triglyceride, ($H_2O_2$:substrate) in the aqueous reaction formulation may be from about 0.002 to 20, preferably about 0.1 to 10, and most preferably about 0.5 to 5.

By "oligosaccharide" is meant compounds containing between 2 and at least 24 monosaccharide units linked by glycosidic linkages. The term "monosaccharide" refers to a compound of empirical formula $(CH_2O)_n$, where $n \geq 3$, the carbon skeleton is unbranched, each carbon atom except one contains a hydroxyl group, and the remaining carbon atom is an aldehyde or ketone at carbon atom 2. The term "monosaccharide" also refers to intracellular cyclic hemiacetal or hemiketal forms.

As used herein, the term "excipient" refers to an inactive substance used to stabilize the active ingredient in a formulation, such as the storage stability of the active ingredient. Excipients are also sometimes used to bulk up formulations that contain active ingredients. As described herein, the "active ingredient" is an enzyme catalyst comprising at least one enzyme having perhydrolysis activity. In one embodiment, the active ingredient is at least one CE-7 carbohydrate esterase having perhydrolysis activity.

As used herein, the term "oligosaccharide excipient" means an oligosaccharide that, when added to an aqueous enzyme solution, improves recovery/retention of active enzyme perhydrolase activity) after spray drying and/or improves storage stability of the resulting spray-dried enzyme powder or a formulation of the enzyme powder and an organic substrate. In one embodiment, the addition of the oligosaccharide excipient prior to spray drying improves the storage stability of the enzyme when stored in the carboxylic acid ester (i.e., a storage mixture substantially free of water). The carboxylic acid ester may contain a very low concentration of water, for example, triacetin typically has between 180 ppm and 300 ppm of water. As used herein, the phrase "substantially free of water" will refer to a concentration of water in a formulation of the enzyme powder and the carboxylic acid ester that does not adversely impact the storage stability of enzyme powder when present in the carboxylic acid ester. In a further embodiment, "substantially free of water" may mean less than 2000 ppm, preferably less than 1000 ppm, more preferably less than 500 ppm, and even more preferably less than 250 ppm of water in the formulation comprising the enzyme powder and the carboxylic acid ester, Multi-Component Peroxycarboxylic Acid Generation Systems Peroxycarboxylic acids are quite reactive and generally decrease in concentration over time. This is especially true for commercial pre-formed peroxycarboxylic acid compositions that often lack long term stability. Aqueous solutions of pre-formed peroxycarboxylic acids may also present handling and/or shipping difficulties, especially when shipping large containers and/or highly concentrated peroxycarboxylic acid solutions over longer distances. Further, pre-formed peroxycarboxylic acid solutions may not be able to provide the desired concentration of peroxycarboxylic acid for a particular target application. As such, it is highly desirable to keep the various reaction components separated, especially for liquid formulations.

The use of multi-component peroxycarboxylic acid generation systems comprising two or more components that are combined to produce the desired peroxycarboxylic acid has been reported. The individual components should be safe to handle, easy to ship, and stable for extended periods of time (i.e., as measured by the concentration of peroxycarboxylic acid produced upon mixing). In one embodiment, the storage stability of a multi-component enzymatic peroxycarboxylic acid generation system may be measured in terms of enzyme catalyst stability.

The design of systems and means for separating and combining multiple active components are known in the art and generally will depend upon the physical form of the individual reaction components. For example, multiple active fluids (liquid-liquid) systems typically use multi-chamber dispenser bottles or two-phase systems (e.g., U.S. Patent Application Pub. No. 2005/0139608; U.S. Pat. Nos. 5,398, 846; 5,624,634; 6,391,840; E.P. Patent 0807156B1; U.S. Patent Application. Pub. No. 2005/0008526; and PCT Publication No. WO 00/61713A1) such as found in some bleaching applications wherein the desired bleaching agent is produced upon mixing the reactive fluids. Other forms of multi-component systems used to generate peroxycarboxylic acid may include, but are not limited to, those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888).

United States Published Patent Application No. 2004-0127381 to Scialla et al. describes an aqueous two component laundry product. One part of the two part laundry product comprises a liquid cleaning composition while the second part comprises a bleaching composition; wherein the bleaching composition comprises an equilibrium peroxycarboxylic acid solution comprising a carboxylic acid, a source of peroxygen, and the corresponding peroxycarboxylic acid.

A multi-component peroxycarboxylic acid generation system is provided herein that uses an enzyme catalyst to rapidly produce an aqueous peroxycarboxylic acid solution having a desired peroxycarboxylic acid concentration. The mixing may occur immediately prior to use and/or at the site (in situ) of application. The system will be comprised of at least two components that remain separated until use. Mixing of the components rapidly forms an aqueous peroxycarboxylic acid solution. The composition of each component is designed so that the resulting aqueous peroxycarboxylic acid solution comprises an efficacious peroxycarboxylic acid concentration suitable for the intended end use (e.g., disinfecting, stain removal, odor reduction, and bleaching applications). The composition of the individual components should be designed to (1) provide extended storage stability and (2) provide the ability to enhance formation of a suitable aqueous reaction formulation comprised of peroxycarboxylic acid.

In one embodiment, the mufti-component peroxycarboxylic acid generation system comprises a two component generation system. Various two component generation systems have been reported. In another embodiment, the two component generation system is substantially a two liquid component generation system. At a minimum, the present multi-component peroxycarboxylic acid generation system comprises (1) at least one enzyme catalyst having perhydrolysis activity, wherein said at least one enzyme is structurally classified as a CE-7 esterase, (2) a carboxylic acid ester substrate, and (3) an aqueous source of peroxygen wherein the generation system enzymatically produces the desired peroxycarboxylic acid upon combining the components.

The ingredients and concentration of the ingredients within two component system should to be carefully selected and balanced to provide (1) storage stability of each component, especially the perhydrolysis activity of the enzyme catalyst and (2) physical characteristics that enhance solubility and/or the ability to effectively form the desired aqueous peroxycarboxylic acid solution (e.g., ingredients that enhance the solubility of the ester substrate in the aqueous reaction formulation and/or ingredients that modify the viscosity and/or concentration of at least one of the liquid components [i.e. at least one cosolvent that does not have a significant, adverse effect on the enzymatic perhydrolysis activity]).

A multi-component peroxycarboxylic acid generation system is provided herein. The multi-component generation system may be comprised of at least two substantially liquid components. In one embodiment, the multi-component generation system is a two component system comprising a first liquid component and a second liquid component. The use of the terms "first" or "second" liquid component is relative provided that two different liquid components comprising the specified ingredients remain separated until use.

Co-owned, co-filed, and copending U.S. patent application Attorney Docket No. CL4205 US NA entitled "ENZYMATIC PERACID PRODUCTION USING A COSOLVENT" describes the use of at least one cosolvent to enhance solubility and/or the mixing characteristics of the ester substrate. The component comprising the carboxylic acid ester substrate and the perhydrolase catalyst comprises an organic solvent having a Log P value of less than about 2, wherein Log P is defined as the logarithm of the partition coefficient of a substance between octanol and water, expressed as P=[solute]$_{octanol}$/[solute]$_{water}$. Several cosolvents having a log P value of 2 or less that do not have a significant adverse impact on enzyme activity are described. In one embodiment, the cosolvent is about 20 wt % to about 70 wt % within the reaction component comprising the carboxylic acid ester substrate and the enzyme.

Co-owned, co-filed, and copending U.S. patent application Attorney Docket No. CL4386 US NA entitled "STABILIZATION OF PERHYDROLASES" describes the use of a two component system wherein the first component comprises a formulation of a liquid carboxylic acid ester and solid enzyme powder comprising a formulation of (a) at least one CE-7 esterase having perhydrolysis activity and (b) at least one oligosaccharide excipient; and the second component comprises water having a source of peroxygen and a hydrogen peroxide stabilizer. In one embodiment, the at least one oligosaccharide has a number average molecular weight of at least about 1250 and a weight average molecular weight of at least about 9000. In another embodiment, the oligosaccharide excipient has a number average molecular weight of at least about 1700 and a weight average molecular weight of at least about 15000. In another embodiment, the oligosaccharide is maltodextrin.

Co-owned, co-filed, and copending U.S. patent application Attorney Docket No. CL4387 US NA also entitled "STABILIZATION OF PERHYDROLASES" describes the use of a two component system wherein the first component comprises a formulation of a liquid carboxylic acid ester and solid enzyme powder comprising a formulation of (a) an enzyme powder comprising at least one CE-7 esterase having perhydrolysis activity and at least one excipient and optionally at least one surfactant; and (b) at least one buffer, where in a preferred embodiment the buffer is added as a separate (i.e. separate from the enzyme powder) insoluble component to the carboxylic acid ester substrate; and the second component comprises water having a source of peroxygen and a hydrogen peroxide stabilizer. In one embodiment, the at least one excipient is an oligosaccharide that has a number average molecular weight of at least about 1250 and a weight average molecular weight of at least about 9000. In another embodiment, the at least one excipient is an oligosaccharide that has a number average molecular weight of at least about 1700 and a weight average molecular weight of at least about 15000. In another embodiment, the oligosaccharide is maltodextrin. In a further embodiment, the pH buffer is a bicarbonate buffer. In yet a further embodiment, the hydrogen peroxide stabilizer is TURPINAL® SL.

Compositions and methods of using enzymes having perhydrolysis activity that are structurally classified as being members of the CE-7 carbohydrate esterase family have reported. These "perhydrolase" enzymes are particularly effective in producing peroxycarboxylic acids from a variety of ester substrates when combined with a source of peroxygen (See co-pending and co-owned published International Patent Application no. WO2007/070609 and U.S. Patent Application Publication Nos. 2008/0176299, 2008/176783, and 2009/0005590 to DiCosimo et al.; each herein incorporated by reference in their entirety). The perhydrolases described in the published patent applications to DiCosimo et al. were all based on amino acid sequences reported from previously reported CE-7 esterases (this group includes acetyl xylan esterases (AXEs) and cephalosporin acetyl hydrolases (CAHs)). Co-owned, co-filed, and copending U.S. patent application Attorney Docket No. CL4392 US NA discloses variants of several *Thermotoga* sp. CE-7 esterases having improved perhydrolysis activity and/or improved perhydrolysis activity to hydrolysis activity ratios (i.e., P/H ratios). In one embodiment, the two variant CE-7 perhydrolases have an amino acid sequence selected from the group consisting of SEQ ID NO: 19 and SEQ ID NO: 20.

Enzyme Powder

In one embodiment, the multi-component generation system comprises an enzyme powder comprising a formulation of at least one enzyme structurally classified as a CE-7 enzyme and having perhydrolysis, activity and at least one excipient. In one embodiment, the enzyme powder is formed by spray drying (i.e., a spray-dried formulation). In one embodiment, the excipient is present in the enzyme powder in an amount ranging from about 95 wt % to about 25 wt % of the enzyme powder. In a further aspect, the excipient is an oligosaccharide excipient. In a further aspect, the oligosaccharide excipient has a number average molecular weight of at least about 1250 and a weight average molecular weight of at least about 9000, and optionally at least one surfactant.

The at least one enzyme can be any of the CE-7 carbohydrate esterases described herein or can be any of the CE-7 carbohydrate esterases described in co-owned, copending Published U.S. Patent Application No. 2008/0176299 (incorporated herein by reference in its entirety). In some embodiments, the at least one enzyme is selected from the group consisting of SEQ ID NOs: 1, 2, 3, 4, 5, 6, 7, 8, 9, 10, 11, 12, 13, 14, 15, 16, 17, 19, 20, 21, 22, 23, 24, and 25. In one embodiment, the at least one enzyme comprises an amino acid sequence substantially similar to SEQ ID NOs: 6, 7, 19, or 20. In a preferred embodiment, the at least one enzyme comprises an amino acid sequence selected from the group consisting of SEQ D NOs: 6, 7, 19, and 20.

The at least one enzyme is present in the enzyme powder in an amount in a range of from about 5 weight percent (wt %) to about 75 wt % based on the dry weight of the enzyme powder. A preferred weight percent range of the enzyme in the enzyme powder is from about 10 wt % to 50 wt %, and a more preferred weight percent range of the enzyme in the enzyme powder is from about 20 wt % to 33 wt %.

In one embodiment, the enzyme powder further comprises an excipient. In one aspect, the excipient is provided in an amount in a range of from about 95 wt % to about 25 wt % based on the dry weight of the enzyme powder. A preferred wt % range of excipient in the enzyme powder is from about 90 wt % to 50 wt %, and a more preferred wt % range of excipient in the enzyme powder is from about 80 wt % to 67 wt %.

In yet a further embodiment, the excipient is at least one oligosaccharide excipient. In still a further embodiment, at least one oligosaccharide excipient has a number average molecular weight of at least about 1250 and a weight average molecular weight of at least about 9000. In some embodiments, the oligosaccharide excipient has a number average molecular weight of at least about 1700 and a weight average molecular weight of at least about 15000. Specific oligosaccharides useful in the present invention include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and mixtures thereof. In a preferred embodiment, the oligosaccharide excipient is maltodextrin. Oligosaccharide-based excipients useful in the present invention may include, but are not limited to, water-soluble non-ionic cellulose ethers, such as hydroxymethylcellulose and hydroxypropylmethylcellulose, and mixtures thereof. In yet a further embodiment, the excipient is selected from, but not limited to, one or more of the following compounds: trehalose, lactose, sucrose, mannitol, sorbitol, glucose, cellobiose, α-cyclodextrin, carboxymethylcellulose.

In some embodiments, the formulation used to prepare the enzyme powder optionally comprises at least one surfactant. In a preferred aspect, at least one surfactant is present. Useful surfactants may include, but are not limited to, ionic and nonionic surfactants or wetting agents, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, phospholipids, block copolymers of ethylene glycol and propylene glycol, and non-ionic organosilicones. Preferably, the surfactant is a polyoxyethylene sorbitan fatty add ester, with polysorbate 80 being more preferred.

When part of the formulation used to prepare the enzyme powder, the surfactant is present in an amount in a range of from about 5 wt % to 0.1 wt % based on the weight of protein present in the enzyme powder, preferably from about 2 wt % to 0.5 wt % based on the weight of protein present in the enzyme powder. In a preferred embodiment, the enzyme powder/formulation is formed by spray drying.

The formulation used to prepare the enzyme powder may additionally comprise one or more buffers (e.g., sodium and/or potassium salts of bicarbonate, citrate, acetate, phosphate, pyrophosphate, methylphosphonate, succinate, malate, fumarate, tartrate, or maleate), and an enzyme stabilizer (e.g., ethylenediaminetetraacetic acid, (1hydroxyethylidene)bisphosphonic acid).

Spray-drying of the formulation to form the enzyme powder is carried out, for example, as described generally in *Spray Drying Handbook*, 5th ed., K. Masters, John Wiley & Sons, Inc., NY, N.Y. (1991), and in PCT Patent Publication Nos. WO 97/41833 and WO 96/32149 to Platz, R. et al.

In general spray drying consists of bringing together a highly dispersed liquid and a sufficient volume of hot air to produce evaporation and drying of the liquid droplets. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. (Postfach, Switzerland) or GEA Niro Corp. (Copenhagen, Denmark) will effectively produce particles of desired size. It will further be appreciated that these spray dryers, and specifically their atomizers, may be modified or customized for specialized applications, such as the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein.

The temperature of both the inlet and outlet of the gas used to dry the sprayed material is such that it does not cause degradation of the enzyme in the sprayed material. Such temperatures are typically determined experimentally, although generally, the inlet temperature will range from about 50° C. to about 225° C., while the outlet temperature will range from about 30° C. to about 150° C. Preferred parameters include atomization pressures ranging from about 20-150 psi (0.14 MPa-1.03 MPa), and preferably from about 30-40 to 100 psi (0.21-0.28 MPa to 0.69 MPa). Typically the atomization pressure employed will be one of the following (MPa) 0.14, 0.21, 0.28, 0.34, 0.41, 0.48, 0.55, 0.62, 0.69, 0.76, 0.83 or above.

The enzyme powder or a formulation of the enzyme powder in carboxylic acid ester substantially retains its enzymatic activity for an extended period of time when stored at ambient temperature. The enzyme powder or a formulation of the enzyme powder in carboxylic acid ester substantially retains its enzymatic activity at elevated temperatures for short periods of time. In one embodiment, "substantially retains its enzymatic activity" is meant that the enzyme powder or a formulation of the enzyme powder in carboxylic acid ester retains at least about 75 percent of the enzyme activity of the enzyme in the enzyme powder or a formulation of the enzyme powder after an extended storage period at ambient temperature and/or after a short storage period at an elevated temperature (above ambient temperature) in a formulation comprised of a carboxylic acid ester and the enzyme powder as compared to the initial enzyme activity of the enzyme powder prior to the preparation of a formulation comprised of the carboxylic acid ester and the enzyme powder. The extended storage period is a period of time of from about one year to about two years at ambient temperature. In one embodiment, the short storage period is at an elevated temperature is a period of time of from when the formulation comprised of a carboxylic acid ester and the enzyme powder is produced at 40° C. to about eight weeks at 40° C. In another embodiment, the elevated temperature is in a range of from about 30° C. to about 52° C. In a preferred embodiment, the elevated temperature is in a range of from about 30° C. to about 40° C.

In some embodiments, the enzyme powder has at least 75 percent of the enzyme activity of the at least one enzyme after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. In other embodiments, the enzyme powder has at least 76, 77, 78, 79, 80, 81, 82, 83, 84, 85, 86, 87, 88, 89, 90, 91, 92, 93, 94, 95, 96, 97, 98, 99, or 100 percent of the enzyme activity of the at least one enzyme after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. Preferably, perhydrolysis activity is measured as described in Example 8-13, infra, but any method of measuring perhydrolysis activity can be used in the practice of the present invention.

In some embodiments, further improvement in enzyme activity over the stated periods of time can be achieved by adding a buffer having a buffering capacity in a pH range of from about 5.5 to about 9.5 to the formulation comprised of the carboxylic acid ester and the spray-dried enzyme powder. Suitable buffer for use in the formulation may include, but is not limited to, sodium salt, potassium salt, or mixtures of sodium or potassium salts of bicarbonate, pyrophosphate, phosphate, methylphosphonate, citrate, acetate, malate, fumarate, tartrate maleate or succinate. Preferred buffers for use in the formulation comprised of the carboxylic acid ester and the spray-dried enzyme powder include the sodium salt, potassium salt, or mixtures of sodium or potassium salts of bicarbonate, pyrophosphate, phosphate, methylphosphonate, citrate, acetate, malate, fumarate, tartrate maleate or succinate. In preferred embodiment, the buffer comprises the sodium and/or potassium salts of bicarbonate.

In embodiments where a buffer is present in the carboxylic add ester and enzyme powder formulation, the buffer may be present in an amount in a range of from about 0.01 wt % to about 50 wt % based on the weight of carboxylic acid ester in the formulation comprised of carboxylic acid ester and enzyme powder. The buffer may be present in a more preferred range of from about 0.10% to about 10% based on the weight of carboxylic acid ester in the formulation comprised of carboxylic acid ester and enzyme powder. Further, in these embodiments, the comparison between perhydrolysis activity of the enzyme is determined as between an enzyme powder which retains at least 75 percent of the perhydrolysis activity of the at least one enzyme after eight weeks storage at 40° C. in a formulation comprised of a carboxylic acid ester, a buffer having a buffering capacity in a pH range of from about 5.5 to about 9.5, and the enzyme powder as compared to the initial perhydrolysis activity of the enzyme powder prior to the preparation of a formulation comprised of the carboxylic acid ester, the buffer having a buffering capacity in a pH range of from about 5.5 to about 9.5, and the enzyme powder.

It is intended that the enzyme powder be stored as a formulation in the organic compound that is a substrate for the at least one enzyme, such as triacetin. In the absence of added hydrogen peroxide, triacetin is normally hydrolyzed in aqueous solution by a CE-7 carbohydrate esterase to produce diacetin and acetic acid, and the production of acetic acid results in a decrease in the pH of the reaction formulation. One requirement for long term storage stability of the enzyme in triacetin is that there is not a significant reaction of the triacetin with any water that might be present in the triacetin; the specification for water content in one commercial triacetin (supplied by Tessenderlo Group, Brussels, Belgium) is 0.03 wt % water (300 ppm). Any hydrolysis of triacetin that occurs during storage of the enzyme in triacetin would produce acetic acid, which could result in a decrease in activity or inactivation of the CE-7 perhydrolases; the perhydrolases are typically inactivated at or below a pH of 5.0 (see U.S. Patent Application Publication No. 2009/0005590 to DiCosimo, R., et al.). The excipient selected for use in the present application must provide stability of the enzyme in the organic substrate for the enzyme under conditions where acetic acid might be generated due to the presence of low concentrations of water in the formulation.

Suitable Reaction Conditions for the Enzyme-Catalyzed Preparation of Peroxycarboxylic Acids from Carboxylic Acid Esters and Hydrogen Peroxide In one aspect of the invention, a process is provided to produce an aqueous formulation comprising a peroxycarboxylic acid by reacting carboxylic acid esters with a source of peroxygen (including, but not limited to, hydrogen peroxide, sodium perborate or sodium percarbonate) in the presence of an enzyme catalyst having perhydrolysis activity. In one embodiment, the enzyme catalyst comprises at least one enzyme having perhydrolysis activity, wherein said enzyme is structurally classified as a member of the CE-7 carbohydrate esterase family (CE-7; see Coutinho, P. M., and Henrissat, B., supra). In another embodiment, the perhydrolase catalyst is structurally classified as a cephalosporin C deacetylase. In another embodiment, the perhydrolase catalyst is structurally classified as an acetyl xylan esterase.

In one embodiment, the perhydrolase catalyst comprises an enzyme having perhydrolysis activity and a signature motif comprising:
 a) an RGQ motif at amino acid residues 118-120;
 b) a GXSQG motif at amino acid residues 179-183; and
 c) an HE motif at amino acid residues 298-299 when aligned to reference sequence SEQ ID NO:1 using CLUSTALW.

In a further embodiment, the signature motif additional comprises a fourth conserved motif defined as an LXD motif at amino acid residues 267-269 when aligned to reference sequence SEQ ID NO:1 using CLUSTALW.

In another embodiment, the perhydrolase catalyst comprises an enzyme having the present signature motif and at least 30% amino acid to SEQ ID NO:1.

In another embodiment, the perhydrolase catalyst comprises an enzyme having perhydrolase activity selected from the group consisting of SEQ ID NOs: 1, 2, 3, 4, 5, 6, 7, 8, 9, 10, 11, 12, 13, 14, 15, 16, 17, 19, 20, 21, 22, 23, 24, and 25.

In another embodiment, the perhydrolase catalyst comprises an enzyme having at least 40% amino acid identity to a contiguous signature motif defined as SEQ ID NO:18 wherein the conserved motifs described above (i.e., RGQ, GXSQG, and HE, and optionally, LXD) are conserved.

In another embodiment, the perhydrolase catalyst comprises an enzyme having an amino acid sequence selected from the group consisting of SEQ ID NOs: 1, 2, 3, 4, 5, 6, 7, 8, 9, 10, 11, 12, 13, 14, 15, 16, 17, 19, 20, 21, 22, 23, 24, and 25, wherein said enzyme may have one or more additions, deletions, or substitutions so long as the signature motif is conserved and perhydrolase activity is retained.

Suitable carboxylic acid ester substrates may include esters having the following formula:
 (a) one or more esters having the structure

wherein
 X is an ester group of the formula $R_6C(O)O$;
 $R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
 $R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
 m is 1 to the number of carbon atoms in $R_5$,
 said one or more esters having solubility in water of at least 5 ppm at 25° C.; or
 (b) one or more glycerides having the structure

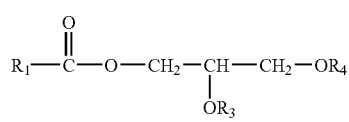

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or
 (c) one or more esters of the formula

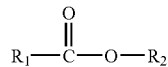

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)$—$O)_nH$ and n is 1 to 10; or
 (d) one or more acetylated monosaccharides, acetylated disaccharides, or acetylated polysaccharides; or
 (e) any combination of (a) through (d).

Examples of said carboxylic acid ester substrate may include monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; or any combination thereof.

In a preferred embodiment, the carboxylic acid ester is a liquid substrate selected from the group consisting of monoacetin, diacetin, triacetin, and combinations (i.e., mixtures) thereof. The carboxylic acid ester is present in the reaction formulation at a concentration sufficient to produce the desired concentration of peroxycarboxylic acid upon enzyme-catalyzed perhydrolysis. The carboxylic acid ester need not be completely soluble in the reaction formulation, but has sufficient solubility to permit conversion of the ester by the perhydrolase catalyst to the corresponding peroxycarboxylic acid. The carboxylic acid ester is present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation. The peroxygen source may include, but is not limited to, hydrogen peroxide, hydrogen peroxide adducts (e.g., urea-hydrogen peroxide adduct (carbamide peroxide)) perborate salts and percarbonate salts. The concentration of peroxygen compound in the reaction formulation may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction formulation. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

In another embodiment, the enzyme catalyst lacks significant catalase activity or is engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e., knocked-out). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see Published U.S. Patent Application No. 2008-0176299). In another embodiment, the production host is an *E. coli* strain comprising a down-regulation and/or disruption in both katG and a katE catalase genes.

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 10 mg per mL of total reaction volume, preferably from 0.001 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peroxycarboxylic acid generated by the combination of chemical perhydrolysis and enzymatic perhydrolysis of the carboxylic acid ester is sufficient to provide an effective concentration of peroxycarboxylic acid for bleaching, stain removal, sanitization, odor reduction or disinfection at a desired pH. In another aspect, the present methods provide combinations of enzymes and enzyme substrates to produce the desired effective concentration of peroxycarboxylic acid, where, in the absence of added enzyme, there is a significantly lower concentration of peroxycarboxylic acid produced. Although there may in some cases be substantial chemical perhydrolysis of the enzyme substrate by direct chemical reaction of inorganic peroxide with the enzyme substrate, there may not be a sufficient concentration of peroxycarboxylic acid generated to provide an effective concentration of peroxycarboxylic acid in the desired applications, and a significant increase in total peroxycarboxylic acid concentration is achieved by the addition of an appropriate perhydrolase catalyst to the reaction formulation.

The concentration of peroxycarboxylic acid generated (such as peracetic acid) by the perhydrolysis of at least one carboxylic acid ester is at least about 20 ppm, preferably at least 100 ppm, more preferably at least about 200 ppm peroxycarboxylic acid, more preferably at least 300 ppm, more preferably at least 500 ppm, more preferably at least 700 ppm, more preferably at least about 1000 ppm peroxycarboxylic acid, most preferably at least 2000 ppm peroxycarboxylic acid within 10 minutes, preferably within 5 minutes, of initiating the perhydrolysis reaction. The product formulation comprising the peroxycarboxylic acid may be optionally diluted with water, or a solution predominantly comprised of water, to produce a formulation with the desired lower concentration of peroxycarboxylic acid. In one aspect, the reaction time required to produce the desired concentration of peroxycarboxylic acid is not greater than about two hours, preferably not greater than about 30 minutes, more preferably not greater than about 10 minutes, and most preferably in about 5 minutes or less. In other aspects, a hard surface or inanimate object contaminated with a concentration of biological contaminant(s) is contacted with the peroxycarboxylic acid formed in accordance with the processes described herein within about 5 minutes to about 168 hours of combining said reaction components, or within about 5 minutes to about 48 hours, or within about 5 minutes to 2 hours of combining said reaction components, or any such time interval therein.

In another aspect, the peroxycarboxylic acid formed in accordance with the processes describe herein is used in a laundry care application wherein the peroxycarboxylic acid is contacted with a textile to provide a benefit, such as disinfecting, sanitizing, bleaching, destaining, deodorizing/odor reduction or a combination thereof. The peroxycarboxylic acid may be used in a variety of laundry care products including, but not limited to, textile pre-wash treatments, laundry detergents, stain removers, bleaching compositions, deodorizing compositions, and rinsing agents. In one embodiment, the present process to produce a peroxycarboxylic acid for a target surface is conducted in situ.

In connection with the present systems and methods for laundry care where the peracid is generated for one or more of bleaching, stain removal, and odor reduction, the concentration of peracid generated (e.g., peracetic acid) by the perhydrolysis of at least one carboxylic acid ester may be at least about 2 ppm, preferably at least 20 ppm, preferably at least 100 ppm, and more preferably at least about 200 ppm peracid. In connection with the present systems and methods for laundry care where the peracid is generated for disinfection or sanitization, the concentration of peracid generated (e.g., peracetic acid) by the perhydrolysis of at least one carboxylic acid ester may be at least about 2 ppm, more preferably at least 20 ppm, more preferably at least 200 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product mixture comprising the peracid may be optionally diluted with water, or a solution predominantly comprised of water, to produce a mixture with the desired lower concentration of peracid. In one aspect of the present methods and systems, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less.

The temperature of the reaction is chosen to control both the reaction rate and the stability of the enzyme catalyst activity. The temperature of the reaction may range from just above the freezing point of the reaction formulation (approximately 0° C.) to about 95° C., with a preferred range of 5° C. to about 75° C., and a more preferred range of reaction temperature of from about 5° C. to about 55° C.

The pH of the final reaction formulation containing peroxycarboxylic acid is from about 2 to about 9, preferably from about 3 to about 8, more preferably from about 5 to about 8, even more preferably about 5.5 to about 8, and yet even more preferably about 6.0 to about 7.5. In another embodiment, the pH of the reaction formulation is acidic (pH<7). The pH of the reaction, and of the final reaction formulation, may optionally be controlled by the addition of a suitable buffer, including, but not limited to, phosphate, pyrophosphate, bicarbonate, acetate, or citrate. The concentration of buffer, when employed, is typically from 0.1 mM to 1.0 M, preferably from 1 mM to 300 mM, most preferably from 10 mM to 100 mM.

In another aspect, the enzymatic perhydrolysis reaction formulation may contain an organic solvent that acts as a dispersant to enhance the rate of dissolution of the carboxylic acid ester in the reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to, buffers, detergent builders, thickening agents, emulsifiers, surfactants, wetting agents, corrosion inhibitors (such as benzotriazole), enzyme stabilizers, and peroxide stabilizers (e.g., metal ion chelating agents). Many of the additional components are well known in the detergent industry (see, for example, U.S. Pat. No. 5,932,532; hereby incorporated by reference). Examples of emulsifiers include, but are not limited to, polyvinyl alcohol or polyvinylpyrrolidone. Examples of thickening agents include, but are not limited to, LAPONITE® RD, corn starch, PVP, CARBOWAX®, CARBOPOL®, CABOSIL®, polysorbate 20, PVA, and lecithin. Examples of buffering systems include, but are not limited to, sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to, a) non-ionic surfactants such as block copolymers of ethylene oxide or propylene oxide, ethoxylated or propoxylated linear and branched primary and secondary alcohols, and aliphatic phosphine oxides; b) cationic surfactants such as quaternary ammonium compounds, particularly quaternary ammonium compounds having a C8-C20 alkyl group bound to a nitrogen atom additionally bound to three C1-C2 alkyl groups; c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates; and d) amphoteric and zwitterionic surfactants such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL (CAS# 2809-21-4), DEQUEST® 0520, DEQUEST® 0531, stabilizers of enzyme activity (e.g., polyethylene glycol (PEG)), and detergent builders.

In Situ Production of Peroxycarboxylic Acids Using a Perhydrolase Catalyst

Cephalosporin C deacetylases (E.C. 3.1.1.41; systematic name cephalosporin C acetylhydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbial.* 30(3):413-419 (1975)). CAHs belong to a larger family of structurally related enzymes referred to as the carbohydrate esterase family seven (CE-7; see Coutinho, P. M., Henrissat, B., supra).

The CE-7 family includes both CAHs and acetyl xylan esterases (AXEs; E.C. 3.1.1.72). CE-7 family members share a common structural motif and are quite unusual in that they typically exhibit ester hydrolysis activity for both acetylated xylooligosaccharides and acetylated cephalosporin C, suggesting that the CE-7 family represents a single class of proteins with a multifunctional deacetylase activity against a range of small substrates (Vincent et al., supra). Vincent et al. describes the structural similarity among the members of this family and defines a signature sequence motif characteristic of the CE-7 family.

Members of the CE-7 family are found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ. Microbiol.,* 63(12):4807-4811 (1997); Sakai et al., *J. Ferment. Bioeng.* 85:53-57 (1998); Lorenz, W. and Wiegel, J., *J. Bacteriol* 179:5436-5441 (1997); Cardoza et al., *Appl. Microbiol. Biotechnol.,* 54(3):406-412 (2000); Mitsushima et al., supra; Abbott, B. and Fukuda, D., *Appl. Microbiol.* 30(3):413-419 (1975); Vincent et al., supra; Takami et al., *NAR,* 28(21):4317-4331 (2000); Rey et al., *Genome Biol.,* 5(10): article 77 (2004); Degrassi et al., *Microbiology.,* 146:1585-1591 (2000); U.S. Pat. Nos. 6,645,233;. 5,281,525; 5,338,676; and WO 99/03984.

WO2007/070609 and U.S. Patent Application Publication Nos. 2008/0176299, 2008/176783 and 2009/0005590 to DiCosimo et al. disclose various enzymes structurally classified as CE-7 enzymes that have perhydrolysis activity suitable for producing efficacious concentrations of peroxycarboxylic acids from a variety of carboxylic acid ester substrates when combined with a source of peroxygen. Variant CE-7 enzymes having improved perhydrolysis activity are also described in a co-filed, co-owned, and copending U.S. patent application (Attorney Docket No. CL4392 US NA entitled "IMPROVED PERHYDROLASES FOR ENZYMATIC PERACID GENERATION", incorporated herein by reference in its entirety).

The present method produces industrially-useful, efficacious concentrations of peroxycarboxylic acids in situ under aqueous reaction conditions using the perhydrolase activity of an enzyme belonging to the CE-7 family of carbohydrate esterases.

HPLC Assay Method for Determining the Concentration of Peroxycarboxylic Acid and Hydrogen Peroxide.

A variety of analytical methods can be used in the present methods to analyze the reactants and products including, but not limited to, titration, high performance liquid chromatography (HPLC), gas chromatography (GC), mass spectroscopy (MS), capillary electrophoresis (CE), the analytical procedure described by U. Karst et al., (*Anal. Chem.*, 69(17): 3623-3627 (1997), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

Determination of Minimum Biocidal Concentration of Peroxycarboxylic Acids

The method described by J. Gabrielson, et al. (*J. Microbial. Methods* 50: 63-73 (2002)) can be employed for determination of the Minimum Biocidal Concentration (MBC) of peroxycarboxylic acids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation*, 5$^{th}$ edition, Lippincott Williams & Wilkins, Philadelphia, Pa., USA; 2001).

Uses of Enzymatically-Prepared Peroxycarboxylic Acid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (e.g., articles of clothing, garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g., certain proteases) to additionally provide biocidal activity. In a preferred aspect, the present peroxycarboxylic acid compositions are particularly useful as a disinfecting agent for non-autoclavable medical instruments and food packaging equipment. As the peroxycarboxylic acid-containing formulation may be prepared using GRAS or food-grade components (enzyme, enzyme substrate, hydrogen peroxide, and buffer), the enzyme-generated peroxycarboxylic acid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect or sanitize surfaces and/or objects contaminated (or suspected of being contaminated) with biological contaminants by contacting the surface or object with the products produced by the present processes. As used herein, "contacting" refers to placing a disinfecting composition comprising an effective concentration of peroxycarboxylic acid in contact with the surface or inanimate object suspected of contamination with a biological contaminant for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a microbial population. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates); sulfonic acids (e.g., dodecylbenzene sulfonic acid); iodo-compounds or active halogen compounds (e.g., elemental halogens, halogen oxides (e.g., NaOCl, HOCl, HOBr, ClOC$_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite); organic peroxides including benzoyl peroxide, alkyl benzoyl peroxides, ozone, singlet oxygen generators, and mixtures thereof; phenolic derivatives (e.g., o-phenyl phenol, o-benzyl-p-chlorophenol, tent-amyl phenol and $C_1$-$C_6$ alkyl hydroxy benzoates); quaternary ammonium compounds (e.g., alkyldimethylbenzyl ammonium chloride, dialkyldimethyl ammonium chloride and mixtures thereof); and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the present process can be used to reduce the concentration of biological contaminants (such as a viable microbial population) when applied on and/or at a locus. As used herein, a "locus" of the invention comprises part or all of a target surface suitable for disinfecting or bleaching. Target surfaces include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces may also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces may include brick, tile, ceramic, porcelain, wood, vinyl, linoleum, and carpet.

The peroxycarboxylic acids formed by the present process may be used to provide a benefit to an article of clothing or a textile including, but not limited to, bleaching, odor reduction, stain removal, and disinfection. The peroxycarboxylic acids formed by the present process may be used in any number of laundry care products including, but not limited to, textile/clothing pre-wash treatments, laundry detergents, stain removers, bleaching compositions, deodorizing compositions, and rinsing agents.

In the context of laundry care applications, the term "contacting an article of clothing or textile" means that the article of clothing or textile is exposed to a formulation disclosed herein. To this end, there are a number of formats the formulation may be used to treat articles of clothing or textiles including, but not limited to, liquid, solids, gel, paste, bars, tablets, spray, foam, powder, or granules and can be delivered via hand dosing, unit dosing, dosing from a substrate, spraying and automatic dosing from a laundry washing or drying machine. Granular compositions can also be in compact form; liquid compositions can also be in a concentrated form.

When the formulations disclosed herein are used in a laundry machine, the formulation can further contain components typical to laundry detergents. For example, typical components included, but are not limited to, surfactants, bleaching agents, bleach activators, additional enzymes, suds suppressors, dispersants, lime-soap dispersants, soil suspension and anti-redeposition agents, softening agents, corrosion inhibitors, tarnish inhibitors, germicides, pH adjusting agents, non-builder alkalinity sources, chelating agents, organic and/or inorganic fillers, solvents, hydrotropes, optical brighteners, dyes, and perfumes.

The formulations disclosed herein can also be used as detergent additive products in solid or liquid form. Such additive products are intended to supplement or boost the performance of conventional detergent compositions and can be added at any stage of the cleaning process.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella*, and *Myxococcus*. In one embodiment, bacterial host strains include *Escherichia, Bacillus, Kluyveromyces*, and *Pseudomonas*. In a preferred embodiment, the bacterial host cell is *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters which are useful to drive expression of the present cephalosporin C deacetylase coding region in the desired host cell are numerous and familiar to those skilled in the art. Virtually any promoter capable of driving these genes is suitable for the present invention including, but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived from the preferred host cell.

Industrial Production

A variety of culture methodologies may be applied to produce the perhydrolase catalyst. For example, large-scale production of a specific gene product overexpressed from a recombinant microbial host may be produced by batch, fed-batch, and continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

Commercial production of the desired perhydrolase catalyst may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired perhydrolase catalysts from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

GENERAL METHODS

The following examples are provided to demonstrate preferred aspects of the invention. It should be appreciated by those of skill in the art that the techniques disclosed in the examples follow techniques to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods and examples.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "µg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, "Tg" means glass transition temperature, and "EDTA" means ethylenediaminetetraacetic acid.

EXAMPLE 1

Construction of a katG Catalase Disrupted *E. coli* Strain

The coding region of the kanamycin resistance gene (kan; SEQ ID NO:26) was amplified from the plasmid pKD13 (SEQ ID NO:27) by PCR (0.5 min at 94° C., 0.5 min at 55° C., 1 min at 70° C., 30 cycles) using primers identified as SEQ ID NO:28 and SEQ ID NO:29 to generate the PCR product identified as SEQ ID NO:30. The katG nucleic acid sequence is provided as SEQ ID NO:31 and the corresponding amino acid sequence is SEQ ID NO:32. *E. coli* MG1655 (ATCC® 47076™) was transformed with the temperature-sensitive plasmid pKD46 (SEQ ID NO:33), which contains the λ-Red recombinase genes (Datsenko and Wanner, (2000), *PNAS USA* 97:6640-6645), and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system (Gentra Systems, Minneapolis, Minn.), and checked by PCR to confirm disruption of the katG gene using primers identified as SEQ ID NO:34 and SEQ ID NO:35. Several katG-disrupted strains were transformed with the temperature-sensitive plasmid pCP20 (SEQ ID NO:36), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 and MG1655 KatG2.

EXAMPLE 2

Construction of a katE Catalase Disrupted *E. coli* Strain

The kanamycin resistance gene (SEQ ID NO:26) was amplified from the plasmid pKD13 (SEQ ID NO:27) by PCR (0.5 min at 94° C., 0.5 min at 55° C., 1 min at 70° C., 30 cycles) using primers identified as SEQ ID NO:37 and SEQ ID NO:38 to generate the PCR product identified as SEQ ID NO:39. The katE nucleic acid sequence is provided as SEQ ID NO:40 and the corresponding amino acid sequence is SEQ ID NO:41. *E. coli* MG1655 (ATCC® 47076™) was transformed with the temperature-sensitive plasmid pKD46 (SEQ ID NO: 33), which contains the λ-Red recombinase genes, and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO: 42 and SEQ ID NO: 43. Several katE-disrupted strains were transformed with the temperature-sensitive plasmid pCP20 (SEQ ID NO: 36), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatE1 and MG1655 KatE2.

EXAMPLE 3

Construction of a katG Catalase and katE Catalase Disrupted *E. coli* Strain (KLP18)

The kanamycin resistance gene (SEQ ID NO:26) was amplified from the plasmid pKD13 (SEQ ID NO:27) by PCR (0.5 min at 94° C., 0.5 min at 55° C., 1 min at 70° C., 30 cycles) using primers identified as SEQ ID NO:37 and SEQ ID NO:38 to generate the PCR product identified as SEQ ID NO:39. *E. coli* MG1655 KatG1 (EXAMPLE 1) was transformed with the temperature-sensitive plasmid pKD46 (SEQ ID NO:33), which contains the λ-Red recombinase genes, and selected on LB-amp plates for 24 h at 30° C. MG1655 KatG1/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO:42 and SEQ ID NO:43. Several katE-disrupted strains (Δ katE) were transformed with the temperature-sensitive plasmid pCP20 (SEQ ID NO:36), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG 1655 KatG1KatE18.1 and MG1655 KatG1KatE23. MG1655 KatG1KatE18.1 is designated *E. coli* KLP18.

EXAMPLE 4

Cloning and Expression of Perhydrolase from *Thermotoga neapolitana*

The coding region of the gene encoding acetyl xylan esterase from *Thermotoga neapolitana* as reported in GENBANK® (accession number AE000512; region 80481-81458; SEQ ID NO:44) was synthesized using codons optimized for expression in *E. coli* (DNA 2.0, Menlo Park, Calif.). The coding region of the gene was subsequently amplified by PCR (0.5 min at 94° C., 0.5 min at 55° C., 1 min at 70° C., 30 cycles) using primers identified as SEQ ID NO: 45 and SEQ ID NO: 46. The resulting nucleic acid product (SEQ ID NO: 47) was subcloned into pTrcHis2-TOPO® to generate the plasmid identified as pSW196. The plasmid pSW196 was used to transform *E. coli KLP*18 (EXAMPLE 3) to generate the strain KLP18/pSW196. KLP18/pSW196 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

EXAMPLE 5

Cloning and Expression of Perhydrolase from *Thermotoga maritima* MSB8

The coding region of the gene encoding acetyl xylan esterase from *Thermotoga maritima* MSB8 as reported in GENBANK® (accession # NP_227893.1; SEQ ID NO: 48) was synthesized (DNA 2.0, Menlo Park, Calif.). The coding region of the gene was subsequently amplified by PCR (0.5 min @ 94° C., 0.5 min @ 55° C., 1 min @ 70° C., 30 cycles) using primers identified as SEQ ID NO:49 and SEQ ID NO:50. The resulting nucleic acid product (SEQ ID NO:51) was cut with restriction enzymes PstI and XbaI and subcloned between the PstI and XbaI sites in pUC19 to generate the plasmid identified as pSW207. The plasmid pSW207 was used to transform *E. coli* KLP18 (EXAMPLE 3) to generate the strain identified as KLP18/pSW207. KLP18/pSW207 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase enzyme at 20-40% of total soluble protein.

EXAMPLE 6

Fermentation of *E. coli* KLP18 Transformants Expressing Perhydrolase

A fermentor seed culture was prepared by charging a 2-L shake flask with 0.5 L seed medium containing yeast extract (Amberex 695, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 and the medium was sterilized in the flask. Post sterilization additions included glucose (50 wt %, 10.0 mL) and 1 mL ampicillin (25 mg/mL) stock solution. The seed medium was inoculated with a 1-mL culture of *E. coli* KLP18/pSW196 or *E. coli* KLP18/pSW207 in 20% glycerol, and cultivated at 35° C. and 300 rpm. The seed culture was transferred at ca. 1-2 $OD_{550nm}$ to a 14-L fermentor (Braun Biotech, Allentown, Pa.) with 8 L of medium at 35° C. containing $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Amberex 695, 5.0 g/L), Biospumex153K antifoam (0.25 mL/L, Cognis Corporation, Monheim, Germany), NaCl (1.0 g/L), $CaCl_2$ dihydrate (10 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 80.0 g) and ampicillin (25 mg/mL) stock solution (16.00 mL). Glucose solution (50% w/w) was used for fed batch. Glucose feed was initiated when glucose concentration decreased to 0.5 g/L, starting at 0.31 g feed/min and increasing progressively each hour to 0.36, 0.42, 0.49, 0.57, 0.66, 0.77, 0.90, 1.04, 1.21, 1.41, and 1.63 g/min respectively; the rate remained constant afterwards. Glucose concentration in the medium was monitored and if the concentration exceeded 0.1 g/L the feed rate was decreased or stopped temporarily. Induction was initiated between $OD_{550nm}$=56 and $OD_{550nm}$=80 with addition of 16 mL IPTG (0.5 M) for the various strains. The dissolved oxygen (DO) concentration was controlled at 25% of air saturation. The DO was controlled first by impeller agitation rate (400 to 1400 rpm) and later by aeration rate (2 to 10 slpm). The pH was controlled at 6.8. $NH_4OH$ (29% w/w) and $H_2SO_4$ (20% w/v) were used for pH control. The head pressure was 0.5 bars. The cells were harvested by centrifugation 16 h post IPTG addition.

EXAMPLE 7

Preparation of Heat-Treated Cell Extracts of CE-7 Esterases/Perhydrolases

A cell extract of an *E. coli* transformant expressing perhydrolase from *Thermotoga neapolitana* (KLP18/pSW196) or *Thermotoga maritima* MSB8 (KLP18/pSW207) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma Aldrich catalog #BCA1-KT). The clarified *Thermotoga maritima* MSB8 or *Thermotoga neapolitana* perhydrolase-containing extract was heated for 20 min at 75° C., followed immediately by cooling in an ice/water bath to 5° C. The resulting mixture was centrifuged to remove precipitated protein, and the supernatant collected and assayed for total soluble protein as before. SDS-PAGE of the heat-treated supernatant indicated that the perhydrolase constituted at least ca. 90% of the total soluble protein present in the supernatant.

EXAMPLE 8

Temperature Stability of *T. neapolitana* Perhydrolase/Trehalose Spray-Dried Enzyme Powders A set of ten aqueous mixtures were prepared that contained varying concentrations of the heat-treated cell extract protein of *E. coli* KLP18/pSW196 (≧90% *T. neapolitana* perhydrolase by PAGE), trehalose (Cargill), and, optionally, polysorbate 80 (p80) as surfactant in sodium bicarbonate buffer (50 mM, pH=8.1) (Table 1). These solutions were spray-dried using a Buchi B-290 glass-chamber spray dryer (inlet temperature=170° C., exit temperature=90° C., feed rate=3 mL/min to 10 mL/min) to produce ten spray-dried enzyme powders; the weight percent protein in the powders was determined using the BCA (Bicinchoninic acid) protein assay, and the glass transition temperatures (Tg) of these powders were measured using modulated differential scanning calorimetry (Table 1).

TABLE 1

Composition of protein/excipient solutions used to produce *T. neapolitana* perhydrolase/trehalose spray-dried enzyme powders, and Tg of corresponding powders.

| protein/ excipient solution | trehalose (g/L) | protein (g/L) | excipient/ protein | p80 (g/L) | protein/ excipient powder | wt % protein in protein/excipient powder | Tg of protein/ excipient powder (° C.) |
| --- | --- | --- | --- | --- | --- | --- | --- |
| S1-1 | 52.5 | 35 | 1.5 | 0.25 | P1-2 | 39.2 | 42 |
| S2-1 | 100 | 50 | 2.0 | 0 | P2-2 | 32.5 | 48 |
| S3-1 | 100 | 50 | 2.0 | 0.50 | P3-2 | 33.2 | 40 |
| S4-1 | 50 | 50 | 1.0 | 0 | P4-2 | 45.1 | 40 |
| S5-1 | 50 | 50 | 1.0 | 0.50 | P5-2 | 46.7 | 54 |
| S6-1 | 40 | 20 | 2.0 | 0 | P6-2 | 31.4 | 44 |
| S7-1 | 40 | 20 | 2.0 | 0.50 | P7-2 | 32.5 | 45 |
| S8-1 | 20 | 20 | 1.0 | 0 | P8-2 | 47.8 | 38 |

TABLE 1-continued

Composition of protein/excipient solutions used to produce T. neapolitana perhydrolase/trehalose spray-dried enzyme powders, and Tg of corresponding powders.

| protein/ excipient solution | trehalose (g/L) | protein (g/L) | excipient/ protein | p80 (g/L) | protein/ excipient powder | wt % protein in protein/excipient powder | Tg of protein/ excipient powder (° C.) |
|---|---|---|---|---|---|---|---|
| S9-1 | 20 | 20 | 1.0 | 0.50 | P9-2 | 46.6 | 58 |
| S10-1 | 52.5 | 35 | 1.5 | 0.25 | P10-2 | 37.8 | 21 |

The spray-dried enzyme powders were stored in sealed vials at 40° C. and sampled at one-week intervals, and the samples assayed for the concentration of peracetic acid produced in 5 minutes in reactions containing *T. neapolitana* perhydrolase (50 µg protein/mL), $H_2O_2$ (100 mM), triacetin (100 mM) and TURPINAL® SL (500 ppm) in sodium bicarbonate buffer (50 mM, pH 7.2) at 25° C., and analyzed for production of peracetic acid using a modification of the analytical method reported by Karst et al. (below).

A sample (0.040 mL) of the reaction mixture was removed at a predetermined time (5 min) and immediately mixed with 0.960 mL of 5 mM phosphoric acid in water to terminate the reaction by adjusting the pH of the diluted sample to less than pH 4. The resulting solution was filtered using an ULTRAFREE® MC-filter unit (30,000 Normal Molecular Weight Limit (NMWL), Millipore Corp., Billerica, Mass.; cat #UFC3LKT 00) by centrifugation for 2 min at 12,000 rpm. An aliquot (0.100 mL) of the resulting filtrate was transferred to a 1.5-mL screw cap HPLC vial (Agilent Technologies, Palo Alto, Calif.; #5182-0715) containing 0.300 mL of deionized water, then 0.100 mL of 20 mM MTS (methyl-p-tolyl sulfide) in acetonitrile was added, the vial capped, and the contents briefly mixed prior to a 10 min incubation at ca. 25° C. in the absence of light. To the vial was then added 0.400 mL of acetonitrile and 0.100 mL of a solution of triphenylphosphine (TPP, 40 mM) in acetonitrile, the vial re-capped, and the resulting solution mixed and incubated at ca. 25° C. for 30 min in the absence of light. To the vial was then added 0.100 mL of 10 mM N,N-diethyl-m-toluamide (DEET; HPLC external standard) and the resulting solution analyzed by HPLC for MTSO (methyl-p-tolyl sulfoxide), the stoichiometric oxidation product produced by reaction of MTS with peracetic acid. A control reaction was run in the absence of added extract protein or triacetin to determine the rate of oxidation of MTS in the assay mixture by hydrogen peroxide, for correction of the rate of peracetic acid production for background MTS oxidation. HPLC method: Supelco Discovery C8 column (10-cm×4.0-mm, 5 µm) (cat. #569422-U) with Supelco Supelguard Discovery C8 precolumn (Sigma-Aldrich; catalog #59590-U); 10 microliter injection volume; gradient method with $CH_3CN$ (Sigma-Aldrich; catalog #270717) and deionized water at 1.0 mL/min and ambient temperature.

TABLE 2

HPLC Gradient for analysis of peracetic acid.

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

The perhydrolytic activity of the *T. neapolitana* perhydrolase/trehalose spray-dried powder was stable over eight weeks of storage at 40° C. (Table 2).

TABLE 3

Temperature stability of *T. neapolitana* perhydrolase/trehalose spray-dried enzyme powders during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase/trehalose spray-dried powder (50 µg protein/mL) and TURPINAL ® SL (500 ppm).

| time at 40° C. | PAA (ppm) in 5 minutes | | | | | | | | | |
|---|---|---|---|---|---|---|---|---|---|---|
| | P1-2 | P2-2 | P3-2 | P4-2 | P5-2 | P6-2 | P7-2 | P8-2 | P9-2 | P10-2 |
| initial | 1855 | 1983 | 2075 | 2025 | 1769 | 1891 | 1902 | 1777 | 1880 | 1945 |
| week 1 | 1872 | 2019 | 2060 | 1785 | 1776 | 1887 | 2013 | 1903 | 2046 | 2204 |
| week 2 | 1830 | 1899 | 1870 | 1771 | 1833 | 1930 | 1987 | 1933 | 2146 | 2222 |
| week 3 | 1888 | 1974 | 1887 | 1973 | 1977 | 2223 | 2102 | 1924 | 2080 | 2104 |
| week 4 | 1894 | 1878 | 2035 | 1881 | 1712 | 1918 | 1902 | 1793 | 1720 | 1988 |
| week 5 | 1595 | 1744 | 1706 | 1565 | 1871 | 2052 | 1933 | 1783 | 1908 | 1985 |
| week 6 | 1908 | 1760 | 1538 | 1545 | 1825 | 1864 | 1756 | 1675 | 1659 | 1758 |
| week 7 | 1562 | 1797 | 1614 | 1487 | 1551 | 1774 | 1879 | 1927 | 1866 | 1957 |
| week 8 | 1881 | 1959 | 1792 | 1753 | 1939 | 2123 | 1972 | 1907 | 1902 | 2095 |

EXAMPLE 9

Temperature Stability of *T. neapolitana* Perhydrolase/Trehalose Spray-Dried Enzyme Powders in a Mixture of Enzyme Powder and Triacetin The spray-dried enzyme powders prepared as described in Example 8 were evaluated for stability when stored for eight weeks at 40° C. as a mixture of the spray-dried powder in triacetin. Spray-dried enzyme powders were added to triacetin to produce a mixture containing 0.200 g of protein in 87.2 g of triacetin. The resulting mixtures were stored at 40° C., and a 2.19 g sample of the well-stirred mixture was assayed weekly at 25° C. in a 100-mL reaction containing 100 mM hydrogen peroxide and TURPINAL® SL (500 ppm) in 50 mM sodium bicarbonate buffer at pH 7.2, where the resulting concentration of triacetin and protein was 100 mM and 50 µg/mL, respectively. Comparison of the data in Table 4 with the data in Example 8, Table 3, demonstrates the instability of *T. neapolitana* perhydrolase/trehalose spray-dried enzyme powders when stored as a mixture with triacetin.

TABLE 4

Temperature stability of *T. neapolitana* perhydrolase/trehalose spray-dried enzyme powders during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | P1-2 | P2-2 | P3-2 | P4-2 | P5-2 | P6-2 | P7-2 | P8-2 | P9-2 | P10-2 |
|---|---|---|---|---|---|---|---|---|---|---|
| | PAA (ppm) in 5 minutes | | | | | | | | | |
| initial | 1650 | 1495 | 1539 | 1569 | 1666 | 1735 | 1552 | 1327 | 1712 | 1816 |
| week 1 | 1214 | 1359 | 1597 | 1599 | 1589 | 1632 | 1515 | 1469 | 1421 | 1577 |
| week 2 | 1303 | 1609 | 1580 | 1316 | 1293 | 1682 | 1353 | 971 | 1402 | 1483 |
| week 3 | 1092 | 1573 | 1568 | 1233 | 1293 | 1245 | 1268 | 849 | 1324 | 1388 |
| week 4 | 828 | 1563 | 1420 | 1226 | 1199 | 1608 | 1361 | 961 | 1172 | 1273 |
| week 5 | 622 | 1340 | 1114 | 1294 | 1154 | 1663 | 1163 | 739 | 815 | 667 |
| week 6 | 636 | 1301 | 990 | 970 | 895 | 1318 | 514 | 313 | 699 | 372 |
| week 7 | 281 | 998 | 1140 | 841 | 798 | 962 | 259 | 188 | 831 | 521 |
| week 8 | 254 | 569 | 659 | 563 | 567 | 483 | 414 | 323 | 494 | 321 |

EXAMPLE 10

Temperature Stability of *T. neapolitana* Perhydrolase/Maltodextrin Spray-Dried Enzyme Powder An aqueous mixture was prepared containing heat-treated cell extract protein of *E. coli* KLP18/pSW196 (34 g protein/L, ≧90% *T. neapolitana* perhydrolase by PAGE) and maltodextrin (66.7 g/L MALTRIN® M100 maltodextrin, 14.7 g/L MALTRIN® M250, 14.7 g/L MALTRIN® M040, Grain Processing Corporation, Muscatine, Iowa) as excipient in 50 mM sodium bicarbonate (pH 8.1). This solution was spray-dried using a spray dryer (GEA Niro, 3-ft diameter, inlet temperature=226° C., exit temperature=76° C., feed rate=60 g/min) to produce a spray-dried enzyme powder; the weight percent protein in the powder (20.3 wt %) was determined using the BCA (Bicinchoninic acid) protein assay, and the glass transition temperature of this powder (Tg=54° C.) was measured using modulated differential scanning calorimetry. This solution was spray-dried to produce a powder that was then tested for stability during storage at 40° C. for 9 weeks. The spray-dried enzyme powder (stored at 40° C.) was sampled at one-week intervals and assayed for activity using 50 µg protein/mL of *T. neapolitana* perhydrolase, $H_2O_2$ (100 mM), triacetin (100 mM) and TURPINAL® SL (500 ppm) in 50 mM bicarbonate buffer (pH 7.2) at 25° C., and analyzed for production of peracetic acid using a modification of the analytical method reported by Karst et al., supra. The perhydrolytic activity of the *T. neapolitana* perhydrolase/maltodextrin spray-dried powder was stable over eight weeks of storage at 40° C. (Table 5).

TABLE 5

Temperature stability of *T. neapolitana* perhydrolase/maltodextrin spray-dried enzyme powder during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | PAA (ppm) in 5 min |
|---|---|
| initial | 1142 |
| week 1 | 1117 |

TABLE 5-continued

Temperature stability of *T. neapolitana* perhydrolase/maltodextrin spray-dried enzyme powder during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | PAA (ppm) in 5 min |
|---|---|
| week 2 | 1135 |
| week 3 | 1087 |
| week 4 | 964 |
| week 5 | 1153 |
| week 6 | 930 |
| week 7 | 1025 |
| week 8 | 964 |

EXAMPLE 11

Temperature Stability of *T. neapolitana* Perhydrolase/Maltodextrin Spray-Dried Enzyme Powder Stored in a Mixture of Enzyme Powder and Triacetin The spray-dried enzyme powder prepared as described in Example 10 was evaluated for stability when stored for twenty-one weeks at 40° C. as a mixture of the spray-dried powder in triacetin. The spray-dried enzyme powder (1.235 g, 20.3 wt % protein) was added to 109 g of triacetin. The resulting mixture was stored at 40° C., and a 2.19 g sample of the well-stirred mixture assayed in duplicate at 25° C. in a 100-mL reaction containing hydrogen peroxide (100 mM) and TURPINAL® SL (500 ppm) in 50 mM sodium bicarbonate buffer at pH 7.2, where the resulting concentration of triacetin and protein was 100 mM and 50 μg/mL, respectively. Comparison of the data in Table 6 with the data in Example 10, Table 5, demonstrates the stability of *T. neapolitana* perhydrolase/maltodextrin spray-dried enzyme powders when stored as a mixture with triacetin.

TABLE 6

Temperature stability of *T. neapolitana* perhydrolase/maltodextrin spray-dried enzyme powder during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 μg protein/mL) and TURPINAL ® SL (500 ppm).

| time at 40° C. | PAA (ppm) in 5 min | | |
|---|---|---|---|
| | duplicate A | duplicate B | average |
| initial | 1010 | 1019 | 1015 |
| week 1 | 983 | 1054 | 1019 |
| week 2 | 897 | 927 | 912 |
| week 3 | 1194 | 1137 | 1166 |
| week 4 | 1139 | 1088 | 1114 |
| week 5 | 1099 | 1069 | 1084 |
| week 6 | 1098 | 978 | 1038 |
| week 7 | 1018 | 1006 | 1012 |
| week 8 | 907 | 892 | 900 |
| week 12 | 925 | 936 | 931 |
| week 18 | 824 | ND | |
| week 21 | 792 | ND | |

ND = a duplicate assay was not done

EXAMPLE 12

Temperature Stability of *T. neapolitana* Perhydrolase/Maltodextrin Spray-Dried Enzyme Powder Stored in a Mixture of Enzyme Powder, Sodium Bicarbonate and Triacetin The spray-dried enzyme powder prepared as described in Example 10 was evaluated for stability when stored for 21 weeks at 40° C. as a mixture of the spray-dried powder in a mixture of triacetin and sodium bicarbonate. The spray-dried enzyme powder (0.988 g, 20.3 wt % protein) was added to a mixture of 87.2 g of triacetin and 16.8 g of sodium bicarbonate (Grade 3DF (powder), Church & Dwight). The resulting mixture was stored at 40° C., and a 2.62 g sample of the well-stirred mixture was assayed in duplicate at 25° C. in a 100-mL reaction containing hydrogen peroxide (100 mM) and TURPINAL® SL (500 ppm), where the resulting concentrations of triacetin, sodium bicarbonate and protein were 100 mM, 50 mM (pH 7.2) and 50 μg/mL, respectively. Comparison of the data in Table 7 with the data in Example 11, Table 6, demonstrates the stability of *T. neapolitana* perhydrolase/maltodextrin spray-dried enzyme powders when stored for twenty-one weeks at 40° C. as a mixture with triacetin and solid sodium bicarbonate is improved when compared to the stability of *T. neapolitana* perhydrolase/maltodextrin spray-dried enzyme powders when stored for twenty-one weeks at 40° C. as a mixture with triacetin alone. At the longer storage times, such as 21 weeks, the perhydrolase still retains ca. 100% of initial activity in a mixture of triacetin and sodium bicarbonate.

TABLE 7

Temperature stability of *T. neapolitana* perhydrolase/maltodextrin spray-dried enzyme powder during storage in a mixture of enzyme powder, sodium bicarbonate and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 μg protein/mL) and TURPINAL ® SL (500 ppm).

| time at 40° C. | PAA (ppm) in 5 min | | |
|---|---|---|---|
| | duplicate A | duplicate B | average |
| initial | 950 | 1032 | 991 |
| week 1 | 1060 | 1096 | 1078 |
| week 2 | 1114 | 1114 | 1114 |
| week 4 | 1044 | 974 | 1009 |
| week 8 | 1085 | 1046 | 1066 |
| week 12 | 1101 | 1122 | 1112 |
| week 17 | 1013 | ND | |
| week 21 | 1162 | ND | |

ND = a duplicate assay was not done

EXAMPLE 13

Temperature Stability of *T. maritima* Perhydrolase/Maltodextrin Spray-Dried Enzyme Powder An aqueous mixture was prepared containing heat-treated cell extract protein of *E. coli* KLP18/pSW207 (21 g protein/L, ≧90% *T. maritima* perhydrolase by PAGE) and maltodextrin (31 g/L maltodextrin DE 13-17 and 31 g/L maltodextrin DE 4-7, Aldrich) as excipient in 50 mM sodium bicarbonate (pH 8.1). This solution was spray-dried using a Buchi B-290 glass-chamber spray dryer (inlet temperature=170° C., exit temperature=90° C., feed rate=4.5 mL/min) to produce a spray-dried enzyme powder; the weight percent protein in the powder (18.0 wt %) was determined using the BCA (Bicinchoninic acid) protein assay, and the glass transition temperature of this powder (Tg=90° C.) was measured using modulated differential scanning calorimetry. This solution was spray-dried to produce a powder that was then tested for stability during storage at 40° C. for 7 weeks. The spray-dried enzyme powder (stored at 40° C.) was sampled at one-week intervals and assayed for activity using 50 μg protein/mL of *T. maritima* perhydrolase, $H_2O_2$ ($H_2O_2$ (100 mM)), triacetin (100 mM) and TURPINAL® SL (500 ppm) in 50 mM bicarbonate buffer (pH 7.2) at 25° C., and analyzed for production of peracetic acid using a modification of the analytical method reported by Karst et al., supra. The perhydrolytic activity of the *T. maritima* perhydrolase/maltodextrin spray-dried powder was stable over seven weeks of storage at 40° C. (Table 8).

TABLE 8

Temperature stability of *T. maritima* perhydrolase/maltodextrin spray-dried enzyme powder during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. maritima* perhydrolase (50 μg protein/mL) and TURPINAL ® SL (500 ppm).

| time at 40° C. | PAA (ppm) in 5 min |
|---|---|
| initial | 1373 |
| week 1 | 1262 |
| week 2 | 1548 |
| week 3 | 1317 |

TABLE 8-continued

Temperature stability of *T. maritima* perhydrolase/maltodextrin spray-dried enzyme powder during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. maritima* perhydrolase (50 µg protein/mL) and TURPINAL ® SL (500 ppm).

| time at 40° C. | PAA (ppm) in 5 min |
|---|---|
| week 4 | 1316 |
| week 5 | 1378 |
| week 6 | 1296 |
| week 7 | 1475 |

EXAMPLE 14

Temperature Stability of *T. maritima* Perhydrolase/Maltodextrin Spray-Dried Enzyme Powder Stored in a Mixture of Enzyme Powder and Triacetin The spray-dried enzyme powder prepared as described in Example 13 was evaluated for stability when stored for seven weeks at 40° C. as a mixture of the spray-dried powder in triacetin. The spray-dried enzyme powder (0.556 g, 18.0 wt % protein) was added to 43.6 g of triacetin. The resulting mixture was stored at 40° C., and a 2.21 g sample of the well-stirred mixture assayed in duplicate at 25° C. in a 100-mL reaction containing hydrogen peroxide (100 mM) and TURPINAL® SL (500 ppm) in 50 mM sodium bicarbonate buffer at pH 7.2, where the resulting concentration of triacetin and protein was 100 mM and 50 µg/mL, respectively. Comparison of the data in Table 9 with the data in Example 13, Table 8, demonstrates the stability of *T. maritima* perhydrolase/maltodextrin spray-dried enzyme powders when stored as a mixture with triacetin.

TABLE 9

Temperature stability of *T. maritima* perhydrolase/maltodextrin spray-dried enzyme powder during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. maritima* perhydrolase (50 µg protein/mL) and TURPINAL ® SL (500 ppm).

| time at 40° C. | PAA (ppm) in 5 min |
|---|---|
| initial | 1137 |
| week 1 | 1089 |
| week 2 | 1138 |
| week 3 | 1213 |
| week 4 | 1130 |
| week 5 | 872 |
| week 6 | 858 |
| week 7 | 1004 |

EXAMPLE 15

Temperature Stability of *T. maritima* Perhydrolase/Maltodextrin Spray-Dried Enzyme Powder Stored in a Mixture of Enzyme Powder, Sodium Bicarbonate and Triacetin The spray-dried enzyme powder prepared as described in Example 13 was evaluated for stability when stored for seven weeks at 40° C. as a mixture of the spray-dried powder in a mixture of triacetin and sodium bicarbonate. The spray-dried enzyme powder (0.556 g, 18.0 wt % protein) was added to 43.6 g of triacetin and 8.4 g of sodium bicarbonate (Grade 3DF (powder), Church & Dwight). The resulting mixture was stored at 40° C., and a 2.63 g sample of the well-stirred mixture assayed in duplicate at 25° C. in a 100-mL reaction containing hydrogen peroxide (100 mM) and TURPINAL® SL (500 ppm), where the resulting concentrations of triacetin, sodium bicarbonate buffer (pH 7.2) and protein were 100 mM, 50 mM and 50 µg/mL, respectively. Comparison of the data in Table 10 with the data in Example 14, Table 9, demonstrates the improved stability of *T. maritima* perhydrolase/maltodextrin spray-dried enzyme powders when stored for five, six and seven weeks at 40° C. as a mixture with triacetin and solid sodium bicarbonate when compared to the stability of *T. neapolitana* perhydrolase/maltodextrin spray-dried enzyme powders when stored for five, six and seven weeks at 40° C. as a mixture with triacetin alone.

TABLE 10

Temperature stability of *T. maritima* perhydrolase/maltodextrin spray-dried enzyme powder during storage in a mixture of enzyme powder, sodium bicarbonate and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing T. maritima perhydrolase (50 µg protein/mL) and TURPINAL ® SL (500 ppm).

| time at 40° C. | PAA (ppm) in 5 min |
|---|---|
| initial | 1153 |
| week 1 | 1138 |
| week 2 | 1343 |
| week 3 | 1242 |
| week 4 | 1111 |
| week 5 | 1149 |
| week 6 | 1184 |
| week 7 | 1109 |

EXAMPLE 16

Effect of Added Solvent on Peracetic Acid Production by *Thermotoga neapolitana* Perhydrolase A first mixture of 90.0 g of deionized water, 0.350 g of TURPINAL® SL ((1-hydroxy-1-phosphonoethyl)phosphonic acid, 60 wt % in water; Thermphos International), and 3.20 g of 30 wt % hydrogen peroxide in water was adjusted to pH 7.2 with 50% aqueous sodium hydroxide, and the final weight of the mixture adjusted to 100.0 g with deionized water. A second mixture of 55.76 g triacetin, 4.20 g of sodium bicarbonate, 2.50 g of CAB-O-SIL® M5 (Cabot), 0.270 g of spray-dried *Thermotoga neapolitana* perhydrolase (Example 10), and 37.43 g of one organic solvent selected from the group consisting of tripropylene glycol methyl ether (DOWANOL® TPM), dipropylene glycol methyl ether (DOWANOL® DPM), propylene glycol methyl ether (DOWANOL® PM), Diethylene glycol butyl ether (DOWANOL® DB), dipropylene glycol (DOWANOL® DPG), triethylene glycol, 1,2-propanediol, N-ethyl-2-pyrroldinone, isopropanol, ethanol, ethyl lactate, or 1,3-propanediol was prepared. A 1.0 g aliquot of the second mixture was removed with rapid stirring (to suspend the undissolved solids) and mixed with 9.00 mL of the first mixture of hydrogen peroxide and TURPINAL® SL in water (pH 7.2) was added to with stirring at 25° C.; the resulting mixture contained 255 mM triacetin, 254 mM hydrogen peroxide and 0.055 mg protein/mL of spray-dried perhydrolase. A control reaction for each solvent was also run to determine the concentration of peracetic acid produced by chemical perhydrolysis of triacetin by hydrogen peroxide in the absence of added protein.

Determination of the concentration of peracetic acid in the reaction mixtures was performed according to the method described by Karst et al. Aliquots (0.040 mL) of the reaction mixture were removed at predetermined times and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore cat #UFC3LKT 00) by centrifugation for 2 min at 12,000 rpm. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC as described in Table 2.

HPLC Method:
Supelco Discovery C8 column (10-cm×4.0-mm, 5 μm) (cat. #569422-U) w/precolumn Supelco Supelguard Discovery C8 (Sigma-Aldrich; cat #59590-U); 10 microliter injection volume; gradient method with $CH_3CN$ (Sigma-Aldrich; #270717) and deionized water at 1.0 mL/min and ambient temperature:

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

The peracetic acid concentrations produced in 0.5 min, 1 min, 2 min, 5 min and 10 min for the reactions described above are listed in Table 11, below.

TABLE 11

Dependence of peracetic acid (PAA) concentration on solvent addition using 255 mM triacetin, 254 mM hydrogen peroxide and 0.055 mg/mL of spray-dried *Thermotoga neapolitana* perhydrolase.

| Solvent | Enzyme (μg/mL) | PAA (ppm) 0.5 min | 1 min | 2 min | 5 min | 10 min |
|---|---|---|---|---|---|---|
| DOWANOL® PM | 0 | 39 | 54 | 52 | 81 | 137 |
| DOWANOL® DPM | 0 | 136 | 41 | 106 | 386 | ND |
| DOWANOL® TPM | 0 | 23 | 25 | 111 | 93 | 180 |
| DOWANOL® DB | 0 | 107 | 102 | 105 | 157 | 218 |
| DOWANOL® DPG | 0 | 19 | 40 | 101 | 156 | 207 |
| Triethylene glycol | 0 | 36 | 53 | 110 | 76 | 307 |
| 1,2-propanediol | 0 | 101 | 96 | 122 | 226 | 347 |
| N-ethyl-2-pyrroldinone | 0 | 37 | 49 | 60 | 77 | 133 |
| isopropanol | 0 | 70 | 13 | 147 | 150 | 242 |
| ethanol | 0 | 68 | 33 | 150 | 356 | 479 |
| ethyl lactate | 0 | 88 | 91 | 98 | 121 | 137 |
| 1,3-propanediol | 0 | 54 | 48 | 48 | 62 | 107 |
| DOWANOL® PM | 55 | 355 | 1327 | 1632 | 3156 | 5378 |
| DOWANOL® DPM | 55 | 846 | 972 | 1587 | 3209 | 4494 |
| DOWANOL® TPM | 55 | 439 | 539 | 1303 | 2710 | 3740 |
| DOWANOL® DB | 55 | 475 | 827 | 1719 | 3222 | 4863 |
| DOWANOL® DPG | 55 | 583 | 769 | 1211 | 2784 | 4522 |
| Triethylene glycol | 55 | 325 | 834 | 1634 | 3229 | 5116 |
| 1,2-propanediol | 55 | 507 | 903 | 1428 | 2921 | 4364 |
| N-ethyl-2-pyrroldinone | 55 | 243 | 837 | 1470 | 3033 | 4839 |
| isopropanol | 55 | 326 | 656 | 1175 | 2229 | 2860 |
| ethanol | 55 | 408 | 584 | 1109 | 2235 | 2858 |
| ethyl lactate | 55 | 180 | 337 | 5736 | 1420 | 2554 |
| 1,3-propanediol | 55 | 163 | 269 | 510 | 1086 | 1657 |

To demonstrate the stability of the spray-dried enzyme in a mixture of triacetin and an organic solvent, the mixtures of triacetin, sodium bicarbonate, CAB-O-SIL® M5 (Cabot), spray-dried *Thermotoga neapolitana* perhydrolase (Example 10), and either tripropylene glycol methyl ether (DOWANOL® TPM) or 1,2-propanediol described above were stored for 24 h at ambient temperature, then a 1.0 g aliquot of each of these mixtures was removed with rapid stirring (to suspend the undissolved solids) and mixed with 9.0 mL of a freshly prepared (as described above) mixture of hydrogen peroxide and TURPINAL® SL in water (pH 7.2) with stirring at 25° C.; the resulting mixture contained 255 mM triacetin, 254 mM hydrogen peroxide and 0.055 mg protein/mL of spray-dried perhydrolase. A control reaction for each solvent was also run to determine the concentration of peracetic acid produced by chemical perhydrolysis of triacetin by hydrogen peroxide in the absence of added protein. Determination of the concentration of peracetic acid in the reaction mixtures was performed according to the method described by Karst et al. (Table 12).

TABLE 12

Stability of perhydrolase in triacetin solvent suspension, measured in reactions containing 255 mM triacetin and 254 mM hydrogen peroxide.

| Solvent | Enzyme (μg/mL) | PAA (ppm) 0.5 min | 1 min | 2 min | 5 min | 10 min |
|---|---|---|---|---|---|---|
| DOWANOL® TPM | 0 | 0 | 95 | 58 | 172 | 276 |
| 1,2-propanediol | 0 | 16 | 38 | 35 | 171 | 397 |
| DOWANOL® TPM | 55 | 386 | 557 | 1078 | 2014 | 2717 |
| 1,2-propanediol | 55 | 566 | 768 | 1467 | 3093 | 4649 |

EXAMPLE 16

Comparison of Peracetic Acid Production by *Thermotoga neapolitana* Perhydrolase in Presence or Absence of Added Solvent A first mixture of 40.0 g of deionized water, 0.1575 g of TURPINAL® SL ((1-hydroxy-1-phosphonoethyl)phosphonic acid, 60 wt % in water; Thermphos International), and 1.44 g of 30 wt % hydrogen peroxide in water was adjusted to pH 7.2 with 50% aqueous sodium hydroxide, and the final weight of the mixture adjusted to 46.87 g with deionized water. A second mixture of 2.78 g triacetin, 0.210 g of sodium bicarbonate, 0.125 g of CAB-O-SIL® M5 (Cabot) and 0.0135 g of spray-dried *Thermotoga neapolitana* perhydrolase (Example 10) was prepared, and the first mixture of hydrogen peroxide and TURPINAL® SL in water (pH 7.2) was added to the second mixture with stirring at 25° C.; the resulting mixture contained 255 mM triacetin, 254 mM hydrogen peroxide and 0.055 mg protein/mL of spray-dried perhydrolase. Determination of the concentration of peracetic acid in the reaction mixtures was performed according to the method described by Karst et al., supra. A control reaction was also run to determine the concentration of peracetic acid produced by chemical perhydrolysis of triacetin by hydrogen peroxide in the absence of added perhydrolase.

The reaction described above was repeated, where 1.872 g of either propylene glycol monomethyl ether (DOWANOL® PM) or dipropyleneglycol monomethyl ether (DOWANOL® DPM), was substituted for an equivalent weight of water in the reaction mixture. A first mixture of 40.0 g of deionized water, 0.175 g of TURPINAL® SL, and 1.60 g of 30 wt % hydrogen peroxide in water was adjusted to pH 7.2 with 50% aqueous sodium hydroxide, and the final weight of the mixture adjusted to 50.0 g with deionized water. A second mixture of 2.78 g triacetin, 1.872 g of either propylene glycol monomethyl ether (DOWANOL® PM) or dipropyleneglycol monomethyl ether (DOWANOL® DPM), 0.210 g of sodium bicarbonate, 0.125 g of CAB-O-SIL® M5 (Cabot) and 0.0135 g of spray-dried *Thermotoga neapolitana* perhydrolase (Example 10) was prepared, and 45.0 g of the first mixture of hydrogen peroxide and TURPINAL® SL in water (pH 7.2) was added to the second mixture with stirring at 25° C.; the resulting mixture (pH 6.5) contained 255 mM triacetin, 254 mM hydrogen peroxide and 0.055 mg protein/mL of spray-dried perhydrolase. A control reaction was also run to determine the concentration of peracetic acid produced by chemical perhydrolysis of triacetin by hydrogen peroxide in the absence of added extract protein. The peracetic acid concentrations produced in 0.5 min, 1 min, 2 min, 5 min and 10 min for the three reactions described above are listed in Table 13, below.

TABLE 13

Dependence of peracetic acid (PAA) concentration on solvent addition using 255 mM triacetin, 254 mM hydrogen peroxide and 55 μg/mL of spray-dried *Thermotoga neapolitana* perhydrolase.

| Solvent | Enzyme (μg/mL) | PAA (ppm) | | | | |
|---|---|---|---|---|---|---|
| | | 0.5 min | 1 min | 2 min | 5 min | 10 min |
| none | 0 | ND | ND | ND | ND | ND |
| DOWANOL ® PM | 0 | 89 | 90 | 205 | 318 | 498 |

TABLE 13-continued

Dependence of peracetic acid (PAA) concentration on solvent addition using 255 mM triacetin, 254 mM hydrogen peroxide and 55 μg/mL of spray-dried *Thermotoga neapolitana* perhydrolase.

| Solvent | Enzyme (μg/mL) | PAA (ppm) | | | | |
|---|---|---|---|---|---|---|
| | | 0.5 min | 1 min | 2 min | 5 min | 10 min |
| DOWANOL ® DPM | 0 | 104 | 178 | 184 | 373 | 535 |
| none | 55 | 629 | 1359 | 2020 | 4274 | 6019 |
| DOWANOL ® PM | 55 | 807 | 1390 | 2331 | 4439 | 5917 |
| DOWANOL ® DPM | 55 | 787 | 1373 | 2566 | 5122 | 6528 |

EXAMPLE 17

Use of Solvent for In Situ Peroxycarboxylic Acid Generation Using a Two-Compartment Spray-Bottle Compared to Stirred Reactions A first mixture of 100 g of 0.20 M sodium citrate buffer containing 2000 ppm TURPINAL®SL ((1-hydroxy-1-phosphonoethyl) phosphonic acid, 60 wt % in water; Thermphos International), 280 g of deionized water, and 5.20 g of 30 wt % hydrogen peroxide in water was adjusted to pH 7.2 with 50% aqueous sodium hydroxide, and the final weight of the mixture adjusted to 400 g with deionized water. A second mixture was separately prepared, containing 83.4 g of triacetin, 3.75 g of CAB-O-SIL® M5 (Cabot), 0.750 g of spray-dried *Thermotoga neapolitana* perhydrolase (Example 10), and 62.1 g of a single solvent selected from: propylene glycol methyl ether (DOWANOL® PM), tripropylene glycol methyl ether (DOWANOL® TPM), diethylene glycol methyl ether (DOWANOL® DM), propylene glycol n-butyl ether (DOWANOL® PNB), propylene glycol n-propyl ether (DOWANOL® PnP), propylene glycol monomethyl ether acetate (DOWANOL® PMA), dipropylene glycol, ethanol, isopropanol, and 1,2-propanediol. In a first reaction at 25° C., 1.0 g of the first mixture was stirred with 9.0 g of the second mixture for the first 30-60 seconds of the reaction (reaction pH of 6.5-6.0), and samples were withdrawn and analyzed for peracetic acid production; the resulting reaction mixture contained 255 mM triacetin, 103 mM hydrogen peroxide and 100 μg protein/mL of spray-dried perhydrolase. Determination of the concentration of peracetic acid in the reaction mixtures (TABLE 14, below) was performed according to the method described by Karst et al., supra. A control reaction was also run to determine the concentration of peracetic acid produced by chemical perhydrolysis of triacetin by hydrogen peroxide in the absence of added perhydrolase.

The first mixture and second mixture prepared as described above were each separately charged to one of the two compartments of a two-compartment spray bottle (Custom Dual-Liquid Variable-Ratio Sprayer, Model DLS 200, manufactured by Take5 (Rogue River, Oreg.)), where the bottle was set up to spray a mixture of 9 parts by weight of the first mixture with 1 part by weight of the second mixture. The two mixtures were sprayed into a 12.5 cm diameter crystallizing dish, and the resulting reaction mixture (reaction pH of 6.5-6.0) contained 255 mM triacetin, 100 mM hydrogen peroxide and 0.100 mg protein/mL of spray-dried perhydrolase. The sprayed reaction mixture was sampled at predetermined times and analyzed for peracetic acid (TABLE 14, below) according to the method described by Karst et al., supra.

TABLE 14

Dependence of peracetic acid (PAA) concentration on solvent addition using 255 mM triacetin, 103 mM hydrogen peroxide and 100 μg/mL of spray-dried *Thermotoga neapolitana* perhydrolase in stirred batch reactions and in a sprayed two-component mixture.

| Solvent | Enzyme (μg/mL) | PAA (ppm) | | | | | |
| --- | --- | --- | --- | --- | --- | --- | --- |
| | | 20 sec | 40 sec | 60 sec | 120 sec | 300 sec | 600 sec |
| DOWANOL ® PM, stirred reaction | 0 | 101 | 106 | 106 | 82 | 90 | 166 |
| DOWANOL ® PM, stirred reaction | 100 | 319 | 587 | 622 | 648 | 889 | 976 |
| DOWANOL ® PM, sprayed reaction | 100 | 375 | 454 | 515 | 671 | 873 | 994 |
| DOWANOL ® TPM, stirred reaction | 0 | 0 | 72 | 19 | 25 | 44 | 69 |
| DOWANOL ® TPM, stirred reaction | 100 | 445 | 548 | 726 | 980 | 1378 | 1560 |
| DOWANOL ® TPM, sprayed reaction | 100 | 433 | 575 | 1385 | 806 | 1089 | 1250 |
| DOWANOL ® DM, stirred reaction | 0 | 287 | 261 | 287 | 261 | 255 | 234 |
| DOWANOL ® DM, stirred reaction | 100 | 667 | 875 | 927 | 1410 | 1640 | 1876 |
| DOWANOL ® DM, sprayed reaction | 100 | 540 | 613 | 866 | 914 | 1112 | 1276 |
| DOWANOL ® PNB, stirred reaction | 0 | 76 | 70 | 40 | 58 | 0 | 11 |
| DOWANOL ® PNB, stirred reaction | 100 | 344 | 488 | 654 | 932 | 1166 | 1357 |
| DOWANOL ® PNB, sprayed reaction | 100 | 394 | 514 | 586 | 715 | 963 | 1141 |
| DOWANOL ® PnP, stirred reaction | 0 | 173 | 163 | 223 | 215 | 213 | 253 |
| DOWANOL ® PnP, stirred reaction | 100 | 611 | 716 | 857 | 1277 | 1468 | 1516 |
| DOWANOL ® PnP, sprayed reaction | 100 | 371 | 657 | 737 | 928 | 1090 | 1195 |
| DOWANOL ® PMA, stirred reaction | 0 | 0 | 0 | 14 | 0 | 128 | 166 |
| DOWANOL ® PMA, stirred reaction | 100 | 335 | 510 | 756 | 1218 | 2178 | 3132 |
| DOWANOL ® PMA, sprayed reaction | 100 | 541 | 745 | 1042 | 1472 | ND | 3236 |
| dipropylene glycol, stirred reaction | 0 | 26 | 54 | 73 | 79 | 40 | 38 |
| dipropylene glycol, stirred reaction | 100 | 318 | 539 | 708 | 1423 | 1241 | 946 |
| dipropylene glycol, sprayed reaction | 100 | 371 | 414 | 464 | 618 | 756 | 863 |
| ethanol, stirred reaction | 0 | 144 | 184 | 152 | 161 | 167 | 170 |
| ethanol, stirred reaction | 100 | 398 | 553 | 694 | 919 | 1227 | 1311 |
| ethanol, sprayed reaction | 100 | 504 | 677 | 685 | 766 | 968 | 1125 |
| isopropanol, stirred reaction | 0 | 149 | 167 | 180 | 207 | 180 | 236 |
| isopropanol, stirred reaction | 100 | 564 | 691 | 783 | 1114 | 1395 | 1533 |
| isopropanol, sprayed reaction | 100 | 621 | 767 | 882 | 1014 | 1239 | 1435 |
| 1,2-propanediol, stirred reaction | 0 | 32 | 14 | 19 | 33 | ND | 108 |
| 1,2-propanediol, stirred reaction | 100 | 427 | 665 | 921 | 1485 | 1941 | 3466 |
| 1,2-propanediol, sprayed reaction | 100 | 376 | 554 | 704 | 1376 | 1873 | 2517 |
| cyclohexanone, stirred reaction | 0 | 136 | 133 | 153 | 138 | 152 | 114 |
| cyclohexanone, stirred reaction | 100 | 97 | 153 | 185 | 351 | 329 | 459 |
| cyclohexanone, sprayed reaction | 100 | 128 | 196 | 338 | 368 | 416 | 489 |

EXAMPLE 18

Peroxycarboxylic Acid Production Using *Thermotoga maritima* Perhydrolase as an Enzyme Catalyst Cloning and expression of perhydrolase from *Thermotoga maritima* is accomplished in accordance with the methods described in Examples 1-3 and 5. Fermentation of bacterial transformants expressing *Thermotoga maritima* perhydrolase is performed in accordance with preceding Example 6, and preparation of spray-dried *Thermotoga maritima* perhydrolase is accomplished using methods described in Example 13. Additional information regarding techniques for cloning, expressing, and preparation of *Thermotoga maritima* perhydrolase is available in U.S. Ser. No. 12/143,375, filed Jun. 20, 2008.

A comparison of peracetic acid production by *Thermotoga maritima* perhydrolase in the presence and absence of added solvent is performed. A first mixture of 40.0 g of deionized water, 0.1575 g of TURPINAL® SL ((1-hydroxy-1-phosphonoethyl)phosphonic acid, 60 wt % in water; Thermphos International), and 1.44 g of 30 wt % hydrogen peroxide in water is adjusted to pH 7.2 with 50% aqueous sodium hydroxide, and the final weight of the mixture adjusted to 46.87 g with deionized water. A second mixture of 2.78 g triacetin, 0210 g of sodium bicarbonate, 0.125 g of CAB-O-SIL® M5 (Cabot) and 0.0135 g of spray-dried *Thermotoga maritima* perhydrolase is prepared, and the first mixture of hydrogen peroxide and TURPINAL® SL in water (pH 7.2) is added to the second mixture with stirring at 25° C.; the resulting mixture containing 255 mM triacetin, 254 mM hydrogen peroxide and 0.055 mg protein/mL of spray-dried perhydrolase. Determination of the concentration of peracetic acid in the reaction mixtures is performed according to the method described by Karst et al., supra. A control reaction is also run to determine the concentration of peracetic acid produced by chemical perhydrolysis of triacetin by hydrogen peroxide in the absence of added perhydrolase.

The reaction described above is repeated, where 1.872 g of either propylene glycol monomethyl ether (DOWANOL® PM) or dipropyleneglycol monomethyl ether (DOWANOL® DPM), is substituted for an equivalent weight of water in the reaction mixture. A first mixture of 40.0 g of deionized water, 0.175 g of TURPINAL® SL, and 1.60 g of 30 wt % hydrogen peroxide in water is adjusted to pH 7.2 with 50% aqueous sodium hydroxide, and the final weight of the mixture adjusted to 50.0 g with deionized water. A second mixture of 2.78 g triacetin, 1.872 g of either propylene glycol monomethyl ether (DOWANOL® PM) or dipropyleneglycol monomethyl ether (DOWANOL® DPM), 0.210 g of sodium bicarbonate, 0.125 g of CAB-O-SIL® M5 (Cabot) and 0.0135 g of spray-dried *Thermotoga maritima* perhydrolase is prepared, and 45.0 g of the first mixture of hydrogen peroxide and TURPINAL® SL in water (pH 7.2) is added to the second mixture with stirring at 25° C.; the resulting mixture (pH 6.5) contained 255 mM triacetin, 254 mM hydrogen peroxide and 0.055 mg protein/mL of spray-dried perhydrolase. A control reaction is also run to determine the concentration of peracetic acid produced by chemical perhydrolysis of triacetin by hydrogen peroxide in the absence of added extract protein. The peracetic acid concentrations produced in 0.5 min, 1 min, 2 min, 5 min and 10 min for the three reactions described above are measured and recorded.

EXAMPLE 19

Use of Solvent for in Situ Peroxycarboxylic Acid Generation Using Two-Compartment Spray Device Compared to Stirred Reaction and Using *Thermotoga maritima* Perhydrolase A first mixture of 100 g of 0.20 M sodium citrate buffer containing 2000 ppm TURPINAL® SL ((1-hydroxy-1-phosphonoethyl)phosphonic acid, 60 wt % in water; Thermphos International), 280 g of deionized water, and 5.20 g of 30 wt % hydrogen peroxide in water is adjusted to pH 7.2 with 50% aqueous sodium hydroxide, and the final weight of the mixture adjusted to 400 g with deionized water. A second mixture is separately prepared, containing 83.4 g of triacetin, 3.75 g of CAB-O-SIL® M5 (Cabot), 0.750 g of spray-dried *Thermotoga maritima* perhydrolase (Example 13), and 62.1 g of a single solvent selected from: propylene glycol methyl ether (DOWANOL® PM), tripropylene glycol methyl ether (DOWANOL® TPM), diethylene glycol methyl ether (DOWANOL® DM), propylene glycol n-butyl ether (DOWANOL® PNB), propylene glycol n-propyl ether (DOWANOL® PnP), propylene glycol monomethyl ether acetate (DOWANOL® PMA), dipropylene glycol, ethanol, isopropanol, and 1,2-propanediol. In a first reaction at 25° C., 1.0 g of the first mixture is stirred with 9.0 g of the second mixture for the first 30-60 seconds of the reaction (reaction pH of 6.5-6.0), and samples are withdrawn and analyzed for peracetic acid production; the resulting reaction mixture containing 255 mM triacetin, 103 mM hydrogen peroxide and 100 µg protein/mL of spray-dried perhydrolase. Determination of the concentration of peracetic acid in the reaction mixtures is performed according to the method described by Karst et al., supra. A control reaction is also run to determine the concentration of peracetic acid produced by chemical perhydrolysis of triacetin by hydrogen peroxide in the absence of added perhydrolase.

The first mixture and second mixture prepared as described above are each separately charged to one of the two compartments of a two-compartment spray bottle (Custom Dual-Liquid Variable-Ratio Sprayer, Model DLS 200, manufactured by Take5 (Rogue River, Oreg.)), where the bottle is set up to spray a mixture of 9 parts by weight of the first mixture with 1 part by weight of the second mixture. The two mixtures are sprayed into a 12.5 cm diameter crystallizing dish, and the resulting reaction mixture (reaction pH of 6.5-6.0) containing 255 mM triacetin, 100 mM hydrogen peroxide and 0.100 mg protein/mL of spray-dried perhydrolase. The sprayed reaction mixture is sampled at predetermined times and analyzed for peracetic acid according to the method described by Karst et al., supra.

EXAMPLE 20

Exemplary Two-Component System

One example of a two-component in situ peroxycarboxylic acid disinfectant formulation is described below.

|  | mol/L | grams |
|---|---|---|
| Component A | | |
| triacetin | 0.100 | 21.82 |
| *T. neapolitana* perhydrolase/excipient |  | 0.20 |
| sodium bicarbonate | 0.050 | 4.20 |

| | mol/L | grams |
|---|---|---|
| Component B | | |
| H$_2$O$_2$ (30 wt %): | 0.100 | 11.33 |
| TURPINAL ® SL (60 wt %, 0.1% final) | | 1.67 |
| water (deionized) | | 960.78 |
| Total weight (grams) | | 1000.00 |

For the two-component in situ peroxycarboxylic acid disinfectant formulation described above, Component A comprises ca. 2.6 wt % of the combined weight of Components A and B, and the weight ratio of Component B to Component A is ca. 38:1. In certain applications for a two-component in-situ peroxycarboxylic acid disinfectant formulation, it may be desirable for the ratio of Component B to Component A to be within a range of from 1:1 to 10:1, where from 10 parts to 1 part (by weight) of Component B is mixed with one part (by weight) of Component A to produce a peroxycarboxylic acid at a concentration efficacious for disinfection. For example, in a first application a two-compartment spray bottle such as a dual-liquid fixed ratio sprayer (Model DLS100, Take5) or a dual-liquid variable ratio sprayer (Model DLS200, Take5) is utilized, where a maximum ratio of Component B to Component A of 10:1 is employed. In a second application, a single bottle containing two separate compartments separated by a breakable seal is employed, where the ratio of the volume of the two separate compartments is 1:1, or 5:1 or 10:1. In each of these applications, the two-component formulation cannot be mixed at the desired ratio of Component A to Component B to provide the desired concentration of reactants and final concentration of products.

EXAMPLE 21

Perhydrolase Activity Assay of *Thermotoga neapolitana* Acetyl Xylan Esterase Variants Libraries of *Thermotoga neapolitana* mutants were prepared as described in Example 4 of co-owned, co-filed, and copending U.S. patent application having attorney docket number CL4392 US NA entitled "improved Perhydrolases for Enzymatic Peracid Production". Briefly, saturation mutagenesis was conducted at amino acid residues F213, I276, C277, and N93 of SEQ ID NO: 6 so that each of the other 19 possible amino acids were individually introduced to each specified position.

The mutations were made using QUIKCHANGE® (Stratagene, La Jolla, Calif.) kit according to the manufacturer's instructions. Amplified plasmids were treated with 1 U of DpnI at 37° C. for 1 hour. Treated plasmids were used to transform chemically competent *E. coli* XL1-Blue (Stratagene) (residues 213, 276 and 277) or chemically competent *E. coli* TOP10F' (invitrogen, Carlsbad, Calif.) (residue 93). Transformants were plated on LB-agar supplemented with 0.1 mg ampicillin/mL and grown overnight at 37° C. Up to five individual colonies were picked and the plasmid DNA sequenced to confirm the expected mutations.

Individual colonies of mutants were picked into 96-well plates containing 0.1 mL LB with 0.1 mg ampicillin/mL, and grown overnight at 37° C. without shaking. 0.003 mL of overnight culture was transferred to an "Induction plate" (96 deep-well) containing 0.3 mL LB, 0.5 mM IPTG and 0.1 mg ampicillin/mL. Induction plates were grown overnight at 37° C. with shaking. 0.01 mL of Induction culture was transferred to "Lysis plate" (96-well) containing 0.09 mL of 56 mg/mL CELYTTIC™ Express (Sigma Aldrich, St. Louis, Mo.). Plates were slightly agitated first, before incubating at 25° C. for 30 minutes. Approximately 0.01 mL of Lysis culture was transferred to "Assay plate" (96-well) containing 0.09 mL "Assay solution pH 5.0" (100 mM triacetin, 100 mM hydrogen peroxide, 50 mM acetic acid pH 5.0). Approximately 0.01 mL of Lysis culture was also transferred to "Assay plate pH 7.5" (96-well) containing 0.09 mL "Assay solution pH 7.5" (100 mM triacetin, 100 mM hydrogen peroxide, 50 mM sodium phosphate pH 7.5). Plates were gently agitated for 30 seconds before incubating at ambient temperature for 10 minutes. The assay was quenched by addition of 0.1 mL of "Stop buffer" (100 mM ortho-phenylenediamine (OPD), 500 mM NaH$_2$PO$_4$ pH 2.0). Plates were gently agitated for 30 seconds before incubating at 25° C. for 30 minutes. The absorbance was read at 458 nm without a lid using a SPECTRAMAX® Plus384 plus (Molecular Devices, Sunnyvale, Calif.). Analysis of the results indicated four variants that demonstrated significantly greater perhydrolase activity compared to the native enzyme (Tables 15 and 16). All four are changes of the cysteine at residue 277 (C277A, C277V, C277S, and C277T; see SEQ ID NO: 19).

TABLE 15

Perhydrolase activity (U/mL) at pH 5.0 of *T. neapolitana* acetyl xylan esterase variants.

| Variant | U/mL | Variant | U/mL | Variant | U/mL | Variant | U/mL |
|---|---|---|---|---|---|---|---|
| F213S | 0.17 | I276W | 0.18 | C277N | 0.17 | N093R | 0.11 |
| F213N | 0.18 | I276R | 0.18 | C277I | 0.17 | N093I | 0.10 |
| F213G | 0.17 | I276L | 0.18 | C277S | 0.43 | N093Q | 0.10 |
| F213C | 0.21 | I276K | 0.18 | C277A | 0.51 | N093K | 0.11 |
| F213V | 0.17 | I276M | 0.18 | C277Q | 0.17 | N093M | 0.10 |
| F213M | 0.17 | I276V | 0.26 | C277L | 0.17 | N093C | 0.12 |
| F213T | 0.17 | I276S | 0.17 | C277K | 0.17 | N093D | 0.10 |
| F213Y | 0.23 | I276N | 0.18 | C277V | 0.35 | N093S | 0.12 |
| F213I | 0.18 | I276C | 0.29 | C277E | 0.17 | N093G | 0.11 |
| F213Q | 0.17 | I276Q | 0.17 | C277P | 0.17 | N093V | 0.10 |
| F213H | 0.22 | I276F | 0.27 | C277D | 0.17 | N093L | 0.13 |
| F213R | 0.20 | I276H | 0.18 | C277M | 0.17 | N09E | 0.10 |
| F213W | 0.17 | I276D | 0.17 | C277F | 0.17 | N093F | 0.10 |
| F213P | 0.17 | I276E | 0.18 | C277T | 0.33 | N09A | 0.11 |
| F213D | 0.17 | I276G | 0.17 | C277Y | 0.17 | N093H | 0.11 |
| F213K | 0.17 | I276Y | 0.23 | C277H | 0.17 | N093W | 0.10 |
| F213L | 0.18 | I276T | 0.29 | C277W | N/A | N093P | 0.10 |
| F213E | N/A | I276A | N/A | C277R | N/A | N093Y | 0.10 |
| F213A | N/A | I276P | N/A | C277G | N/A | N093T | N/A |
| | | | | | | native | 0.16 |

TABLE 16

Perhydrolase activity at pH 7.5 of *T. neapolitana* acetyl xylan esterase variants.

| Variant | U/mL | Variant | U/mL | Variant | U/mL | Variant | U/mL |
|---|---|---|---|---|---|---|---|
| F213S | 1.80 | I276W | 2.00 | C277N | 3.50 | N093R | 0.13 |
| F213N | 1.90 | I276R | 1.90 | C277I | 3.60 | N093I | 0.10 |
| F213G | 1.70 | I276L | 2.00 | C277S | 9.30 | N093Q | 0.11 |
| F213C | 3.00 | I276K | 1.90 | C277A | 7.50 | N093K | 0.13 |
| F213V | 1.70 | I276M | 1.90 | C277Q | 3.50 | N093M | 0.12 |
| F213M | 1.90 | I276V | 3.40 | C277L | 3.60 | N093C | 0.15 |
| F213T | 1.80 | I276S | 1.90 | C277K | 3.50 | N093D | 0.10 |
| F213Y | 2.60 | I276N | 2.10 | C277V | 6.10 | N093S | 0.23 |
| F213I | 1.80 | I276C | 3.40 | C277E | 3.50 | N093G | 0.18 |
| F213Q | 1.80 | I276Q | 2.00 | C277P | 3.60 | N093V | 0.10 |
| F213H | 2.30 | I276F | 2.70 | C277D | 3.70 | N093L | 0.22 |
| F213R | 2.20 | I276H | 2.10 | C277M | 3.60 | N09E | 0.12 |
| F213W | 1.80 | I276D | 1.90 | C277F | 3.60 | N093F | 0.10 |
| F213P | 3.50 | I276E | 1.90 | C277T | 9.60 | N09A | 0.13 |
| F213D | 3.60 | I276G | 3.60 | C277Y | 3.60 | N093H | 0.18 |

TABLE 16-continued

Perhydrolase activity at pH 7.5 of T. neapolitana acetyl xylan esterase variants.

| Variant | U/mL | Variant | U/mL | Variant | U/mL | Variant | U/mL |
|---------|------|---------|------|---------|------|---------|------|
| F213K | 3.60 | I276Y | 4.40 | C277H | 3.60 | N093W | 0.16 |
| F213L | 5.00 | I276T | 3.00 | C277W | N/A | N093P | 0.12 |
| F213E | N/A | I276A | N/A | C277R | N/A | N093Y | 0.15 |
| F213A | N/A | I276P | N/A | C277G | N/A | N093T | N/A |
|  |  |  |  |  |  | native | 0.23 |

EXAMPLE 22

Expression of *Thermotoga neapolitana* Acetyl Xylan Esterase Variants in *E. coli* KLP18

Plasmids with confirmed acetyl xylan esterase mutations were used to transform *E. coli* KLP18 (Example 3). Transformants were plated onto LB-ampicillin (100 µg/mL) plates and incubated overnight at 37° C. Cells were harvested from a plate using 2.5 mL LB media supplemented with 20% (v/v) glycerol, and 1.0 mL aliquots of the resulting cell suspension frozen at −80° C. One mL of the thawed cell suspension was transferred to a 1-L APPLIKON® Bioreactor (Applikon® Biotechnology, Foster City, Calif.) with 0.7 L medium containing $KH_2PO_4$ (5.0 g/L), $FeSO_4$ heptahydrate (0.05 g/L), $MgSO_4$ heptahydrate (1.0 g/L), sodium citrate dihydrate (1.90 g/L), yeast extract (Amberex 695, 5.0 g/L), Biospumex153K antifoam (0.25 mL/L, Cognis Corporation), NaCl (1.0 g/L), $CaCl_2$ dihydrate (0.1 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 6.5 g) and ampicillin (25 mg/mL) stock solution (2.8 mL). Glucose solution (50% w/w) was also used for fed batch. Glucose feed was initiated 40 min after glucose concentration decreased below 0.5 g/L, starting at 0.03 g feed/min and increasing progressively each hour to 0.04, 0.04, 0.05, 0.06, 0.07, 0.08, 0.09, 0.12, and 0.14 g/min respectively; the rate remaining constant afterwards. Glucose concentration in the medium was monitored, and if the concentration exceeded 0.1 g/L the feed rate was decreased or stopped temporarily. Induction was initiated at $OD_{550}$=50 with addition of 0.8 mL IPTG (0.05 M). The dissolved oxygen (DO) concentration was controlled at 25% of air saturation, first by agitation (400-1000 rpm), and following by aeration (0.5-2 slpm). The temperature was controlled at 37° C., and the pH was controlled at 6.8; $NH_4OH$ (29% w/w) and $H_2SO_4$ (20% w/v) were used for pH control. The cells were harvested by centrifugation (5,000×g for 15 minutes) at 20 h post IPTG addition.

EXAMPLE 23

Preparation of Cell Lysates Containing Semi-Purified *T. neapolitana* Acetyl Xylan Esterase or *T. neapolitana* Variant Acetyl Xylan Esterases A cell culture of *E. coli* KLP18/pSW196 (*Thermotoga neapolitana* wild-type perhydrolase) was grown as described in Example 6. The resulting cell paste was resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the heat-treated extract supernatant.

Cell cultures of *E. coli* KLP18/pSW196/C277S (*Thermotoga neapolitana* C277S variant perhydrolase), *E. coli* KLP18/pSW196/C277V (*Thermotoga neapolitana* C277V variant perhydrolase), *E. coli* KLP18/pSW196/C277A (*Thermotoga neapolitana* C277A variant perhydrolase), and *E. coli* KLP18/pSW196/C277T (*Thermotoga neapolitana* C277T variant perhydrolase) were each grown as described in Example 22. The resulting cell pastes were resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the heat-treated extract supernatant.

EXAMPLE 24

Specific Activity and Perhydrolysis/Hydrolysis ratio of *T. neapolitana* Acetyl Xylan Wild-type Esterase and C277 Esterase Variants Reactions (40 mL total volume) were run at 25° C. in phosphate buffer (50 mM, pH 7.2) containing triacetin (100 mM), hydrogen peroxide (100 mM) and one of the following acetyl xylan esterase mutants: *T. neapolitana* C277S variant perhydrolase (0.010 mg/mL of heat-treated extract total protein from *E. coli* KLP18/pSW196/C277S), *T. neapolitana* C277T variant perhydrolase (0.010 mg/mL of heat-treated extract total protein from *E. coli* KLP18/pSW196/C277T), *T. neapolitana* C277A variant perhydrolase (0.0125 mg/mL of heat-treated extract total protein from *E. coli* KLP18/pSW196/C277A), and *T. neapolitana* C277V variant perhydrolase (0.0125 mg/mL of heat-treated extract total protein from *E. coli* KLP18/pSW196/C277V) (prepared as described in Example 23). Reactions were stirred for only the first 30 seconds of reaction to initially mix the reactants and enzyme.

A reaction was also run under identical conditions to that described immediately above using 0.050 mg/mL of heat-treated extract total protein isolated from *E. coli* KLP18/pSW196 (expressing *Thermotoga neapolitana* wild-type acetyl xylan esterase (Example 1)), where the heat-treated extract supernatant was prepared according to the procedure of Example 23.

Two samples from each of the reaction mixtures described above were simultaneously withdrawn after the first minute of each reaction, and every two minutes thereafter for fifteen minutes, where one of the two samples was analyzed for peracetic acid, and the second sample was analyzed for total acetic acid produced from both enzymatic hydrolysis of triacetin and from subsequent conversion of peracetic acid in sample to acetic acid by reaction with methyl-p-tolyl sulfide (MTS, see below).

Measurement of the rate of peracetic acid production in the reaction mixture was performed using a modification of the method described by Karst et al., supra. A sample (0.040 mL) of the reaction mixture was removed at a predetermined time and immediately mixed with 0.960 mL of 5 mM phosphoric acid in water to terminate the reaction by adjusting the pH of the diluted sample to less than pH 4. The resulting solution was filtered using an ULTRAFREE® MC-filter unit (30,000 Normal Molecular Weight Limit (NMWL), Millipore Corp., Billerica, Mass.; cat #UFC3LKT 00) by centrifugation for 2 min at 12,000 rpm. An aliquot (0.100 mL) of the resulting filtrate was transferred to a 1.5-mL screw cap HPLC vial (Agilent Technologies, Palo Alto, Calif.; #5182-0715) containing 0.300 mL of deionized water, then 0.100 mL of 20 mM MTS (methyl-p-tolyl sulfide) in acetonitrile was added, the vial capped, and the contents briefly mixed prior to a 10 min incubation at ca. 25° C. in the absence of light. To the vial was then added 0.400 mL of acetonitrile and 0.100 mL of a solution of triphenylphosphine (TPP, 40 mM) in acetonitrile, the vial re-capped, and the resulting solution mixed and incubated at ca. 25° C. for 30 min in the absence of light. To the vial was then added 0.100 mL of 10 mM N,N-diethyl-m-toluamide (DEET; HPLC external standard) and the resulting solution analyzed by HPLC for MTSO (methyl-p-tolyl sulfoxide), the stoichiometric oxidation product produced by reaction of MTS with peracetic acid. A control reaction was run in the absence of added extract protein or triacetin to determine the rate of oxidation of MTS in the assay mixture by hydrogen peroxide, for correction of the rate of peracetic acid production for background MTS oxidation. HPLC method: Supelco Discovery C8 column (10-cm×4.0-mm, 5 µm) (catalog #569422-U) with Supelco Supelguard Discovery C8 precolumn (Sigma-Aldrich; catalog #59590-U); 10 microliter injection volume; gradient method with $CH_3CN$ (Sigma-Aldrich; catalog #270717) and deionized water at 1.0 mL/min and ambient temperature (Table 17).

TABLE 17

HPLC Gradient for analysis of peracetic acid.

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

For determination of the rate of perhydrolase-catalyzed acetic acid production in the reaction, a sample (0.900 mL) of the reaction mixture was removed at a predetermined time and immediately added to a 1.5 mL-microcentrifuge tube containing 0.040 mL of 0.75 M $H_3PO_4$, and the resulting solution briefly mixed to terminate the reaction at pH 3.0-4.0. To the tube was then added 0.020 mL of a solution of 10 mg/mL of *Aspergillus niger* catalase (Sigma-Aldrich; C3515) in 50 mM phosphate buffer pH (7.2), and the resulting solution mixed and allowed to react for 15 minutes at ambient temperature to disproportionate unreacted hydrogen peroxide to water and oxygen. To the tube was then added 0.040 mL of 0.75 M $H_3PO_4$ and the resulting solution mixed and filtered using an ULTRAFREE® MC-filter unit (30,000 Normal Molecular Weight Limit (NMWL), Millipore Corp., cat #UFC3LKT 00) by centrifugation for 2 min at 12,000 rpm. An aliquot (0.100 mL) of the resulting filtrate was mixed with 0.150 mL of 20 mM MTS (methyl-p-tolyl sulfide) in acetonitrile, and the resulting solution was incubated for 10 min at ca. 25° C. in the absence of light. The concentration of acetic acid in the sample produced by both enzymatic hydrolysis of triacetin and conversion of peracetic acid to acetic acid by reaction with MTS was determined using a gas chromatograph (GC) equipped with a flame ionization detector (FID) and a DB-FFAP column (length, 15 m; ID, 0.530 mm; film thickness, 1.00 µm); a fresh injection port liner was employed for each rate determination (total of eight sample analyses) to avoid build up of phosphoric acid in the injection port liner over time.

The *Thermotoga neapolitana* acetyl xylan esterase variants had a significantly-higher specific activity for perhydrolysis of triacetin than the wild-type esterase (Table 18). The perhydrolysis/hydrolysis ratios for the *T. neapolitana* acetyl xylan esterase variants were determined by dividing the rate of PAA production (perhydrolysis rate) by the rate of hydrolysis of triacetin to acetic acid (hydrolysis rate) (calculated from the rate of total acetic acid production in the assay method from both PAA and acetic acid, and corrected for the rate of peracetic acid production); the P/H ratio of the *T. neapolitana* acetyl xylan esterase variants were ca. equal to or greater than the P/H ratio for the *T. neapolitana* wild-type acetyl xylan esterase (Table 18).

TABLE 18

| *Thermotoga neapolitana* perhydrolase | enzyme concen. (µg/mL) | perhydrolysis rate (mM/min) | hydrolysis rate (mM/min) | P/H ratio | specific activity (U/mg protein) |
|---|---|---|---|---|---|
| wild type | 50 | 3.61 | 1.22 | 3.0 | 72 |
| C277S | 10 | 4.40 | 1.61 | 2.7 | 440 |
| C277T | 10 | 4.24 | 0.81 | 5.2 | 424 |
| C277A | 12.5 | 4.14 | 1.43 | 2.9 | 331 |
| C277V | 12.5 | 3.70 | 0.88 | 4.2 | 296 |

EXAMPLE 25

Cloning and Expression of Acetyl Xylan Esterase from *Thermotoga maritima*

A gene encoding acetyl xylan esterase from *T. maritima* as reported in GENBANK® (accession # NP_227893.1) was synthesized (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO: 52 and SEQ ID NO: 53. The resulting nucleic acid product (SEQ ID NO: 54) was cut with restriction enzymes PstI and XbaI and subcloned between the PstI and XbaI sites in pUC19 to generate the plasmid identified as pSW207. A gene encoding an acetyl xylan esterase from *T. maritima* MSB8 as reported in GENBANK® (Accession no. NP_227893.1) was synthesized using codons optimized for expression in *E. coli* (DNA 2.0, Menlo Park Calif.). The gene was subsequently amplified by PCR (0.5 min at 94° C., 0.5 min at 55° C., 1 min at 70° C., 30 cycles) using primers identified as SEQ ID NO:55 and SEQ ID NO:56. The resulting nucleic acid product was cut with restriction enzymes EcoRI and PstI and subcloned between the EcoRI and PstI sites in pTrc99A (GENBANK® Accession no. M22744) to generate the plasmid identified as pSW228 (containing the codon-optimized *T. maritima* coding sequence SEQ ID NO: 57). The plasmids pSW207 and pSW228 were used to transform *E. coli* KLP18 (U.S. Patent Application Pub. No. 2008/0176299) to generate the strain identified as KLP18/pSW207 and KLP18/pSW228, respectively. KLP18/pSW207 and KLP18/pSW228 were gown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

EXAMPLE 26

Construction of *Thermotoga maritima* Acetyl Xylan Esterase Variants at Residue C277

The C277 (Cys277) position of *T. maritima* acetyl xylan esterase was changed to each of Val, Ala, Ser and Thr using oligonucleotide primer pairs (Table 19) that were designed based on the codon optimized sequence of *T. maritima* acetyl xylan esterase (SEQ ID NO:57) in the plasmid pSW228. The mutations were made using QUIKCHANGE® (Stratagene) according to the manufacturers instructions. Amplified plasmids were treated with 1 U of DpnI at 37° C. for 1 hour. Treated plasmids were used to transform chemically competent *E. coli* XL1-Blue (Stratagene). Transformants were plated on LB-agar supplemented with 0.1 mg ampicillin/mL and grown overnight at 37° C. Up to five individual colonies were picked and the plasmid DNA sequenced to confirm the expected mutations.

TABLE 19

Oligonucleotides used to change residue 277 in T. maritima.

| | forward 5' to 3' | | reverse 5' to 3' |
|---|---|---|---|
| Tma_C277Vf (SEQ ID NO: 58) | ggacaacatcGTGcctccttcta | Tma_C277Vr (SEQ ID NO: 59) | TAGAAGGAGG<u>CAC</u>GATGTTGTCC |
| Tma_C277Af (SEQ ID NO: 60) | ggacaacatcGCGcctccttcta | Tma_C277Ar (SEQ ID NO: 61) | TAGAAGGAGG<u>CGC</u>GATGTTGTCC |
| Tma_0277Sf (SEQ ID NO: 62) | ggacaacatcTCAcctccttcta | Tma_C277Sr (SEQ ID NO: 63) | TAGAAGGAGG<u>TGA</u>GATGTTGTCC |
| Tma_C277Tf (SEQ ID NO: 64) | ggacaacatcACCcctccttcta | Tma_C277Tr (SEQ ID NO: 65) | TAGAAGGAGG<u>GGT</u>GATGTTGTCC |

EXAMPLE 27

Expression of *Thermotoga maritima* Acetyl Xylan Esterase Variants in *E. coli* KLP18

Plasmids with confirmed acetyl xylan esterase mutations were used to transform *E. coli* KLP18 (Example 3). Transformants were grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the acetyl xylan esterase at 20-40% of total soluble protein.

EXAMPLE 28

Preparation of Cell Lysates Containing Semi-Purified *T. maritima* Acetyl Xylan Esterase Mutants Cell cultures (prepared as described in Example 27) were grown using a fermentation protocol similar to that described in Example 7 at a 1-L scale (Applikon). Cells were harvested by centrifugation at 5,000×g for 15 minutes then resuspended (20% w/v) in 50 mM phosphate buffer pH 7.0 supplemented with 1.0 mM DTT. Resuspended cells were passed through a French pressure cell twice to ensure >95% cell lysis. Lysed cells were centrifuged for 30 minutes at 12,000×g, and the supernatant was heated at 75° C. for 20 minutes, followed by quenching in an ice bath for 2 minutes. Precipitated protein was removed by centrifugation for 10 minutes at 11,000×g. SDS-PAGE indicated that the CE-7 enzyme comprised approximately 85-90% of the total protein in the preparation.

EXAMPLE 28

Specific Activity and Perhydrolysis/Hydrolysis ratio of *T. maritima* Acetyl Xylan Wild-type Esterase and C277 Esterase Variants Reactions (40 mL total volume) were run at 25° C. in phosphate buffer (50 mM, pH 7.2) containing triacetin (100 mM), hydrogen peroxide (100 mM) and one of the following acetyl xylan esterase variants: *T. maritima* C277S variant perhydrolase (0.010 mg/mL of heat-treated extract total protein from *E. coli* KLP18/pSW228/C277S), *T. maritima* C277T variant perhydrolase (0.010 mg/mL of heat-treated extract total protein from *E. coli* KLP18/pSW228/C277T), *T. maritima* C277A variant perhydrolase (0.0125 mg/mL of heat-treated extract total protein from *E. coli* KLP18/pSW228/C277A), and *T. maritima* C277V variant perhydrolase (0.0125 mg/mL of heat-treated extract total protein from *E. coli* KLP18/pSW228/C277V) (prepared as described in Example 27). Reactions were stirred for only the first 30 seconds of reaction to initially mix the reactants and enzyme.

A reaction was also run under identical conditions to that described immediately above using 0.050 mg/mL of heat-treated extract total protein isolated from *E. coli* KLP18/pSW228 (expressing *Thermotoga maritima* wild-type acetyl xylan esterase (Example 25)), where the heat-treated extract supernatant was prepared according to the procedure of Example 27.

Two samples from each of the reaction mixtures described above were simultaneously withdrawn after the first minute of each reaction, and every two minutes thereafter for fifteen minutes, where one of the two samples was analyzed for peracetic acid using a modification of the method described by Karst et al., supra, and the second sample was analyzed for total acetic acid produced from both enzymatic hydrolysis of triacetin and from subsequent conversion of peracetic acid in sample to acetic acid by reaction with methyl-p-tolyl sulfide (MTS) (see Example 8).

The *Thermotoga maritima* acetyl xylan esterase mutants had a significantly-higher specific activity for perhydrolysis of triacetin than the wild-type esterase (Table 20). The perhydrolysis/hydrolysis ratios for the *T. maritima* acetyl xylan esterase variants were determined by dividing the rate of PAA production (perhydrolysis rate) by the rate of hydrolysis of triacetin to acetic acid (hydrolysis rate) (calculated from the rate of total acetic acid production in the assay method from both PAA and acetic acid, and corrected for the rate of peracetic acid production); the P/H ratio of the *T. maritima* acetyl xylan esterase variants were ca. equal to or greater than the P/H ratio for the *T. neapolitana* wild-type acetyl xylan esterase (Table 20).

TABLE 20

| Thermotoga maritima perhydrolase | enzyme concen. (µg/mL) | perhydrolysis rate (mM/min) | hydrolysis rate (mM/min) | P/H ratio | specific activity (U/mg protein) |
|---|---|---|---|---|---|
| wild type | 50 | 3.06 | 0.47 | 6.5 | 61 |
| C277S | 10 | 7.77 | 0.48 | 16 | 777 |
| C277T | 10 | 6.93 | 1.05 | 6.6 | 693 |
| C277A | 10 | 4.27 | 0.088 | 48 | 427 |
| C277V | 10 | 4.25 | 0.062 | 68 | 425 |

EXAMPLE 29

Peracetic Acid Production Using Perhydrolases

Reactions (100 mL total volume) containing triacetin (2 mM), hydrogen peroxide (10 mM) and from 0.1 µg/mL to 2.0 µg/mL heat-treated cell extract protein (prepared as described above, where the heat-treatment was performed at 85° C. for 20 min) were run in 10 mM sodium bicarbonate buffer (initial pH 8.1) at 20° C. Determination of the concentration of peracetic acid in the reaction mixtures was performed according to the method described by Karst et al., supra. The peracetic acid concentrations produced in 1 min, 5 min, 20 min, 40 min and 60 min are listed in Table 21.

TABLE 21

Dependence of peracetic acid (PAA) concentration on perhydrolase concentration in reactions containing triacetin (2 mM) and hydrogen peroxide (10 mM) in sodium bicarbonate buffer (10 mM, initial pH 8.1) at 20° C., using heat-treated extract protein from *E. coli* KLP18/pSW228 (*Thermotoga maritima* wild-type perhydrolase) or *E. coli* KLP18/pSW228/C277S (*Thermotoga maritima* C277S variant perhydrolase) (duplicate reactions).

| Thermotoga maritima perhydrolase | triacetin (mM) | enzyme concen. (µg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| no enzyme | 2 | 0 | 0 | 0 | 1 | 1 | 3 |
| wild type | 2 | 0.2 | 0 | 2 | 7 | 13 | 19 |
| wild type | 2 | 0.2 | 0 | 1 | 5 | 11 | 15 |
| wild type | 2 | 0.5 | 0 | 2 | 12 | 19 | 25 |
| wild type | 2 | 0.5 | 0 | 2 | 12 | 21 | 26 |
| wild type | 2 | 1.0 | 0 | 5 | 20 | 29 | 31 |
| wild type | 2 | 1.0 | 0 | 5 | 19 | 30 | 31 |
| wild type | 2 | 2.0 | 1 | 11 | 24 | 24 | 20 |
| wild type | 2 | 2.0 | 1 | 11 | 29 | 29 | 21 |
| C277S | 2 | 0.2 | 0 | 4 | 18 | 18 | 18 |
| C277S | 2 | 0.2 | 0 | 4 | 18 | 17 | 18 |
| C277S | 2 | 0.5 | 1 | 12 | 39 | 54 | 64 |
| C277S | 2 | 0.5 | 1 | 10 | 34 | 52 | 64 |
| C277S | 2 | 1.0 | 18 | 26 | 59 | 69 | 63 |
| C277S | 2 | 1.0 | 18 | 25 | 60 | 70 | 64 |
| C277S | 2 | 2.0 | 9 | 38 | 66 | 60 | 48 |
| C277S | 2 | 2.0 | 9 | 34 | 69 | 61 | 49 |

EXAMPLE 30

Peracetic Acid Production Using Perhydrolases

Reactions (100 mL total volume) containing triacetin (20 mM), hydrogen peroxide (10 mM) and from 0.1 µg/mL to 2.0 µg/mL heat-treated cell extract protein (prepared as described above, where the heat-treatment was performed at 85° C. for 20 min) were run in 10 mM sodium bicarbonate buffer (initial pH 8.1) at 20° C. Determination of the concentration of peracetic acid in the reaction mixtures was performed according to the method described by Karst et al., supra. The peracetic acid concentrations produced in 1 min, 5 min, 20 min, 40 min and 60 min are listed in Table 22.

TABLE 22

Dependence of peracetic acid (PAA) concentration on perhydrolase concentration in reactions containing triacetin (20 mM) and hydrogen peroxide (10 mM) in sodium bicarbonate buffer (10 mM, initial pH 8.1) at 20° C., using heat-treated extract protein from *E. coli* KLP18/pSW228 (*Thermotoga maritima* wild-type perhydrolase) or *E. coli* KLP18/pSW228/C277S (*Thermotoga maritima* C277S variant perhydrolase) (duplicate reactions).

| Thermotoga maritima perhydrolase | triacetin (mM) | enzyme concen. (µg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| no enzyme | 20 | 0 | 2 | 3 | 3 | 7 | 9 |
| wild-type | 20 | 0.2 | 3 | 10 | 15 | 27 | 35 |

TABLE 22-continued

Dependence of peracetic acid (PAA) concentration on perhydrolase concentration in reactions containing triacetin (20 mM) and hydrogen peroxide (10 mM) in sodium bicarbonate buffer (10 mM, initial pH 8.1) at 20° C., using heat-treated extract protein from E. coli KLP18/pSW228 (Thermotoga maritima wild-type perhydrolase) or E. coli KLP18/pSW228/C277S (Thermotoga maritima C277S variant perhydrolase) (duplicate reactions).

| Thermotoga maritima perhydrolase | triacetin (mM) | enzyme concen. (µg/mL) | PAA, 1 min (ppm) | PAA, 5 min (ppm) | PAA, 20 min (ppm) | PAA, 40 min (ppm) | PAA, 60 min (ppm) |
|---|---|---|---|---|---|---|---|
| wild-type | 20 | 0.2 | 4 | 9 | 19 | 32 | 41 |
| wild-type | 20 | 0.5 | 3 | 9 | 21 | 39 | 52 |
| wild-type | 20 | 0.5 | 3 | 8 | 22 | 39 | 54 |
| wild-type | 20 | 1.0 | 4 | 13 | 35 | 62 | 82 |
| wild-type | 20 | 1.0 | 4 | 12 | 37 | 67 | |
| wild-type | 20 | 2.0 | 9 | 20 | 52 | 91 | 122 |
| wild-type | 20 | 2.0 | 10 | 20 | 52 | 87 | 114 |
| C277S | 20 | 0.2 | 7 | 16 | 67 | 109 | 148 |
| C277S | 20 | 0.2 | 9 | 24 | 67 | 112 | 144 |
| C277S | 20 | 0.5 | 16 | 43 | 140 | 202 | 260 |
| C277S | 20 | 0.5 | 17 | 48 | 148 | 228 | 272 |
| C277S | 20 | 1.0 | 24 | 75 | 230 | 289 | 353 |
| C277S | 20 | 1.0 | 26 | 97 | 232 | 297 | 372 |
| C277S | 20 | 2.0 | 32 | 130 | 318 | 402 | 443 |
| C277S | 20 | 2.0 | 37 | 135 | 323 | 401 | 430 |

EXAMPLE 31

Peracetic Acid Production Using Perhydrolases

Reactions (40 mL total volume) were run at 25° C. in phosphate buffer (50 mM, pH 7.2) containing triacetin (100 mM), hydrogen peroxide (100 mM) and from 10 µg/mL to 50 µg/mL of heat-treated T. neapolitana or T. maritima wild-type or C277 variant perhydrolases (as heat-treated cell extract protein prepared as described above, where the heat-treatment was performed at 75° C. for 20 min). Reactions were stirred for only the first 30 seconds of reaction to initially mix the reactants and enzyme. Determination of the concentration of peracetic acid in the reaction mixtures was performed according to the method described by Karst et al., supra. The peracetic acid concentrations produced in 1 min, 5 min, and 30 min are listed in Table 23.

TABLE 23

Peracetic acid (PAA) production in reactions containing triacetin (100 mM) and hydrogen peroxide (100 mM) in phosphate buffer (50 mM, pH 7.2) at 25° C., using heat-treated T. neapolitana or T. maritima wild-type or C277 mutant perhydrolases.

| perhydrolase | triacetin (mM) | H₂O₂ (mM) | enzyme concen. (µg/mL) | PAA, 1 min (ppm) | PAA, 5 min (ppm) | PAA, 30 min (ppm) |
|---|---|---|---|---|---|---|
| no enzyme | 100 | 100 | 0 | 63 | 54 | 80 |
| T. maritima wild-type | 100 | 100 | 50 | 529 | 1790 | 3785 |
| T. maritima C277S | 100 | 100 | 10 | 979 | 3241 | 4635 |
| T. maritima C277T | 100 | 100 | 10 | 933 | 2882 | 3527 |
| T. maritima C277A | 100 | 100 | 10 | 442 | 2018 | 2485 |
| T. maritima C277V | 100 | 100 | 10 | 577 | 1931 | 2278 |
| T. neapolitana wild-type | 100 | 100 | 50 | 514 | 1837 | 3850 |
| T. neapolitana C277S | 100 | 100 | 10 | 606 | 2237 | 4609 |
| T. neapolitana C277T | 100 | 100 | 10 | 634 | 2198 | 3918 |
| T. neapolitana C277A | 100 | 100 | 12.5 | 516 | 2041 | 3735 |
| T. neapolitana C277V | 100 | 100 | 12.5 | 451 | 1813 | 2758 |

EXAMPLE 32

Peracetic Acid Production Using Perhydrolases

Reactions (10 mL total volume) were run at 25° C. in sodium bicarbonate buffer (1 mM, initial pH 6.0) containing triacetin (100 mM or 150 mM), hydrogen peroxide (100 mM, 250 mM or 420 mM) and heat-treated T. neapolitana or T. maritima wild-type, C277S or C277T variant perhydrolases (as heat-treated cell extract protein prepared as described above, where the heat-treatment was performed at 75° C. for 20 min; concentrations as listed in Table 24). Reactions run using 420 mM hydrogen peroxide additionally contained 500 ppm TURPINAL® SL. Reactions were stirred for only the first 30 seconds of reaction to initially mix the reactants and enzyme. Determination of the concentration of peracetic acid in the reaction mixtures was performed according to the method described by Karst et al., supra. The peracetic acid concentrations produced in 1 min, 5 min, and 30 min are listed in Table 24.

TABLE 24

Peracetic acid (PAA) production in reactions containing triacetin and hydrogen peroxide in bicarbonate buffer (1 mM at pH 6.0 or 100 mM at pH 8.1) or in deionized water (pH 5.0) at 25° C. using heat-treated *T. maritima* wild-type, C277S or C277T variant perhydrolases.

| *Thermotoga maritima* perhydrolase | triacetin (mM) | $H_2O_2$ (mM) | $NaHCO_3$ buffer (mM) | enzyme concen. (μg/mL) | PAA, 1 min (ppm) | PAA, 5 min (ppm) | PAA, 30 min (ppm) |
|---|---|---|---|---|---|---|---|
| no enzyme | 100 | 100 | 1.0 | 0 | 28 | 78 | 141 |
| wild-type | 100 | 100 | 1.0 | 75 | 434 | 494 | 608 |
| wild-type | 100 | 100 | 1.0 | 100 | 449 | 667 | 643 |
| C277S | 100 | 100 | 1.0 | 15 | 989 | 1554 | 1476 |
| C277S | 100 | 100 | 1.0 | 20 | 1301 | 2139 | 2131 |
| C277T | 100 | 100 | 1.0 | 15 | 1062 | 1513 | 1393 |
| C277T | 100 | 100 | 1.0 | 20 | 996 | 1430 | 1516 |
| no enzyme | 100 | 250 | 0 | 0 | 13 | 71 | 71 |
| wild-type | 100 | 250 | 0 | 75 | 512 | 535 | 533 |
| wild-type | 100 | 250 | 0 | 100 | 576 | 668 | 654 |
| C277S | 100 | 250 | 0 | 15 | 653 | 671 | 675 |
| C277S | 100 | 250 | 0 | 20 | 943 | 927 | 903 |
| C277T | 100 | 250 | 0 | 15 | 717 | 711 | 765 |
| C277T | 100 | 250 | 0 | 20 | 730 | 755 | 743 |
| no enzyme | 150 | 420 | 100 | 0 | 417 | 810 | 848 |
| wild-type | 150 | 420 | 100 | 500 | 6303 | 8627 | 9237 |
| C277S | 150 | 420 | 100 | 100 | 7822 | 10349 | 10197 |

What is claimed is:

1. A multi-component peroxycarboxylic acid generation system comprising a first compartment comprising a first component and a second compartment comprising a second component and means for mixing the first component and the second component to produce an aqueous formulation of peracetic acid;

wherein the first component comprises
  (i) an enzyme powder comprising a formulation of:
    (a) at least one enzyme catalyst having perhydrolysis activity, wherein said enzyme catalyst comprises an enzyme having a carbohydrate esterase family 7 (CE-7) signature motif that aligns with SEQ ID NO: 1 using CLUSTALW, said signature motif comprising:
      (1) an RGQ motif at amino acid positions aligning with 118-120 of SEQ ID NO:1;
      (2) a GXSQG motif at amino acid positions aligning with 179-183 of SEQ ID NO:1; and
      (3) an HE motif at amino acid positions aligning with 298-299 of SEQ ID NO:1;
      said enzyme comprising at least 30% amino acid identity to SEQ ID NO: 1; and
    (b) at least one excipient;
  (ii) a carboxylic acid ester substrate selected from the group consisting of
    (a) one or more esters having the structure $[X]_m R_5$ wherein
    X is an ester group of the formula $R_6C(O)O$;
    $R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
    $R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
    m is 1 to the number of carbon atoms in $R_5$, said one or more esters having solubility in water of at least 5 ppm at 25° C.;
    (b) one or more glycerides having the structure

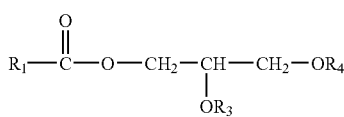

wherein $R_1$ is a C1 to C7 straight chain or branched chain alkyl optionally substituted with an hydroxyl or a C1 to C4 alkoxy group and $R_3$ and $R_4$ are individually H or $R_1C(O)$;

(c) one or more esters of the formula

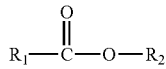

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)\text{—}O)_nH$ and n is 1 to 10;
    (d) one or more acetylated monosaccharides, acetylated disaccharides, or acetylated polysaccharides; and
    (e) any combination of (a) through (d);
    wherein the amount of the carboxylic acid ester substrate in the first component is designed to provide a final concentration of 0.5 wt % to 10 wt % in a reaction formulation formed by combining the first and second components;
  (iii) a buffer selected from the group consisting of bicarbonate, citrate, acetate, phosphate, pyrophosphate, methylphosphonate, succinate, malate, fumarate, tartrate, and maleate;
  (iv) a cosolvent selected from the group consisting of tripropylene glycol methyl ether, dipropylene glycol methyl ether, propylene glycol methyl ether, diethylene glycol butyl ether, dipropylene glycol, triethylene glycol, 1,2-propanediol, N-ethyl-2-pyrroldinone, isopropanol, ethanol, ethyl lactate, 1,3-propanediol, and any combination thereof; and
  (v) optionally at least one surfactant;
wherein the second component comprises water, hydrogen peroxide and a hydrogen peroxide stabilizer.

2. The multi-component peroxycarboxylic acid generation system of claim 1 wherein the at least one excipient ranges from about 95 wt % to about 25 wt % of the enzyme powder.

3. The multi-component peroxycarboxylic acid generation system of claim 1 or claim 2 wherein
  (i) the carboxylic acid ester substrate is triacetin; wherein the amount of triacetin in the first component is designed to provide a final concentration of 0.5 wt % to 10 wt % in a reaction formulation formed by combining the first and second components;
  (ii) the buffer is in a concentration of about 0.1 wt % to about 10% wt of a the first component and said buffer is selected from the group consisting of sodium bicarbonate, potassium bicarbonate, a mixture of sodium bicarbonate and potassium bicarbonate, sodium phosphate, potassium phosphate, and a mixture of sodium phosphate and potassium phosphate;
  (iii) the cosolvent is tripropylene glycol methyl ether and is in a concentration of up to 80 wt % of the first component;
  (iv) the surfactant is present and is polysorbate 80; and
  (v) the hydrogen peroxide in the second component is present in an amount that provides a final concentration in a reaction formulation formed by combining the first and second components of from 0.33 wt % to about 30 wt %.

4. The multi-component peroxycarboxylic acid generation system of claim 1 or claim 2 wherein the first component is combined with said second component at a ratio of about 1:1 to about 1:10 by weight.

5. The multi-component peroxycarboxylic acid generation system of claim 1 or claim 2 where the multi-component peroxycarboxylic acid generation system is provided in the form of two individual bottles, a two compartment spray bottle, a two compartment packet, or a two-compartment, non-rigid squeeze bottle.

6. A multi-component peroxycarboxylic acid generation system comprising a first compartment comprising a first component and a second compartment comprising a second component and means for mixing the first and second component to produce an aqueous formulation of peracetic acid; wherein the first component comprises
  (i) an enzyme powder comprising a formulation of
    (a) at least one CE-7 enzyme having perhydrolysis activity, wherein said at least one CE-7 enzyme comprises an amino acid sequence selected from the group consisting of SEQ ID NO: 6, SEQ ID NO: 7, SEQ ID NO: 19 and SEQ ID NO: 20 or an amino acid sequence having at least 90 % identity to SEQ ID NO: 6, SEQ ID NO: 7, SEQ ID NO: 19 or SEQ ID NO: 20; and
    (b) at least one excipient;
  (ii) a carboxylic acid ester substrate selected from the group consisting of monoacetin, diacetin, triacetin, and a mixtures thereof; wherein the amount of the carboxylic acid ester substrate in the first component is designed to provide a final concentration of 0.5 wt % to 10 wt% in a reaction formulation formed by combining the first and second components;
  (iii) a buffer selected from the group consisting of bicarbonate, citrate, acetate, phosphate, pyrophosphate, methylphosphonate, succinate, malate, fumarate, tartrate, and maleate;
  (iv) a cosolvent selected from the group consisting of tripropylene glycol methyl ether, dipropylene glycol methyl ether, propylene glycol methyl ether, diethylene glycol butyl ether, dipropylene glycol, triethylene glycol, 1,2-propanediol, N-ethyl-2-pyrroldinone, isopropanol, ethanol, ethyl lactate, 1,3-propanediol, and any combination thereof; and
  (v) optionally at least one surfactant;
wherein the second component comprises water, hydrogen peroxide and a hydrogen peroxide stabilizer.

7. The multi-component peroxycarboxylic acid generation system of claim 6 wherein:
  (i) the at least one CE-7 enzyme comprises an amino acid sequence selected from the group consisting of SEQ ID NO: 6, SEQ ID NO: 7, SEQ ID NO: 19 and SEQ ID NO: 20, wherein amino acid residue 277 of SEQ ID NO: 19 or SEQ ID NO: 20 is selected from the group consisting of alanine, valine, serine, and threonine;
  (ii) the carboxylic acid ester substrate is triacetin; wherein the amount of triacetin in the first component is designed to provide a final concentration of 0.5 wt % to 10 wt% in a reaction formulation formed by combining the first and second components;
  (iii) the buffer is in a concentration of about 0.1 wt % to about 10% wt of the first component and said buffer is selected from the group consisting of sodium bicarbonate, potassium bicarbonate, a mixture of sodium bicarbonate and potassium bicarbonate, sodium phosphate, potassium phosphate, and a mixture of sodium phosphate and potassium phosphate;
  (iv) the cosolvent is tripropylene glycol methyl ether and is in a concentration of up to 80 wt % of the first component;
  (vi) the surfactant is present and is polysorbate 80; and
  (vi) the hydrogen peroxide in the second component is present in an amount that provides a final concentration in a reaction formulation formed by combining the first and second components of from 0.33 wt % to about 30 wt %.

8. The multi-component peroxycarboxylic acid generation system of claim 6 or claim 7 wherein the first component is combined with said second component at a ratio of about 1:1 to about 1:10 by weight.

9. The multi-component peroxycarboxylic acid generation system of claim 1 or claim 6 where the multi-component peroxycarboxylic acid generation system is provided in the form of two individual bottles, a two compartment spray bottle, a two compartment packet, or a two-compartment non-rigid squeeze bottle.

10. The multi-component peroxycarboxylic acid generation system of claim 1 or claim 6, further comprising means for applying the aqueous formulation comprising peracetic acid produced by mixing the first and second components to a surface, an article of clothing or a textile for bleaching, stain removal, odor reduction, sanitization, disinfection, or a combination thereof.

11. A method of using the multi-component peroxycarboxylic acid generation system of claim 1 or claim 6 comprising
  (a) employing the means for mixing the first and second components whereby an aqueous formulation comprising peracetic acid is produced; and
  (b) applying the aqueous formulation comprising peracetic acid produced in (a) to a surface, an article of clothing or a textile for bleaching, stain removal, odor reduction, sanitization, disinfection, or a combination thereof.

* * * * *

SEQUENCE LISTING

<160> NUMBER OF SEQ ID NOS: 65

<210> SEQ ID NO 1
<211> LENGTH: 318
<212> TYPE: PRT
<213> ORGANISM: Bacillus subtilis

<400> SEQUENCE: 1

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

```
Leu Ser Asp Ile Pro Lys Ala Ala Val Ala Asp Tyr Pro Tyr Leu Ser
            195                 200                 205

Asn Phe Glu Arg Ala Ile Asp Val Ala Leu Glu Gln Pro Tyr Leu Glu
        210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Lys Glu Gly Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Lys
225                 230                 235                 240

Ala Met Lys Thr Leu Ser Tyr Phe Asp Ile Met Asn Leu Ala Asp Arg
                245                 250                 255
```

```
Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Tyr Ile Pro Ala Phe
290                 295                 300

Gln Thr Glu Lys Leu Ala Phe Phe Lys Gln His Leu Lys Gly
305                 310                 315

<210> SEQ ID NO 3
<211> LENGTH: 318
<212> TYPE: PRT
<213> ORGANISM: Bacillus licheniformis

<400> SEQUENCE: 3

Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
                85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu
130                 135                 140

Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Gly Leu Ala Val Ala Val Ser
            180                 185                 190

Ala Leu Ser Asp Ile Pro Lys Ala Ala Val Ser Glu Tyr Pro Tyr Leu
        195                 200                 205

Ser Asn Phe Gln Arg Ala Ile Asp Thr Ala Ile Asp Gln Pro Tyr Leu
210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
            260                 265                 270

Thr Pro Pro Ser Thr Val Phe Ala Ala Tyr Asn His Leu Glu Thr Asp
        275                 280                 285

Lys Glu Ile Lys Val Tyr Arg Tyr Phe Gly His Glu Tyr Ile Pro Pro
290                 295                 300

Phe Gln Thr Glu Lys Leu Ala Phe Leu Arg Lys His Leu Lys
305                 310                 315
```

<210> SEQ ID NO 4
<211> LENGTH: 320
<212> TYPE: PRT
<213> ORGANISM: Bacillus pumilus

<400> SEQUENCE: 4

```
Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
            180                 185                 190

Leu Ser Asp Ile Pro Lys Val Val Ala Asp Tyr Pro Tyr Leu Ser
        195                 200                 205

Asn Phe Glu Arg Ala Val Asp Val Ala Leu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
        275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Leu Ser Thr
305                 310                 315                 320
```

<210> SEQ ID NO 5
<211> LENGTH: 320
<212> TYPE: PRT
<213> ORGANISM: Clostridium thermocellum

<400> SEQUENCE: 5

```
Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
```

```
                    20                  25                  30
Leu Lys Glu Leu Ala Glu Ile Pro Leu Lys Tyr Gln Leu Ile Pro Tyr
                35                  40                  45

Asp Phe Pro Ala Arg Arg Val Lys Val Phe Arg Val Glu Tyr Leu Gly
             50                  55                  60

Phe Lys Gly Ala Asn Ile Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
            115                 120                 125

Ile Val Pro Gly Ser Gly His Ala Leu Gly Trp Met Ser Lys Gly Ile
            130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Leu Ala Leu Ala Val
            180                 185                 190

Ala Ala Leu Ser Gly Ile Pro Lys Val Ala Ala Val His Tyr Pro Phe
            195                 200                 205

Leu Ala His Phe Glu Arg Ala Ile Asp Val Ala Pro Asp Gly Pro Tyr
            210                 215                 220

Leu Glu Ile Asn Glu Tyr Leu Arg Arg Asn Ser Gly Glu Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
            260                 265                 270

Ile Thr Pro Pro Ser Thr Val Phe Ala Val Tyr Asn His Leu Lys Cys
            275                 280                 285

Pro Lys Glu Ile Ser Val Phe Arg Tyr Phe Gly His Glu His Met Pro
            290                 295                 300

Gly Ser Val Glu Ile Lys Leu Arg Ile Leu Met Asp Glu Leu Asn Pro
305                 310                 315                 320

<210> SEQ ID NO 6
<211> LENGTH: 325
<212> TYPE: PRT
<213> ORGANISM: Thermotoga neapolitana

<400> SEQUENCE: 6

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
                20                  25                  30

Lys Glu Ser Glu Gly Phe Pro Leu Asp Pro Val Phe Glu Lys Val Asp
            35                  40                  45

Phe His Leu Lys Thr Val Glu Thr Tyr Asp Val Thr Phe Ser Gly Tyr
            50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
```

```
            85                  90                  95
Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 7
<211> LENGTH: 325
<212> TYPE: PRT
<213> ORGANISM: Thermotoga maritima

<400> SEQUENCE: 7

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
```

```
                    130                 135                 140
Met Thr Arg Gly Ile Leu Asp Pro Arg Thr Tyr Tyr Arg Val
145                 150                 155                 160

Phe Thr Asp Ala Val Arg Ala Glu Ala Ala Ser Phe Pro Gln
                    165                 170                 175

Val Asp Gln Glu Arg Ile Val Ile Ala Gly Ser Gln Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                    245                 250                 255

Asn Phe Ala Ala Arg Ala Lys Ile Pro Ala Leu Phe Ser Val Gly Leu
                260                 265                 270

Met Asp Asn Ile Cys Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 8
<211> LENGTH: 320
<212> TYPE: PRT
<213> ORGANISM: Thermoanaerobacterium sp.

<400> SEQUENCE: 8

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
                    20                  25                  30

Asp Glu Met Arg Ser Val Asp Pro Lys Ile Glu Leu Lys Glu Ser Ser
                35                  40                  45

Phe Gln Val Ser Phe Ala Glu Cys Tyr Asp Leu Tyr Phe Thr Gly Val
            50                  55                  60

Arg Gly Ala Arg Ile His Ala Lys Tyr Ile Lys Pro Lys Thr Glu Gly
65              70                  75                  80

Lys His Pro Ala Leu Ile Arg Phe His Gly Tyr Ser Ser Asn Ser Gly
                    85                  90                  95

Asp Trp Asn Asp Lys Leu Asn Tyr Val Ala Ala Gly Phe Thr Val Val
                100                 105                 110

Ala Met Asp Val Arg Gly Gln Gly Gly Gln Ser Gln Asp Val Gly Gly
                115                 120                 125

Val Thr Gly Asn Thr Leu Asn Gly His Ile Ile Arg Gly Leu Asp Asp
                130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                    165                 170                 175

Gly Val Met Gly Pro Ser Gln Gly Gly Gly Leu Ser Leu Ala Cys Ala
```

```
                    180                 185                 190
Ala Leu Glu Pro Arg Val Arg Lys Val Val Ser Glu Tyr Pro Phe Leu
                195                 200                 205

Ser Asp Tyr Lys Arg Val Trp Asp Leu Asp Leu Ala Lys Asn Ala Tyr
210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
                260                 265                 270

Gln Val Cys Pro Pro Ser Thr Val Phe Ala Ala Tyr Asn Asn Ile Gln
                275                 280                 285

Ser Lys Lys Asp Ile Lys Val Tyr Pro Asp Tyr Gly His Glu Pro Met
                290                 295                 300

Arg Gly Phe Gly Asp Leu Ala Met Gln Phe Met Leu Glu Leu Tyr Ser
305                 310                 315                 320

<210> SEQ ID NO 9
<211> LENGTH: 325
<212> TYPE: PRT
<213> ORGANISM: Bacillus sp.

<400> SEQUENCE: 9

Met Asn Leu Phe Asp Met Pro Leu Glu Glu Leu Gln His Tyr Lys Pro
1               5                   10                  15

Ala Gln Thr Arg Gln Asp Asp Phe Glu Ser Phe Trp Lys Lys Arg Ile
                20                  25                  30

Glu Glu Asn Ser Gln Tyr Pro Leu Asn Ile Glu Val Met Glu Arg Val
            35                  40                  45

Tyr Pro Val Pro Gly Val Arg Val Tyr Asp Ile Tyr Phe Asp Gly Phe
50                  55                  60

Arg Asn Ser Arg Ile His Gly Val Tyr Val Thr Pro Glu Thr Pro Gly
65                  70                  75                  80

Ala Asp Thr Pro Ala Ala Val Ile Phe His Gly Tyr Asn Trp Asn Thr
                85                  90                  95

Leu Gln Pro His Tyr Ser Phe Lys His Val Ile Gln Gly Ile Pro Val
            100                 105                 110

Leu Met Val Glu Val Arg Gly Gln Asn Leu Leu Ser Pro Asp Arg Asn
        115                 120                 125

His Tyr Gly Asn Gly Gly Pro Gly Gly Trp Met Thr Leu Gly Val Met
130                 135                 140

Asp Pro Asp Gln Tyr Tyr Tyr Ser Leu Val Tyr Met Asp Cys Phe Arg
145                 150                 155                 160

Ser Ile Asp Ala Val Arg Glu Leu Ser Arg Lys Arg Ser Val Phe Val
                165                 170                 175

Glu Gly Gly Ser Gln Gly Gly Ala Leu Ala Ile Ala Ala Ala Ala Leu
            180                 185                 190

Gln Asp Asp Ile Leu Leu Ala Leu Ala Asp Ile Pro Phe Leu Thr His
        195                 200                 205

Phe Lys Arg Ser Val Glu Leu Ser Ser Asp Gly Pro Tyr Gln Glu Ile
        210                 215                 220

Ser His Tyr Phe Lys Val His Asp Pro Leu His Gln Thr Glu Glu Gln
225                 230                 235                 240

Val Tyr Gln Thr Leu Ser Tyr Val Asp Cys Met Asn Met Ala Ser Met
```

```
                    245                 250                 255
Val Glu Cys Pro Val Leu Leu Ser Ala Gly Leu Glu Asp Ile Val Cys
            260                 265                 270

Pro Pro Ser Ser Ala Phe Ala Leu Phe Asn His Leu Gly Gly Pro Lys
            275                 280                 285

Glu Ile Arg Ala Tyr Pro Glu Tyr Ala His Glu Val Pro Ala Val His
            290                 295                 300

Glu Glu Glu Lys Leu Lys Phe Ile Ser Ser Arg Leu Lys Asn Arg Glu
305                 310                 315                 320

Lys Arg Cys Arg Pro
                325

<210> SEQ ID NO 10
<211> LENGTH: 319
<212> TYPE: PRT
<213> ORGANISM: Bacillus halodurans

<400> SEQUENCE: 10

Met Pro Leu Ile Asp Met Pro Leu Thr Glu Leu Lys Glu Tyr Met Gly
1               5                   10                  15

Arg Asn Pro Lys Pro Asp Phe Thr Glu Tyr Trp Asp Arg Ala Leu
            20                  25                  30

Gln Glu Met Arg Lys Val Asn Pro Asn Val Glu Leu Ile Pro Ser Asp
            35                  40                  45

Phe Gln Thr Thr Tyr Ala Glu Cys Phe His Leu Tyr Phe Thr Gly Val
        50                  55                  60

Arg Gly Ala Arg Ile His Ala Lys Tyr Val Arg Pro Arg His Thr Ser
65                  70                  75                  80

Gly Thr His Pro Ala Val Ile His Phe His Gly Tyr Thr Met Asn Ala
                85                  90                  95

Gly Glu Trp Thr Gly Leu Leu His Tyr Ala Ala Leu Gly Tyr Ser Val
            100                 105                 110

Leu Ala Met Asp Val Arg Gly Gln Gly Gly Leu Ser Glu Asp Thr Gly
            115                 120                 125

Gly Val Lys Gly Asn Thr His Ser Gly His Ile Ile Arg Gly Leu Asp
        130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
            195                 200                 205

Leu Ser Asp Tyr Gln Arg Val Trp Glu Met Asp Leu Ala Glu Lys Ala
        210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Ala Val Gly Leu Met
            260                 265                 270

Asp Thr Val Cys Pro Pro Ser Thr Gln Phe Ala Met Tyr Asn Lys Leu
            275                 280                 285

Thr Thr Thr Lys Ser Ile Glu Leu Tyr Pro Asp Phe Ala His Glu Asp
```

```
                290                 295                 300
Leu Pro Gly His Arg Asp Arg Ile Phe Gln Phe Leu Ser Asp Leu
305                 310                 315

<210> SEQ ID NO 11
<211> LENGTH: 317
<212> TYPE: PRT
<213> ORGANISM: Bacillus clausii

<400> SEQUENCE: 11

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Tyr Arg Ser Ala
    50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Gly Thr Ser Glu Asp Pro Gly Gly
        115                 120                 125

Val Arg Gly Asn Thr Tyr Arg Gly His Ile Ile Arg Gly Leu Asp Ala
    130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr
    210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Phe Thr Ser
305                 310                 315

<210> SEQ ID NO 12
<211> LENGTH: 318
<212> TYPE: PRT
<213> ORGANISM: Bacillus subtilis

<400> SEQUENCE: 12
```

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
                20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
                100                 105                 110

Phe Gly Met Leu Val Arg Gly Gln Gln Ser Ser Glu Asp Thr Ser Ile
            115                 120                 125

Ser Pro His Gly His Ala Leu Gly Trp Met Thr Lys Gly Ile Leu Asp
        130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
    195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
            245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 13
<211> LENGTH: 320
<212> TYPE: PRT
<213> ORGANISM: Thermoanearobacerium saccharolyticum

<400> SEQUENCE: 13

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asp Arg Ala Leu
                20                  25                  30

Asp Glu Met Arg Ser Val Asp Pro Lys Ile Lys Met Lys Lys Ser Ser
            35                  40                  45

Phe Gln Val Pro Phe Ala Glu Cys Tyr Asp Leu Tyr Phe Thr Gly Val
    50                  55                  60
```

```
Arg Gly Ala Arg Ile His Ala Lys Tyr Ile Arg Pro Lys Thr Glu Gly
 65                  70                  75                  80

Lys His Pro Ala Leu Ile Arg Phe His Gly Tyr Ser Ser Asn Ser Gly
                 85                  90                  95

Asp Trp Asn Asp Lys Leu Asn Tyr Val Ala Ala Gly Phe Thr Val Val
            100                 105                 110

Ala Met Asp Ala Arg Gly Gln Gly Gly Gln Ser Gln Asp Val Gly Gly
        115                 120                 125

Val Asn Gly Asn Thr Leu Asn Gly His Ile Ile Arg Gly Leu Asp Asp
130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Lys Asn Ala Tyr
210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
290                 295                 300

Arg Gly Phe Gly Asp Leu Ala Met Gln Phe Met Leu Glu Leu Tyr Ser
305                 310                 315                 320

<210> SEQ ID NO 14
<211> LENGTH: 326
<212> TYPE: PRT
<213> ORGANISM: Thermotoga lettingae

<400> SEQUENCE: 14

Met Val Tyr Phe Asp Met Pro Leu Glu Asp Leu Arg Lys Tyr Leu Pro
 1               5                  10                  15

Gln Arg Tyr Glu Glu Lys Asp Phe Asp Asp Phe Trp Lys Gln Thr Ile
             20                  25                  30

His Glu Thr Arg Gly Tyr Phe Gln Glu Pro Ile Leu Lys Lys Val Asp
         35                  40                  45

Phe Tyr Leu Gln Asn Val Glu Thr Phe Asp Val Thr Phe Ser Gly Tyr
     50                  55                  60

Arg Gly Gln Lys Ile Lys Gly Trp Leu Ile Leu Pro Lys Phe Arg Asn
 65                  70                  75                  80

Gly Lys Leu Pro Cys Val Val Glu Phe Val Gly Tyr Gly Gly Arg
                 85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125
```

```
Thr Pro Asp Tyr Glu Asp Asn Pro Ser Asp Pro Gln Tyr Pro Gly Phe
            130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
            195                 200                 205

Cys Asp Val Pro Phe Leu Cys His Tyr Lys Arg Ala Val Gln Ile Thr
            210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
            290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 15
<211> LENGTH: 325
<212> TYPE: PRT
<213> ORGANISM: Thermotoga petrophila

<400> SEQUENCE: 15

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
                20                  25                  30

Ala Glu Asn Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Asp Pro Val Asp Gln Tyr Pro Gly Phe
            130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175
```

```
Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Cys Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 16
<211> LENGTH: 325
<212> TYPE: PRT
<213> ORGANISM: Thermotoga sp.

<400> SEQUENCE: 16

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
                115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220
```

-continued

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Val Arg Ala Lys Ile Pro Ala Leu Phe Ser Val Gly Leu
        260                 265                 270

Met Asp Asn Ile Cys Pro Pro Ser Thr Val Phe Ala Ala Tyr Asn His
    275                 280                 285

Tyr Ala Gly Pro Lys Glu Ile Arg Ile Tyr Pro Tyr Asn Asn His Glu
290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 17
<211> LENGTH: 279
<212> TYPE: PRT
<213> ORGANISM: Thermotoga sp.

<400> SEQUENCE: 17

Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

```
Leu Met Asp Lys Thr Cys Pro
        275

<210> SEQ ID NO 18
<211> LENGTH: 182
<212> TYPE: PRT
<213> ORGANISM: Bacillus subtilis

<400> SEQUENCE: 18

Arg Gly Gln Gln Ser Ser Glu Asp Thr Ser Ile Ser Leu His Gly His
1               5                   10                  15

Ala Leu Gly Trp Met Thr Lys Gly Ile Leu Asp Lys Asp Thr Tyr Tyr
            20                  25                  30

Tyr Arg Gly Val Tyr Leu Asp Ala Val Arg Ala Leu Glu Val Ile Ser
        35                  40                  45

Ser Phe Asp Glu Val Asp Glu Thr Arg Ile Gly Val Thr Gly Gly Ser
    50                  55                  60

Gln Gly Gly Gly Leu Thr Ile Ala Ala Ala Leu Ser Asp Ile Pro
65                  70                  75                  80

Lys Ala Ala Val Ala Asp Tyr Pro Tyr Leu Ser Asn Phe Glu Arg Ala
                85                  90                  95

Ile Asp Val Ala Leu Glu Gln Pro Tyr Leu Glu Ile Asn Ser Phe Phe
            100                 105                 110

Arg Arg Asn Gly Ser Pro Glu Thr Glu Val Gln Ala Met Lys Thr Leu
        115                 120                 125

Ser Tyr Phe Asp Ile Met Asn Leu Ala Asp Arg Val Lys Val Pro Val
    130                 135                 140

Leu Met Ser Ile Gly Leu Ile Asp Lys Val Thr Pro Pro Ser Thr Val
145                 150                 155                 160

Phe Ala Ala Tyr Asn His Leu Glu Thr Glu Lys Glu Leu Lys Val Tyr
                165                 170                 175

Arg Tyr Phe Gly His Glu
            180

<210> SEQ ID NO 19
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 19

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110
```

```
Phe Val Met Asp Thr Arg Gly Gln Gly Ser Gly Trp Met Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Gly Thr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 20
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 20

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
```

```
                130             135             140
Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
                    165                 170                 175

Val Asp Gln Glu Arg Ile Val Ile Ala Gly Ser Gln Gly Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                    245                 250                 255

Asn Phe Ala Ala Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 21
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 21

Met Val Tyr Phe Asp Met Pro Leu Glu Asp Leu Arg Lys Tyr Leu Pro
1               5                   10                  15

Gln Arg Tyr Glu Glu Lys Asp Phe Asp Phe Trp Lys Gln Thr Ile
                20                  25                  30

His Glu Thr Arg Gly Tyr Phe Gln Glu Pro Ile Leu Lys Lys Val Asp
                35                  40                  45

Phe Tyr Leu Gln Asn Val Glu Thr Phe Asp Val Thr Phe Ser Gly Tyr
                50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Arg
                    85                  90                  95

Gly Phe Pro Tyr Asp Trp Leu Leu Trp Ser Ala Ala Gly Tyr Ala His
                100                 105                 110

Phe Ile Met Asp Thr Arg Gly Gln Gly Ser Asn Trp Met Lys Gly Asp
                115                 120                 125

Thr Pro Asp Tyr Glu Asp Asn Pro Ser Asp Pro Gln Tyr Pro Gly Phe
                130                 135                 140

Leu Thr Lys Gly Val Leu Asn Pro Glu Thr Tyr Tyr Tyr Arg Arg Val
145                 150                 155                 160
```

```
Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Xaa Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 22
<211> LENGTH: 325
<212> TYPE: PRT
<213> ORGANISM: Thermotoga petrophila
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 22

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
            180                 185                 190
```

```
Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 23
<211> LENGTH: 325
<212> TYPE: PRT
<213> ORGANISM: Thermotoga sp.
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 23

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
```

```
            210                 215                 220
Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 24
<211> LENGTH: 329
<212> TYPE: PRT
<213> ORGANISM: Thermotoga sp.
<220> FEATURE:
<221> NAME/KEY: MISC_FEATURE
<222> LOCATION: (278)..(278)
<223> OTHER INFORMATION: Xaa is Ala, Val, Ser, or Thr

<400> SEQUENCE: 24

Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
                20                  25                  30

Glu Glu Ser Arg Lys Phe Pro Leu Asp Pro Ile Phe Glu Arg Val Asp
            35                  40                  45

Tyr Leu Leu Glu Asn Val Glu Val Tyr Asp Val Thr Phe Ser Gly Tyr
50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
                100                 105                 110

His Phe Val Met Asp Thr Arg Gly Gln Gly Thr Ser Arg Val Lys Gly
            115                 120                 125

Asp Thr Pro Asp Tyr Cys Asp Glu Pro Ile Asn Pro Gln Phe Pro Gly
130                 135                 140

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
                180                 185                 190

Gly Ile Ala Leu Ala Val Ala Ala Leu Ser Glu Ile Pro Lys Ala Leu
            195                 200                 205

Val Ser Asn Val Pro Phe Leu Cys His Phe Arg Arg Ala Val Gln Ile
210                 215                 220

Thr Asp Asn Ala Pro Tyr Ser Glu Ile Val Asn Tyr Leu Lys Val His
225                 230                 235                 240
```

```
Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 25
<211> LENGTH: 320
<212> TYPE: PRT
<213> ORGANISM: Thermoanaerobacter sp.
<220> FEATURE:
<221> NAME/KEY: MISC_FEATURE
<222> LOCATION: (275)..(275)
<223> OTHER INFORMATION: Xaa is Ala, Val, Ser, or Thr.

<400> SEQUENCE: 25

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Asp Val Gly Gly
        115                 120                 125

Val Thr Gly Asn Thr Leu Asn Gly His Ile Ile Arg Gly Leu Asp Asp
130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Gly Leu Ser Leu Ala Cys Ala
            180                 185                 190

Ala Leu Glu Pro Arg Val Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270
```

```
Gln Val Xaa Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 26
<211> LENGTH: 795
<212> TYPE: DNA
<213> ORGANISM: Streptomyces kanamyceticus

<400> SEQUENCE: 26
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat gggcgaagt  gccggggcag     300 gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctaa                                                      795

<210> SEQ ID NO 27
<211> LENGTH: 3434
<212> TYPE: DNA
<213> ORGANISM: Artificial sequence
<220> FEATURE:
<223> OTHER INFORMATION: Plasmid pKD13

<400> SEQUENCE: 27
agattgcagc attacacgtc ttgagcgatt gtgtaggctg gagctgcttc gaagttccta      60
tactttctag agaataggaa cttcggaata ggaacttcaa gatcccctta ttagaagaac     120
tcgtcaagaa ggcgatagaa ggcgatgcgc tgcgaatcgg gagcggcgat accgtaaagc     180
acgaggaagc ggtcagccca ttcgccgcca agctcttcag caatatcacg ggtagccaac     240
gctatgtcct gatagcggtc cgccacaccc agccggccac agtcgatgaa tccagaaaag     300
cggccatttt ccaccatgat attcggcaag caggcatcgc catgggtcac gacgagatcc     360
tcgccgtcgg gcatgcgcgc cttgagcctg gcgaacagtt cggctggcgc gagcccctga     420
tgctcttcgt ccagatcatc ctgatcgaca agaccggctt ccatccgagt acgtgctcgc     480
tcgatgcgat gtttcgcttg gtggtcgaat gggcaggtag ccggatcaag cgtatgcagc     540
cgccgcattg catcagccat gatggatact ttctcggcag gagcaaggtg agatgacagg     600
agatcctgcc ccggcacttc gcccaatagc agccagtccc ttcccgcttc agtgacaacg     660
tcgagcacag ctgcgcaagg aacgcccgtc gtggccagcc acgatagccg cgctgcctcg     720
```

```
tcctgcagtt cattcagggc accggacagg tcggtcttga caaaaagaac cgggcgcccc    780
tgcgctgaca gccggaacac ggcggcatca gagcagccga ttgtctgttg tgcccagtca    840
tagccgaata gcctctccac ccaagcggcc ggagaacctg cgtgcaatcc atcttgttca    900
atcatgcgaa acgatcctca tcctgtctct tgatcagatc ttgatcccct cgccatcag    960
atccttggcg gcaagaaagc catccagttt actttgcagg gcttcccaac cttaccagag   1020
ggcgccccag ctggcaattc cggttcgctt gctgtccata aaaccgccca gtctagctat   1080
cgccatgtaa gcccactgca agctacctgc tttctctttg cgcttgcgtt ttcccttgtc   1140
cagatagccc agtagctgac attcatccgg ggtcagcacc gtttctgcgg actggctttc   1200
tacgtgttcc gcttccttta gcagcccttg cgccctgagt gcttgcggca gcgtgagctt   1260
caaaagcgct ctgaagttcc tatactttct agagaatagg aacttcgaac tgcaggtcga   1320
cggatccccg gaattaattc tcatgtttga cagcttatca ctgatcagtg aattaatggc   1380
gatgacgcat cctcacgata atatccgggt aggcgcaatc actttcgtct ctactccgtt   1440
acaaagcgag gctgggtatt tcccggcctt tctgttatcc gaaatccact gaaagcacag   1500
cggctggctg aggagataaa taataaacga ggggctgtat gcacaaagca tcttctgttg   1560
agttaagaac gagtatcgag atggcacata gccttgctca aattggaatc aggtttgtgc   1620
caataccagt agaaacagac gaagaagcta gctttgcact ggattgcgag gctttgccat   1680
ggctaattcc catgtcagcc gttaagtgtt cctgtgtcac tgaaaattgc tttgagaggc   1740
tctaagggct tctcagtgcg ttacatccct ggcttgttgt ccacaaccgt aaaaccttaa   1800
aagctttaaa agccttatat attctttttt ttcttataaa acttaaaacc ttagaggcta   1860
tttaagttgc tgatttatat taattttatt gttcaaacat gagagcttag tacgtgaaac   1920
atgagagctt agtacgttag ccatgagagc ttagtacgtt agccatgagg gtttagttcg   1980
ttaaacatga gagcttagta cgttaaacat gagagcttag tacgtgaaac atgagagctt   2040
agtacgtact atcaacaggt tgaactgcgg atcttgcggc cgcaaaaatt aaaaatgaag   2100
ttttaaatca atctaaagta tatatgagta aacttggtct gacagttacc aatgcttaat   2160
cagtgaggca cctatctcag cgatctgtct atttcgttca tccatagttg cctgactccc   2220
cgtcgtgtag ataactacga tacgggaggg cttaccatct ggccccagtg ctgcaatgat   2280
accgcgagac ccacgctcac cggctccaga tttatcagca ataaaccagc cagccggaag   2340
ggccgagcgc agaagtggtc ctgcaacttt atccgcctcc atccagtcta ttaattgttg   2400
ccgggaagct agagtaagta gttcgccagt taatagtttg cgcaacgttg ttgccattgc   2460
tacaggcatc gtggtgtcac gctcgtcgtt tggtatggct tcattcagct ccggttccca   2520
acgatcaagg cgagttacat gatccccat gttgtgcaaa aaagcggtta gctccttcgg   2580
tcctccgatc gttgtcagaa gtaagttggc cgcagtgtta tcactcatgg ttatggcagc   2640
actgcataat tctcttactg tcatgccatc cgtaagatgc ttttctgtga ctggtgagta   2700
ctcaaccaag tcattctgag aatagtgtat gcggcgaccg agttgctctt gcccggcgtc   2760
aatacgggat aataccgcgc cacatagcag aactttaaaa gtgctcatca ttggaaaacg   2820
ttcttcgggg cgaaaactct caaggatctt accgctgttg agatccagtt cgatgtaacc   2880
cactcgtgca cccaactgat cttcagcatc ttttactttc accagcgttt ctgggtgagc   2940
aaaaacagga aggcaaaatg ccgcaaaaaa gggaataagg gcgacacgga aatgttgaat   3000
actcatactc ttccttttc aatattattg aagcatttat cagggttatt gtctcatgag   3060
cggatacata tttgaatgta tttagaaaaa taaacaaata ggggttccgc gcacatttcc   3120
```

```
ccgaaaagtg ccacctgcat cgatggcccc cgatggtag tgtggggtct ccccatgcga    3180
gagtagggaa ctgccaggca tcaaataaaa cgaaaggctc agtcgaaaga ctgggccttt    3240
cgttttatct gttgtttgtc ggtgaacgct ctcctgagta ggacaaatcc gccgggagcg    3300
gatttgaacg ttgcgaagca acggcccgga gggtggcggg caggacgccc gccataaact    3360
gccaggcatc aaattaagca gaaggccatc ctgacggatg ccttttttgc gtggccagtg    3420
ccaagcttgc atgc                                                      3434

<210> SEQ ID NO 28
<211> LENGTH: 80
<212> TYPE: DNA
<213> ORGANISM: Artificial sequence
<220> FEATURE:
<223> OTHER INFORMATION: Primer

<400> SEQUENCE: 28
atgagcacgt cagacgatat ccataacacc acagccactg gcaaatgccc gttccatcag    60
gtgtaggctg gagctgcttc                                                80

<210> SEQ ID NO 29
<211> LENGTH: 82
<212> TYPE: DNA
<213> ORGANISM: Artificial sequence
<220> FEATURE:
<223> OTHER INFORMATION: Primer

<400> SEQUENCE: 29
taacagcagg tcgaaacggt cgaggttcat cactttcacc catgccgcca cgaagtcttt    60
attccgggga tccgtcgacc tg                                             82

<210> SEQ ID NO 30
<211> LENGTH: 1424
<212> TYPE: DNA
<213> ORGANISM: Artificial sequence
<220> FEATURE:
<223> OTHER INFORMATION: Synthetic construct

<400> SEQUENCE: 30
taacagcagg tcgaaacggt cgaggttcat cactttcacc catgccgcca cgaagtcttt    60
attccgggga tccgtcgacc tgcagttcga agttcctatt ctctagaaag tataggaact   120
tcagagcgct tttgaagctc acgctgccgc aagcactcag gcgcaagggc tgctaaagg    180 aagcggaaca cgtagaaagc cagtccgcag aaacggtgct gacccggat gaatgtcagc   240 tactgggcta tctggacaag gaaaacgca agcgcaaaga gaaagcaggt agcttgcagt   300
gggcttacat ggcgatagct agactggcg gttttatgga cagcaagcga accggaattg   360
ccagctgggg cgccctctgg taaggttggg aagccctgca agtaaactg gatggctttc   420 ttgccgccaa ggatctgatg gcgcaggga tcaagatctg atcaagagac aggatgagga   480
tcgtttcgca tgattgaaca agatggattg cacgcaggtt ctccggccgc ttgggtggag   540
aggctattcg gctatgactg gcacaacag acaatcggct gctctgatgc cgccgtgttc   600
cggctgtcag cgcaggggcg cccggttctt tttgtcaaga ccgacctgtc cggtgccctg   660
aatgaactgc aggacgaggc agcgcggcta tcgtggctgg ccacgacggg cgttccttgc   720
gcagctgtgc tcgacgttgt cactgaagcg ggaagggact ggctgctatt gggcgaagtg   780
ccggggcagg atctcctgtc atctcacctt gctcctgccg agaaagtatc catcatggct   840
gatgcaatgc ggcggctgca tacgcttgat ccggctacct gcccattcga ccaccaagcg   900
```

| | |
|---|---|
| aaacatcgca tcgagcgagc acgtactcgg atggaagccg gtcttgtcga tcaggatgat | 960 |
| ctggacgaag agcatcaggg gctcgcgcca gccgaactgt tcgccaggct caaggcgcgc | 1020 |
| atgcccgacg gcgaggatct cgtcgtgacc catggcgatg cctgcttgcc gaatatcatg | 1080 |
| gtggaaaatg gccgcttttc tggattcatc gactgtggcc ggctgggtgt ggcggaccgc | 1140 |
| tatcaggaca tagcgttggc tacccgtgat attgctgaag agcttggcgg cgaatgggct | 1200 |
| gaccgcttcc tcgtgcttta cggtatcgcc gctcccgatt cgcagcgcat cgccttctat | 1260 |
| cgccttcttg acgagttctt ctaataaggg gatcttgaag ttcctattcc gaagttccta | 1320 |
| ttctctagaa agtataggaa cttcgaagca gctccagcct acacctgatg gaacgggcat | 1380 |
| ttgccagtgg ctgtggtgtt atggatatcg tctgacgtgc tcat | 1424 |

<210> SEQ ID NO 31
<211> LENGTH: 2181
<212> TYPE: DNA
<213> ORGANISM: Escherichia coli

<400> SEQUENCE: 31

| | |
|---|---|
| atgagcacgt cagacgatat ccataacacc acagccactg gcaaatgccc gttccatcag | 60 |
| ggcggtcacg accagagtgc gggggcgggc acaaccactc gcgactggtg gccaaatcaa | 120 |
| cttcgtgttg acctgttaaa ccaacattct aatcgttcta acccactggg tgaggacttt | 180 |
| gactaccgca agaattcag caaattagat tactacggcc tgaaaaaga tctgaaagcc | 240 |
| ctgttgacag aatctcaacc gtggtggcca gccgactggg gcagttacgc cggtctgttt | 300 |
| attcgtatgg cctggcacgg cgcggggact taccgttcaa tcgatggacg cggtggcgcg | 360 |
| ggtcgtggtc agcaacgttt tgcaccgctg aactcctggc cggataacgt aagcctcgat | 420 |
| aaagcgcgtc gcctgttgtg gccaatcaaa cagaaatatg gtcagaaaat ctcctgggcc | 480 |
| gacctgttta tcctcgcggg taacgtggcg ctagaaaact ccggcttccg taccttcggt | 540 |
| tttggtgccg gtcgtgaaga cgtctgggaa ccggatctgg atgttaactg gggtgatgaa | 600 |
| aaagcctggc tgactcaccg tcatccggaa gcgctggcga agcaccgct gggtgcaacc | 660 |
| gagatgggtc tgatttacgt taacccggaa ggcccggatc acagcggcga accgctttct | 720 |
| gcggcagcag ctatccgcgc gaccttcggc aacatgggca tgaacgacga agaaaccgtg | 780 |
| gcgctgattg cgggtggtca tacgctgggt aaaacccacg gtgccggtcc gacatcaaat | 840 |
| gtaggtcctg atccagaagc tgcaccgatt gaagaacaag gtttaggttg gcgagcact | 900 |
| tacggcagcg gcgttggcgc agatgccatt acctctggtc tggaagtagt ctggaccccag | 960 |
| acgccgaccc agtggagcaa ctatttcttc gagaacctgt tcaagtatga gtgggtacag | 1020 |
| acccgcagcc cggctggcgc aatccagttc gaagcggtag acgcaccgga aattatcccg | 1080 |
| gatccgtttg atccgtcgaa gaaacgtaaa ccgacaatgc tggtgaccga cctgacgctg | 1140 |
| cgttttgatc ctgagttcga aagatctct cgtcgttttcc tcaacgatcc gcaggcgttc | 1200 |
| aacgaagcct ttgcccgtgc ctggttcaaa ctgacgcaca gggatatggg gccgaaatct | 1260 |
| cgctacatcg gccggaagt gccgaaagaa gatctgatct ggcaagatcc gctgccgcag | 1320 |
| ccgatctaca cccgaccga gcaggacatt atcgatctga aattcgcgat gcggattct | 1380 |
| ggtctgtctg ttagtgagct ggtatccgtg gcctgggcat ctgcttctac cttccgtggt | 1440 |
| ggcgacaaac gcggtggtgc caacggtgcg cgtctggcat taatgccgca gcgcgactgg | 1500 |
| gatgtgaacg ccgcagccgt tcgtgctctg cctgttctgg agaaaatcca gaaagagtct | 1560 |
| ggtaaagcct cgctggcgga tatcatagtg ctggctggtg tggttggtgt tgagaaagcc | 1620 |

-continued

```
gcaagcgccg caggtttgag cattcatgta ccgtttgcgc cgggtcgcgt tgatgcgcgt    1680
caggatcaga ctgacattga gatgtttgag ctgctggagc caattgctga cggtttccgt    1740
aactatcgcg ctcgtctgga cgtttccacc accgagtcac tgctgatcga caaagcacag    1800
caactgacgc tgaccgcgcc ggaaatgact gcgctggtgg gcggcatgcg tgtactgggt    1860
gccaacttcg atggcagcaa aaacggcgtc ttcactgacc gcgttggcgt attgagcaat    1920
gacttcttcg tgaacttgct ggatatgcgt tacgagtgga agcgaccga cgaatcgaaa    1980 gagctgttcg aaggccgtga ccgtgaaacc ggcgaagtga atttacggc cagccgtgcg    2040 gatctggtgt ttggttctaa ctccgtcctg cgtgcggtgg cggaagttta cgccagtagc    2100
gatgcccacg agaagtttgt taaagacttc gtggcggcat gggtgaaagt gatgaacctc    2160
gaccgtttcg acctgctgta a                                              2181
```

<210> SEQ ID NO 32
<211> LENGTH: 726
<212> TYPE: PRT
<213> ORGANISM: Escherichia coli

<400> SEQUENCE: 32

```
Met Ser Thr Ser Asp Asp Ile His Asn Thr Thr Ala Thr Gly Lys Cys
1               5                   10                  15

Pro Phe His Gln Gly Gly His Asp Gln Ser Ala Gly Ala Gly Thr Thr
                20                  25                  30

Thr Arg Asp Trp Trp Pro Asn Gln Leu Arg Val Asp Leu Leu Asn Gln
            35                  40                  45

His Ser Asn Arg Ser Asn Pro Leu Gly Glu Asp Phe Asp Tyr Arg Lys
        50                  55                  60

Glu Phe Ser Lys Leu Asp Tyr Tyr Gly Leu Lys Lys Asp Leu Lys Ala
65                  70                  75                  80

Leu Leu Thr Glu Ser Gln Pro Trp Trp Pro Ala Asp Trp Gly Ser Tyr
                85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
        115                 120                 125

Pro Leu Asn Ser Trp Pro Asp Asn Val Ser Leu Asp Lys Ala Arg Arg
    130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
            180                 185                 190

Leu Asp Val Asn Trp Gly Asp Glu Lys Ala Trp Leu Thr His Arg His
        195                 200                 205

Pro Glu Ala Leu Ala Lys Ala Pro Leu Gly Ala Thr Glu Met Gly Leu
    210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly Gly His Thr Leu Gly Lys Thr
            260                 265                 270

His Gly Ala Gly Pro Thr Ser Asn Val Gly Pro Asp Pro Glu Ala Ala
```

-continued

```
                275                 280                 285
Pro Ile Glu Glu Gln Gly Leu Gly Trp Ala Ser Thr Tyr Gly Ser Gly
290                 295                 300

Val Gly Ala Asp Ala Ile Thr Ser Gly Leu Glu Val Val Trp Thr Gln
305                 310                 315                 320

Thr Pro Thr Gln Trp Ser Asn Tyr Phe Phe Glu Asn Leu Phe Lys Tyr
                325                 330                 335

Glu Trp Val Gln Thr Arg Ser Pro Ala Gly Ala Ile Gln Phe Glu Ala
                340                 345                 350

Val Asp Ala Pro Glu Ile Ile Pro Asp Pro Phe Asp Pro Ser Lys Lys
                355                 360                 365

Arg Lys Pro Thr Met Leu Val Thr Asp Leu Thr Leu Arg Phe Asp Pro
370                 375                 380

Glu Phe Glu Lys Ile Ser Arg Arg Phe Leu Asn Asp Pro Gln Ala Phe
385                 390                 395                 400

Asn Glu Ala Phe Ala Arg Ala Trp Phe Lys Leu Thr His Arg Asp Met
                405                 410                 415

Gly Pro Lys Ser Arg Tyr Ile Gly Pro Glu Val Pro Lys Glu Asp Leu
                420                 425                 430

Ile Trp Gln Asp Pro Leu Pro Gln Pro Ile Tyr Asn Pro Thr Glu Gln
                435                 440                 445

Asp Ile Ile Asp Leu Lys Phe Ala Ile Ala Asp Ser Gly Leu Ser Val
450                 455                 460

Ser Glu Leu Val Ser Val Ala Trp Ala Ser Ala Ser Thr Phe Arg Gly
465                 470                 475                 480

Gly Asp Lys Arg Gly Gly Ala Asn Gly Ala Arg Leu Ala Leu Met Pro
                485                 490                 495

Gln Arg Asp Trp Asp Val Asn Ala Ala Ala Val Arg Ala Leu Pro Val
                500                 505                 510

Leu Glu Lys Ile Gln Lys Glu Ser Gly Lys Ala Ser Leu Ala Asp Ile
                515                 520                 525

Ile Val Leu Ala Gly Val Val Gly Val Glu Lys Ala Ala Ser Ala Ala
530                 535                 540

Gly Leu Ser Ile His Val Pro Phe Ala Pro Gly Arg Val Asp Ala Arg
545                 550                 555                 560

Gln Asp Gln Thr Asp Ile Glu Met Phe Glu Leu Leu Glu Pro Ile Ala
                565                 570                 575

Asp Gly Phe Arg Asn Tyr Arg Ala Arg Leu Asp Val Ser Thr Thr Glu
                580                 585                 590

Ser Leu Leu Ile Asp Lys Ala Gln Gln Leu Thr Leu Thr Ala Pro Glu
                595                 600                 605

Met Thr Ala Leu Val Gly Gly Met Arg Val Leu Gly Ala Asn Phe Asp
610                 615                 620

Gly Ser Lys Asn Gly Val Phe Thr Asp Arg Val Gly Val Leu Ser Asn
625                 630                 635                 640

Asp Phe Phe Val Asn Leu Leu Asp Met Arg Tyr Glu Trp Lys Ala Thr
                645                 650                 655

Asp Glu Ser Lys Glu Leu Phe Glu Gly Arg Asp Arg Glu Thr Gly Glu
                660                 665                 670

Val Lys Phe Thr Ala Ser Arg Ala Asp Leu Val Phe Gly Ser Asn Ser
                675                 680                 685

Val Leu Arg Ala Val Ala Glu Val Tyr Ala Ser Ser Asp Ala His Glu
690                 695                 700
```

```
Lys Phe Val Lys Asp Phe Val Ala Ala Trp Val Lys Val Met Asn Leu
705                 710                 715                 720

Asp Arg Phe Asp Leu Leu
                725

<210> SEQ ID NO 33
<211> LENGTH: 6329
<212> TYPE: DNA
<213> ORGANISM: Artificial sequence
<220> FEATURE:
<223> OTHER INFORMATION: Plasmid pKD46

<400> SEQUENCE: 33
catcgattta ttatgacaac ttgacggcta catcattcac tttttcttca caaccggcac      60
ggaactcgct cgggctggcc ccggtgcatt ttttaaatac ccgcgagaaa tagagttgat     120
cgtcaaaacc aacattgcga ccgacggtgg cgataggcat ccgggtggtg ctcaaaagca     180
gcttcgcctg gctgatacgt tggtcctcgc gccagcttaa gacgctaatc cctaactgct     240
ggcggaaaag atgtgacaga cgcgacggcg acaagcaaac atgctgtgcg acgctggcga     300
tatcaaaatt gctgtctgcc aggtgatcgc tgatgtactg acaagcctcg cgtacccgat     360
tatccatcgg tggatggagc gactcgttaa tcgcttccat gcgccgcagt aacaattgct     420
caagcagatt tatcgccagc agctccgaat agcgcccttc cccttgcccg gcgttaatga     480
tttgcccaaa caggtcgctg aaatgcggct ggtgcgcttc atccgggcga agaaccccg     540 tattggcaaa tattgacggc cagttaagcc attcatgcca gtaggcgcgc ggacgaaagt     600
aaacccactg gtgataccat tcgcgagcct ccggatgacg accgtagtga tgaatctctc     660
ctggcgggaa cagcaaaata tcacccggtc ggcaaacaaa ttctcgtccc tgatttttca     720
ccaccccctg accgcgaatg gtgagattga gaatataacc tttcattccc agcggtcggt     780
cgataaaaaa atcgagataa ccgttggcct caatcggcgt taaacccgcc accagatggg     840
cattaaacga gtatcccggc agcaggggat cattttgcgc ttcagccata cttttcatac     900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa agtgtctcta atcacggca    1080 gaaaagtcca cattgattat ttgcacggcg tcacactttg ctatgccata gcatttttat    1140
ccataagatt agcggatcct acctgacgct ttttatcgca actctctact gtttctccat    1200
acccgttttt tgggaattc gagctctaag gaggttataa aaatggata ttaatactga    1260 aactgagatc aagcaaaagc attcactaac ccccttcct gttttcctaa tcagcccggc    1320
atttcgcggg cgatattttc acagctattt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacgg ggccagcaaa aaatccatta cccgtgcgtt    1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
tttcctgata agcagaatgg catcgttccg gtggtgggcg ttgatggctg gtcccgcatc    1920
```

```
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacggggcc gtggcagtcg   2100
catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acaggggat gatgcgtggc   2520
acaaattacg gctcggcgtc atcaccgctt cagaagttca caacgtgata gcaaaacccc   2580
gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
tcatctatcg cgacgaaagt atgcgtaccg cctgctctcc cgatggttta tgcagtgacg   2820
gcaacggcct tgaactgaaa tgcccgttta cctcccggga tttcatgaag ttccggctcg   2880
gtggtttcga ggccataaag tcagcttaca tggcccaggt gcagtacagc atgtgggtga   2940
cgcgaaaaaa tgcctggtac tttgccaact atgacccgcg tatgaagcgt gaaggcctgc   3000
attatgtcgt gattgagcgg gatgaaaagt acatggcgag ttttgacgag atcgtgccgg   3060
agttcatcga aaaaatggac gaggcactgg ctgaaattgg ttttgtattt ggggagcaat   3120
ggcgatgacg catcctcacg ataatatccg ggtaggcgca atcactttcg tctactccgt   3180
tacaaagcga ggctgggtat ttcccggcct tctgttatc cgaaatccac tgaaagcaca   3240
gcggctggct gaggagataa ataataacg aggggctgta tgcacaaagc atcttctgtt   3300
gagttaagaa cgagtatcga gatggcacat agccttgctc aaattggaat caggtttgtg   3360
ccaataccag tagaaacaga cgaagaatcc atgggtatgg acagttttcc ctttgatatg   3420
taacggtgaa cagttgttct acttttgttt gttagtcttg atgcttcact gatagataca   3480
agagccataa gaacctcaga tccttccgta tttagccagt atgttctcta gtgtggttcg   3540
ttgttttgc gtgagccatg agaacgaacc attgagatca tacttacttt gcatgtcact   3600
caaaattt gcctcaaaac tggtgagctg aattttgca gttaaagcat cgtgtagtgt   3660
ttttcttagt ccgttacgta ggtaggaatc tgatgtaatg gttgttggta ttttgtcacc   3720
attcatttt atctggttgt tctcaagttc ggttacgaga tccatttgtc tatctagttc   3780
aacttggaaa atcaacgtat cagtcgggcg gcctcgctta tcaaccacca atttcatatt   3840
gctgtaagtg tttaaatctt tacttattgg tttcaaaacc cattggttaa gccttttaaa   3900
ctcatggtag ttatttcaa gcattaacat gaacttaaat tcatcaaggc taatctctat   3960
atttgccttg tgagttttct tttgtgttag ttctttaat aaccactcat aaatcctcat   4020
agagtatttg ttttcaaaag acttaacatg ttccagatta tattttatga attttttaa   4080
ctggaaaaga taaggcaata tctcttcact aaaaactaat tctaattttt cgcttgagaa   4140
cttggcatag tttgtccact ggaaaatctc aaagcctta accaaggat tcctgatttc   4200
cacagttctc gtcatcagct ctctggttgc tttagctaat acaccataag cattttccct   4260
actgatgttc atcatctgag cgtattggtt ataagtgaac gataccgtcc gttctttcct   4320
```

```
tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc tttttccttt g agttgtgggt atctgtaaat tctgctagac   4560
ctttgctgga aaacttgtaa attctgctag accctctgta aattccgcta gacctttgtg    4620 tgttttttt gttatattc aagtggttat aatttataga ataagaaag aataaaaaaa        4680 gataaaaaga atagatccca gccctgtgta taactcacta ctttagtcag ttccgcagta    4740
ttacaaaagg atgtcgcaaa cgctgtttgc tcctctacaa aacagacctt aaaaccctaa    4800
aggcttaagt agcaccctcg caagctcggt tgcggccgca atcgggcaaa tcgctgaata    4860
ttccttttgt ctccgaccat caggcacctg agtcgctgtc ttttcgtga cattcagttc      4920 gctgcgctca cggctctggc agtgaatggg ggtaaatggc actacaggcg cctttttatgg   4980 attcatgcaa ggaaactacc cataatacaa gaaaagcccg tcacgggctt ctcagggcgt    5040
tttatggcgg gtctgctatg tggtgctatc tgactttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760
tagctccttc ggtcctccga tcgttgtcag aagtaagttg gccgcagtgt tatcactcat    5820
ggttatggca gcactgcata attctcttac tgtcatgcca tccgtaagat gcttttctgt    5880
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tcttttactt tcaccagcgt    6120
ttctgggtga gcaaaaacag gaaggcaaaa tgccgcaaaa aagggaataa gggcgacacg    6180
gaaatgttga atactcatac tcttcctttt tcaatattat tgaagcattt atcagggtta    6240
ttgtctcatg agcggataca tatttgaatg tatttagaaa aataaacaaa tagggggttcc    6300 gcgcacattt ccccgaaaag tgccacctg                                       6329
```

<210> SEQ ID NO 34
<211> LENGTH: 25
<212> TYPE: DNA
<213> ORGANISM: Artificial sequence
<220> FEATURE:
<223> OTHER INFORMATION: Primer

<400> SEQUENCE: 34
aacaatatgt aagatctcaa ctatc                                            25

<210> SEQ ID NO 35
<211> LENGTH: 25
<212> TYPE: DNA
<213> ORGANISM: Artificial sequence
<220> FEATURE:
<223> OTHER INFORMATION: Primer

<400> SEQUENCE: 35
cagacatgag agatccagtg tgtag                                          25

<210> SEQ ID NO 36
<211> LENGTH: 9332
<212> TYPE: DNA
<213> ORGANISM: Artificial sequence
<220> FEATURE:
<223> OTHER INFORMATION: Plasmid pCP20

<400> SEQUENCE: 36
gagacacaac gtggctttgt tgaataaatc gaacttttgc tgagttgaag gatcagatca      60
cgcatcttcc cgacaacgca gaccgttccg tggcaaagca aaagttcaaa atcaccaact    120
ggtccaccta caacaaagct ctcatcaacc gtggctccct cactttctgg ctggatgatg    180
gggcgattca ggcctggtat gagtcagcaa caccttcttc acgaggcaga cctcagcgcc    240
acaggtgcgg ttgctggcgc taaccgtttt tatcaggctc tgggaggcag aataaatgat    300
catatcgtca attattacct ccacggggag agcctgagca aactggcctc aggcatttga    360
gaagcacacg gtcacactgc ttccggtagt caataaaccg gtaaaccagc aatagacata    420
agcggctatt taacgaccct gccctgaacc gacgaccggg tcgaatttgc tttcgaattt    480
ctgccattca tccgcttatt atcacttatt caggcgtagc aaccaggcgt ttaagggcac    540
caataactgc cttaaaaaaa ttacgccccg ccctgccact catcgcagta ctgttgtaat    600
tcattaagca ttctgccgac atggaagcca tcacaaacgg catgatgaac ctgaatcgcc    660
agcggcatca gcaccttgtc gccttgcgta taatatttgc ccatggtgaa acgggggcg    720 aagaagttgt ccatattggc cacgtttaaa tcaaaactgg tgaaactcac ccagggattg    780
gctgagacga aaaacatatt ctcaataaac cctttaggga ataggccag gttttcaccg    840 taacacgcca catcttgcga atatatgtgt agaaactgcc ggaaatcgtc gtggtattca    900
ctccagagcg atgaaaacgt ttcagtttgc tcatggaaaa cggtgtaaca agggtgaaca    960
ctatcccata tcaccagctc accgtctttc attgccatac ggaattccgg atgagcattc   1020
atcaggcggg caagaatgtg aataaaggcc ggataaaact tgtgcttatt tttctttacg   1080
gtctttaaaa aggccgtaat atccagctga acggtctggt tataggtaca ttgagcaact   1140
gactgaaatg cctcaaaatg ttctttacga tgccattggg atatatcaac ggtggtatat   1200
ccagtgattt ttttctccat tttagcttcc ttagctcctg aaaatctcga taactcaaaa   1260
aatacgcccg gtagtgatct tatttcatta tggtgaaagt tggaacctct tacgtgccga   1320
tcaacgtctc attttcgcca aaagttggcc cagggcttcc cggtatcaac agggacacca   1380
ggatttattt attctgcgaa gtgatcttcc gtcacaggta tttattcggc gcaaagtgcg   1440
tcgggtgatg ctgccaactt actgatttag tgtatgatgg tgttttgag gtgctccagt   1500 ggcttctgtt tctatcagct gtccctcctg ttcagctact gacggggtgg tgcgtaacgg   1560
caaaagcacc gccggacatc agcgcttgtt tcggcgtggg tatggtggca ggcccgtgg   1620 ccggggact gttgggcgcc tgtagtgcca tttaccccca ttcactgcca gagccgtgag   1680
cgcagcgaac tgaatgtcac gaaaaagaca gcgactcagg tgcctgatgg tcggagacaa   1740

```
aaggaatatt cagcgatttg cccgagcttg cgagggtgct acttaagcct ttagggtttt    1800
aaggtctgtt ttgtagagga gcaaacagcg tttgcgacat cctttttgtaa tactgcggaa   1860 ctgactaaag tagtgagtta tacacagggc tgggatctat tcttttttatc ttttttttatt 1920 ctttcttttat tctataaatt ataaccactt gaatataaac aaaaaaaaca cacaaaggtc   1980
tagcggaatt tacagagggt ctagcagaat ttacaagttt tccagcaaag gtctagcaga   2040
atttacagat acccacaact caaaggaaaa ggactagtaa ttatcattga ctagcccatc   2100
tcaattggta tagtgattaa aatcacctag accaattgag atgtatgtct gaattagttg   2160
ttttcaaagc aaatgaacta gcgattagtc gctatgactt aacggagcat gaaaccaagc   2220
taattttatg ctgtgtggca ctactcaacc ccacgattga aaaccctaca aggaaagaac   2280
ggacggtatc gttcacttat aaccaatacg ttcagatgat gaacatcagt agggaaaatg   2340
cttatggtgt attagctaaa gcaaccagag agctgatgac gagaactgtg gaaatcagga   2400
atcctttggt taaaggcttt gagattttcc agtggacaaa ctatgccaag ttctcaagcg   2460
aaaaattaga attagttttt agtgaagaga tattgcctta tcttttccag ttaaaaaaat   2520
tcataaaata taatctggaa catgttaagt cttttgaaaa caaatactct atgaggattt   2580
atgagtggtt attaaaagaa ctaacacaaa agaaaactca caggcaaat atagagatta    2640 gccttgatga atttaagttc atgttaatgc ttgaaaataa ctaccatgag tttaaaaggc   2700
ttaaccaatg ggttttgaaa ccaataagta aagatttaaa cacttacagc aatatgaaat   2760
tggtggttga taagcgaggc cgcccgactg atacgttgat tttccaagtt gaactagata   2820
gacaaatgga tctcgtaacc gaacttgaga acaaccagat aaaaatgaat ggtgacaaaa   2880
taccaacaac cattacatca gattcctacc tacataacgg actaagaaaa acactacacg   2940
atgctttaac tgcaaaaatt cagctcacca gttttgaggc aaaattttg agtgacatgc    3000 aaagtaagta tgatctcaat ggttcgttct catggctcac gcaaaaacaa cgaaccacac   3060
tagagaacat actggctaaa tacgaaggga tctgaggttc ttatggctct tgtatctatc   3120
agtgaagcat caagactaac aaacaaaagt agaacaactg ttcaccgtta catatcaaag   3180
ggaaaactgt ccatatgcac agatgaaaac ggtgtaaaaa agatagatac atcagagctt   3240
ttacgagttt ttggtgcatt taaagctgtt caccatgaac agatcgacaa tgtaacagat   3300
gaacagcatg taacacctaa tagaacaggt gaaaccagta aaacaaagca actagaacat   3360
gaaattgaac acctgagaca acttgttaca gctcaacagt cacacataga cagcctgaaa   3420
caggcgatgc tgcttatcga atcaaagctg ccgacaacac gggagccagt gacgcctccc   3480
gtggggaaaa aatcatggca attctggaag aaatagcgcc tgtttcgttt caggcaggtt   3540
atcagggagt gtcagcgtcc tgcggttctc cggggcgttc gggtcatgca gcccgtaatg   3600
gtgatttacc agcgtctgcc aggcatcaat tctaggcctg tctgcgcggt cgtagtacgg   3660
ctggaggcgt tttccggtct gtagctccat gttcggaatg acaaaattca gctcaagccg   3720
tcccttgtcc tggtgctcca cccacaggat gctgtactga ttttttttcga gaccgggcat   3780 cagtacacgc tcaaagctcg ccatcacttt ttcacgtcct cccggcggca gctccttctc   3840
cgcgaacgac agaacaccgg acgtgtattt cttcgcaaat ggcgtggcat cgatgagttc   3900
ccggacttct tccggattac cctgaagcac cgttgcgcct tcgcggttac gctccctccc   3960
cagcaggtaa tcaaccggac cactgccacc accttttccc ctggcatgaa atttaactat   4020
catcccgcgc cccctgttcc ctgacagcca gacgcagccg cgcagctca tcccgatgg    4080 ccatcagtgc ggccaccacc tgaacccggt caccggaaga ccactgcccg ctgttcacct   4140
```

```
tacgggctgt ctgattcagg ttatttccga tggcggccag ctgacgcagt aacggcggtg   4200
ccagtgtcgg cagttttccg gaacgggcaa ccggctcccc caggcagacc cgccgcatcc   4260
ataccgccag ttgtttaccc tcacagcgtt caagtaaccg ggcatgttca tcatcagtaa   4320
cccgtattgt gagcatcctc tcgcgtttca tcggtatcat tacccatga acagaaatcc    4380 cccttacacg gaggcatcag tgactaaacg gggtctgacg ctcagtggaa cgaaaactca   4440
cgttaaggga ttttggtcat gagattatca aaaaggatct tcacctagat ccttttaaat   4500
taaaaatgaa gttttaaatc aatctaaagt atatatgagt aaacttggtc tgacagttac   4560
caatgcttaa tcagtgaggc acctatctca gcgatctgtc tatttcgttc atccatagtt   4620
gcctgactcc ccgtcgtgta gataactacg atacgggagg gcttaccatc tggccccagt   4680
gctgcaatga taccgcgaga cccacgctca ccggctccag atttatcagc aataaaccag   4740
ccagccggaa gggccgagcg cagaagtggt cctgcaactt tatccgcctc catccagtct   4800
attaattgtt gccgggaagc tagagtaagt agttcgccag ttaatagttt gcgcaacgtt   4860
gttgccattg ctgcaggcat cgtggtgtca cgctcgtcgt ttggtatggc ttcattcagc   4920
tccggttccc aacgatcaag gcgagttaca tgatccccca tgttgtgcaa aaaagcggtt   4980
agctccttcg gtcctccgat cgttgtcaga agtaagttgg ccgcagtgtt atcactcatg   5040
gttatggcag cactgcataa ttctcttact gtcatgccat ccgtaagatg cttttctgtg   5100
actggtgagt actcaaccaa gtcattctga gaatagtgta tgcggcgacc gagttgctct   5160
tgcccggcgt caacacggga taataccgcg ccacatagca gaactttaaa agtgctcatc   5220
attggaaaac gttcttcggg gcgaaaactc tcaaggatct taccgctgtt gagatccagt   5280
tcgatgtaac ccactcgtgc acccaactga tcttcagcat cttttacttt caccagcgtt   5340
tctgggtgag caaaaacagg aaggcaaaat gccgcaaaaa agggaataag ggcgacacgg   5400
aaatgttgaa tactcatact cttcctttt caatattatt gaagcattta tcagggttat    5460
tgtctcatga gcggatacat atttgaatgt atttagaaaa ataaacaaat aggggttccg   5520
cgcacatttc cccgaaaagt gccacctgac gtctaagaaa ccattattat catgacatta   5580
acctataaaa ataggcgtat cacgaggccc tttcgtcttc aagaatttta taaaccgtgg   5640
agcgggcaat actgagctga tgagcaattt ccgttgcacc agtgcccttc tgatgaagcg   5700
tcagcacgac gttcctgtcc acggtacgcc tgcggccaaa tttgattcct ttcagctttg   5760
cttcctgtcg gccctcattc gtgcgctcta ggatcctcta cgccggacgc atcgtggccg   5820
gcatcaccgg cgctgaggtc tgcctcgtga agaaggtgtt gctgactcat accaggcctg   5880
aatcgcccca tcatccagcc agaaagtgag ggagccacgg ttgatgagag ctttgttgta   5940 ggtgaccag ttggtgattt tgaacttttg ctttgccacg gaacggtctg cgttgtcggg    6000
aagatgcgtg atctgatcct tcaactcagc aaaagttcga tttattcaac aaagccgccg   6060
tcccgtcaag tcagcgtaat gctctgccag tgttacaacc aattaaccaa ttctgattag   6120
aaaaactcat cgagcatcaa atgaaactgc aatttattca tatcaggatt atcaatacca   6180 tattttgaa aaagccgttt ctgtaatgaa ggagaaaact caccgaggca gttccatagg    6240
atggcaagat cctggtatcg gtctgcgatt ccgactcgtc aacatcaat acaacctatt    6300 aatttcccct cgtcaaaaat aaggttatca agtgagaaat caccatgagt gacgactgaa   6360
tccggtgaga atggcagaat aggaacttcg gaataggaac ttcaaagcgt ttccgaaaac   6420
gagcgcttcc gaaaatgcaa cgcgagctgc gcacatacag ctcactgttc acgtcgcacc   6480
tatatctgcg tgttgcctgt atatatatat acatgagaag aacggcatag tgcgtgttta   6540
```

```
tgcttaaatg cgtacttata tgcgtctatt tatgtaggat gaaaggtagt ctagtacctc    6600
ctgtgatatt atcccattcc atgcggggta tcgtatgctt ccttcagcac tacccttag     6660 ctgttctata tgctgccact cctcaattgg attagtctca tccttcaatg ctatcatttc    6720
ctttgatatt ggatcatatg catagtaccg agaaactagt gcgaagtagt gatcaggtat    6780
tgctgttatc tgatgagtat acgttgtcct ggccacggca gaagcacgct tatcgctcca    6840
atttcccaca acattagtca actccgttag gcccttcatt gaaagaaatg aggtcatcaa    6900
atgtcttcca atgtgagatt ttgggccatt ttttatagca aagattgaat aaggcgcatt    6960
tttcttcaaa gctttattgt acgatctgac taagttatct tttaataatt ggtattcctg    7020
tttattgctt gaagaattgc cggtcctatt tactcgtttt aggactggtt cagaattcct    7080
caaaaattca tccaaatata caagtggatc gatcctaccc cttgcgctaa agaagtatat    7140
gtgcctacta acgcttgtct ttgtctctgt cactaaacac tggattatta ctcccagata    7200
cttattttgg actaatttaa atgatttcgg atcaacgttc ttaatatcgc tgaatcttcc    7260
acaattgatg aaagtagcta ggaagaggaa ttggtataaa gttttgtttt ttgtaaatct    7320
cgaagtatac tcaaacgaat ttagtatttt ctcagtgatc tcccagatgc tttcaccctc    7380
acttagaagt gctttaagca ttttttttact gtggctattt cccttatctg cttcttccga    7440
tgattcgaac tgtaattgca aactacttac aatatcagtg atatcagatt gatgttttg     7500 tccatagtaa ggaataattg taaattccca agcaggaatc aatttcttta atgaggcttc    7560
cagaattgtt gcttttttgcg tcttgtattt aaactggagt gatttattga caatatcgaa    7620
actcagcgaa ttgcttatga tagtattata gctcatgaat gtggctctct tgattgctgt    7680
tccgttatgt gtaatcatcc aacataaata ggttagttca gcagcacata atgctatttt    7740
ctcacctgaa ggtctttcaa acctttccac aaactgacga acaagcacct taggtggtgt    7800
tttacataat atatcaaatt gtggcataca acctccttag tacatgcaac cattatcacc    7860
gccagaggta aaatagtcaa cacgcacggt gttagatatt tatcccttgc ggtgatagat    7920
ttaacgtatg agcacaaaaa agaaaccatt aacacaagag cagcttgagg acgcacgtcg    7980
ccttaaagca atttatgaaa aaagaaaaa tgaacttggc ttatcccagg aatctgtcgc    8040
agacaagatg gggatggggc agtcaggcgt tggtgcttta tttaatggca tcaatgcatt    8100
aaatgcttat aacgccgcat tgcttacaaa aattctcaaa gttagcgttg aagaatttag    8160
cccttcaatc gccagagaaa tctacgagat gtatgaagcg gttagtatgc agccgtcact    8220
tagaagtgag tatgagtacc ctgttttttc tcatgttcag gcaggatgt tctcacctaa      8280 gcttagaacc tttaccaaag gtgatgcgga gagatgggta agcacaacca aaaaagccag    8340
tgattctgca ttctggcttg aggttgaagg taattccatg accgcaccaa caggctccaa    8400
gccaagcttt cctgacggaa tgttaattct cgttgaccct gagcaggctg ttgagccagg    8460
tgatttctgc atagccagac ttgggggtga tgagtttacc ttcaagaaac tgatcaggga    8520
tagcggtcag gtgttttttac aaccactaaa cccacagtac ccaatgatcc catgcaatga    8580
gagttgttcc gttgtgggga agttatcgc tagtcagtgg cctgaagaga cgtttggctg      8640
atcggcaagg tgttctggtc ggcgcatagc tgataacaat tgagcaagaa tctgcatttc    8700
tttccagact tgttcaacag gccagccatt acgctcgtca tcaaaatcac tcgcatcaac    8760
caaaccgtta ttcattcgtg attgcgcctg agcgagacga aatacgcgat cgctgttaaa    8820
aggacaatta caaacaggaa tcgaatgcaa ccggcgcagg aacactgcca gcgcatcaac    8880
aatattttca cctgaatcag gatattcttc taataccctgg aatgctgttt tcccggggat    8940
```

```
cgcagtggtg agtaaccatg catcatcagg agtacggata aaatgcttga tggtcggaag    9000
aggcataaat tccgtcagcc agtttagtct gaccatctca tctgtaacat cattggcaac    9060
gctacctttg ccatgtttca gaaacaactc tggcgcatcg ggcttcccat acaatcgata    9120
gattgtcgca cctgattgcc cgacattatc gcgagcccat ttatacccat ataaatcagc    9180
atccatgttg gaatttaatc gcggcctcga gcaagacgtt tcccgttgaa tatggctcat    9240 aacaccccctt gtattactgt ttatgtaagc agacagtttt attgttcatg atgatatatt    9300
tttatcttgt gcaatgtaac atcagagatt tt                                  9332
```

<210> SEQ ID NO 37
<211> LENGTH: 80
<212> TYPE: DNA
<213> ORGANISM: Artificial sequence
<220> FEATURE:
<223> OTHER INFORMATION: Primer

<400> SEQUENCE: 37

```
atgtcgcaac ataacgaaaa gaacccacat cagcaccagt caccactaca cgattccagc    60
gtgtaggctg gagctgcttc                                                80
```

<210> SEQ ID NO 38
<211> LENGTH: 82
<212> TYPE: DNA
<213> ORGANISM: Artificial sequence
<220> FEATURE:
<223> OTHER INFORMATION: Primer

<400> SEQUENCE: 38

```
ttacgccggg attttgtcaa tcttaggaat gcgtgaccac acgcggtgtg ctgtcatcag    60
attccgggga tccgtcgacc tg                                             82
```

<210> SEQ ID NO 39
<211> LENGTH: 1424
<212> TYPE: DNA
<213> ORGANISM: Artificial sequence
<220> FEATURE:
<223> OTHER INFORMATION: Synthetic construct

<400> SEQUENCE: 39

```
ttacgccggg attttgtcaa tcttaggaat gcgtgaccac acgcggtgtg ctgtcatcag    60
attccgggga tccgtcgacc tgcagttcga agttcctatt ctctagaaag tataggaact   120
tcagagcgct tttgaagctc acgctgccgc aagcactcag ggcgcaaggg ctgctaaagg   180
aagcggaaca cgtagaaagc cagtccgcag aaacggtgct gaccccggat gaatgtcagc   240
tactgggcta tctggacaag ggaaaacgca agcgcaaaga gaaagcaggt agcttgcagt   300
gggcttacat ggcgatagct agactgggcg gttttatgga cagcaagcga accggaattg   360
ccagctgggg cgccctctgg taaggttggg aagccctgca agtaaactg atggctttc     420 ttgccgccaa ggatctgatg gcgcagggga tcaagatctg atcaagagac aggatgagga   480
tcgtttcgca tgattgaaca agatggattg cacgcaggtt ctccggccgc ttgggtggag   540
aggctattcg gctatgactg ggcacaacag acaatcggct gctctgatgc cgccgtgttc   600
cggctgtcag cgcaggggcg cccggttctt tttgtcaaga ccgacctgtc cggtgccctg   660
aatgaactgc aggacgaggc agcgcggcta tcgtggctgg ccacgacggg cgttccttgc   720
gcagctgtgc tcgacgttgt cactgaagcg ggaagggact ggctgctatt gggcgaagtg   780
ccggggcagg atctcctgtc atctcacctt gctcctgccg agaaagtatc catcatggct   840
```

| | |
|---|---|
| gatgcaatgc ggcggctgca tacgcttgat ccggctacct gcccattcga ccaccaagcg | 900 |
| aaacatcgca tcgagcgagc acgtactcgg atggaagccg gtcttgtcga tcaggatgat | 960 |
| ctggacgaag agcatcaggg gctcgcgcca gccgaactgt cgccaggct caaggcgcgc | 1020 |
| atgcccgacg gcgaggatct cgtcgtgacc catggcgatg cctgcttgcc gaatatcatg | 1080 |
| gtggaaaatg gccgcttttc tggattcatc gactgtggcc ggctgggtgt ggcggaccgc | 1140 |
| tatcaggaca tagcgttggc tacccgtgat attgctgaag agcttggcgg cgaatgggct | 1200 |
| gaccgcttcc tcgtgcttta cggtatcgcc gctcccgatt cgcagcgcat cgccttctat | 1260 |
| cgccttcttg acgagttctt ctaataaggg gatcttgaag ttcctattcc gaagttccta | 1320 |
| ttctctagaa agtataggaa cttcgaagca gctccagcct acacgctgga atcgtgtagt | 1380 |
| ggtgactggt gctgatgtgg gttcttttcg ttatgttgcg acat | 1424 |

<210> SEQ ID NO 40
<211> LENGTH: 2262
<212> TYPE: DNA
<213> ORGANISM: Escherichia coli

<400> SEQUENCE: 40

| | |
|---|---|
| atgtcgcaac ataacgaaaa gaacccacat cagcaccagt caccactaca cgattccagc | 60 |
| gaagcgaaac cggggatgga ctcactggca cctgaggacg gctctcatcg tccagcggct | 120 |
| gaaccaacac cgccaggtgc acaacctacc gccccaggga gcctgaaagc ccctgatacg | 180 |
| cgtaacgaaa aacttaattc tctggaagac gtacgcaaag gcagtgaaaa ttatgcgctg | 240 |
| accactaatc agggcgtgcg catcgccgac gatcaaaact cactgcgtgc cggtagccgt | 300 |
| ggtccaacgc tgctggaaga ttttattctg cgcgagaaaa tcacccactt tgaccatgag | 360 |
| cgcattccgg aacgtattgt tcatgcacgc ggatcagccg ctcacggtta tttccagcca | 420 |
| tataaaagct taagcgatat taccaaagcg gatttcctct cagatccgaa caaaatcacc | 480 |
| ccagtatttg tacgtttctc taccgttcag ggtggtgctg gctctgctga taccgtgcgt | 540 |
| gatatccgtg gctttgccac caagttctat accgaagagg gtattttga cctcgttggc | 600 |
| aataacacgc caatcttctt tatccaggat gcgcataaat tccccgattt tgttcatgcg | 660 |
| gtaaaaccag aaccgcactg ggcaattcca caagggcaaa gtgcccacga tactttctgg | 720 |
| gattatgttt ctctgcaacc tgaaactctg cacaacgtga tgtgggcgat gtcggatcgc | 780 |
| ggcatccccc gcagttaccg caccatggaa ggcttcggta ttcacacctt ccgcctgatt | 840 |
| aatgccgaag gaaggcaac gtttgtacgt ttccactgga accactggc aggtaaagcc | 900 |
| tcactcgttt gggatgaagc acaaaaactc accggacgtg acccggactt ccaccgccgc | 960 |
| gagttgtggg aagccattga agcaggcgat tttccggaat acgaactggg cttccagttg | 1020 |
| attcctgaag aagatgaatt caagttcgac ttcgatcttc tcgatccaac caaacttatc | 1080 |
| ccggaagaac tggtgcccgt tcagcgtgtc ggcaaaatgg tgctcaatcg caacccggat | 1140 |
| aacttctttg ctgaaaacga acaggcggct ttccatcctg gcatatcgt gccgggactg | 1200 |
| gacttcacca acgatccgct gttgcaggga cgtttgttct cctataccga tacacaaatc | 1260 |
| agtcgtcttg gtgggccgaa tttccatgag attccgatta accgtccgac ctgcccttac | 1320 |
| cataatttcc agcgtgacgg catgcatcgc atggggatcg acactaaccc ggcgaattac | 1380 |
| gaaccgaact cgattaacga taactggccg cgcgaaacac cgccggggcc gaaacgcggc | 1440 |
| ggttttgaat cataccagga gcgcgtggaa ggcaataaag ttcgcgagcg cagcccatcg | 1500 |
| tttggcgaat attattccca tccgcgtctg ttctggctaa gtcagacgcc atttgagcag | 1560 |

-continued

```
cgccatattg tcgatggttt cagttttgag ttaagcaaag tcgttcgtcc gtatattcgt    1620
gagcgcgttg ttgaccagct ggcgcatatt gatctcactc tggcccaggc ggtggcgaaa    1680
aatctcggta tcgaactgac tgacgaccag ctgaatatca ccccacctcc ggacgtcaac    1740
ggtctgaaaa aggatccatc cttaagtttg tacgccattc ctgacggtga tgtgaaaggt    1800
cgcgtggtag cgattttact taatgatgaa gtgagatcgg cagaccttct ggccattctc    1860
aaggcgctga aggccaaagg cgttcatgcc aaactgctct actcccgaat gggtgaagtg    1920
actgcggatg acggtacggt gttgcctata gccgctacct tgccggtgc accttcgctg     1980 acggtcgatg cggtcattgt cccttgcggc aatatcgcgg atatcgctga caacggcgat    2040
gccaactact acctgatgga agcctacaaa caccttaaac cgattgcgct ggcgggtgac    2100
gcgcgcaagt ttaaagcaac aatcaagatc gctgaccagg gtgaagaagg gattgtggaa    2160
gctgacagcg ctgacggtag ttttatggat gaactgctaa cgctgatggc agcacaccgc    2220
gtgtggtcac gcattcctaa gattgacaaa attcctgcct ga                      2262
```

<210> SEQ ID NO 41
<211> LENGTH: 753
<212> TYPE: PRT
<213> ORGANISM: Escherichia coli

<400> SEQUENCE: 41

```
Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
                20                  25                  30

Asp Gly Ser His Arg Pro Ala Ala Glu Pro Thr Pro Pro Gly Ala Gln
            35                  40                  45

Pro Thr Ala Pro Gly Ser Leu Lys Ala Pro Asp Thr Arg Asn Glu Lys
        50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255
```

-continued

```
Met Ser Asp Arg Gly Ile Pro Arg Ser Tyr Arg Thr Met Glu Gly Phe
            260                 265                 270
Gly Ile His Thr Phe Arg Leu Ile Asn Ala Glu Gly Lys Ala Thr Phe
            275                 280                 285
Val Arg Phe His Trp Lys Pro Leu Ala Gly Lys Ala Ser Leu Val Trp
290                 295                 300
Asp Glu Ala Gln Lys Leu Thr Gly Arg Asp Pro Asp Phe His Arg Arg
305                 310                 315                 320
Glu Leu Trp Glu Ala Ile Glu Ala Gly Asp Phe Pro Glu Tyr Glu Leu
                325                 330                 335
Gly Phe Gln Leu Ile Pro Glu Glu Asp Glu Phe Lys Asp Phe Asp
                340                 345                 350
Leu Leu Asp Pro Thr Lys Leu Ile Pro Glu Glu Leu Val Pro Val Gln
            355                 360                 365
Arg Val Gly Lys Met Val Leu Asn Arg Asn Pro Asp Asn Phe Phe Ala
            370                 375                 380
Glu Asn Glu Gln Ala Ala Phe His Pro Gly His Ile Val Pro Gly Leu
385                 390                 395                 400
Asp Phe Thr Asn Asp Pro Leu Leu Gln Gly Arg Leu Phe Ser Tyr Thr
                405                 410                 415
Asp Thr Gln Ile Ser Arg Leu Gly Gly Pro Asn Phe His Glu Ile Pro
            420                 425                 430
Ile Asn Arg Pro Thr Cys Pro Tyr His Asn Phe Gln Arg Asp Gly Met
            435                 440                 445
His Arg Met Gly Ile Asp Thr Asn Pro Ala Asn Tyr Glu Pro Asn Ser
            450                 455                 460
Ile Asn Asp Asn Trp Pro Arg Glu Thr Pro Pro Gly Pro Lys Arg Gly
465                 470                 475                 480
Gly Phe Glu Ser Tyr Gln Glu Arg Val Glu Gly Asn Lys Val Arg Glu
                485                 490                 495
Arg Ser Pro Ser Phe Gly Glu Tyr Tyr Ser His Pro Arg Leu Phe Trp
            500                 505                 510
Leu Ser Gln Thr Pro Phe Glu Gln Arg His Ile Val Asp Gly Phe Ser
            515                 520                 525
Phe Glu Leu Ser Lys Val Val Arg Pro Tyr Ile Arg Glu Arg Val Val
530                 535                 540
Asp Gln Leu Ala His Ile Asp Leu Thr Leu Ala Gln Ala Val Ala Lys
545                 550                 555                 560
Asn Leu Gly Ile Glu Leu Thr Asp Asp Gln Leu Asn Ile Thr Pro Pro
                565                 570                 575
Pro Asp Val Asn Gly Leu Lys Lys Asp Pro Ser Leu Ser Leu Tyr Ala
            580                 585                 590
Ile Pro Asp Gly Asp Val Lys Gly Arg Val Val Ala Ile Leu Leu Asn
            595                 600                 605
Asp Glu Val Arg Ser Ala Asp Leu Leu Ala Ile Leu Lys Ala Leu Lys
            610                 615                 620
Ala Lys Gly Val His Ala Lys Leu Leu Tyr Ser Arg Met Gly Glu Val
625                 630                 635                 640
Thr Ala Asp Asp Gly Thr Val Leu Pro Ile Ala Ala Thr Phe Ala Gly
                645                 650                 655
Ala Pro Ser Leu Thr Val Asp Ala Val Ile Val Pro Cys Gly Asn Ile
            660                 665                 670
Ala Asp Ile Ala Asp Asn Gly Asp Ala Asn Tyr Tyr Leu Met Glu Ala
            675                 680                 685
```

```
Tyr Lys His Leu Lys Pro Ile Ala Leu Ala Gly Asp Ala Arg Lys Phe
        690                 695                 700

Lys Ala Thr Ile Lys Ile Ala Asp Gln Gly Glu Gly Ile Val Glu
705                 710                 715                 720

Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala
```

<210> SEQ ID NO 42
<211> LENGTH: 25
<212> TYPE: DNA
<213> ORGANISM: Artificial sequence
<220> FEATURE:
<223> OTHER INFORMATION: Primer

<400> SEQUENCE: 42
gatctgactg gtggtctata gttag                                    25

<210> SEQ ID NO 43
<211> LENGTH: 25
<212> TYPE: DNA
<213> ORGANISM: Artificial sequence
<220> FEATURE:
<223> OTHER INFORMATION: Primer

<400> SEQUENCE: 43
gtagttatca tgatgtgtaa gtaag                                    25

<210> SEQ ID NO 44
<211> LENGTH: 978
<212> TYPE: DNA
<213> ORGANISM: Thermotoga neapolitana

<400> SEQUENCE: 44
atggccttct tcgatatgcc ccttgaggaa ctgaaaaagt accggcctga aaggtacgag      60
gagaaagatt tcgatgagtt ctggagggaa acacttaaag aaagcgaagg attccctctg     120
gatcccgtct ttgaaaaggt ggactttcat ctcaaaacgg ttgaaacgta cgatgttact     180
ttctctggat acagggggca gagaataaag ggctggcttc ttgttccgaa gttggcggaa     240
gaaaagcttc catgcgtcgt gcagtacata ggttacaatg gtggaagggg ttttccacac     300
gactggctgt tctggccgtc aatgggttac atctgttttg tcatgacaca gggggcag      360
ggaagcggct ggatgaaggg agacacaccg gattaccctg agggtccagt cgatccacag     420
taccccggat tcatgacgag gggcattctg gatccgggaa cctattacta caggcgagtc     480
ttcgtggatg cggtcagggc ggtggaagca gccatttcct tcccgagagt ggattccagg     540
aaggtggtgg tggccggagg cagtcagggt ggggaatcg cccttgcggt gagtgccctg     600
tcgaacaggg tgaaggctct gctctgcgat gtgccgtttc tgtgccactt cagaagggcc     660
gtgcaacttg tcgacacaca cccatacgtg gagatcacca acttcctcaa acccacagg     720
gacaaagagg agattgtttt cagaacactt tcctacttcg atggtgtgaa ctttgcagca     780
agggcaaagg tgcccgccct gttttccgtt gggctcatgg acaccatctg tcctccctcg     840
acggtcttcg ccgcttacaa ccactacgcc ggtccaaagg agatcagaat ctatccgtac     900
aacaaccacg aaggtggagg ttctttccag gcaattgagc aggtgaaatt cttgaagaga     960
ctatttgagg aaggctag                                                  978

```
<210> SEQ ID NO 45
<211> LENGTH: 24
<212> TYPE: DNA
<213> ORGANISM: Artificial sequence
<220> FEATURE:
<223> OTHER INFORMATION: Primer

<400> SEQUENCE: 45
atggctttct tgacatgcc gctg                                              24

<210> SEQ ID NO 46
<211> LENGTH: 27
<212> TYPE: DNA
<213> ORGANISM: Artificial sequence
<220> FEATURE:
<223> OTHER INFORMATION: Primer

<400> SEQUENCE: 46
ttagccttct tcgaacaggc gtttcag                                          27

<210> SEQ ID NO 47
<211> LENGTH: 978
<212> TYPE: DNA
<213> ORGANISM: Thermotoga neapolitana

<400> SEQUENCE: 47
atggctttct tgacatgcc gctggaagaa ctgaaaaagt accgtccgga acgttacgag        60
gaaaaagact tgacgaatt ttggcgcgaa accctgaaag aatccgaggg tttcccactg       120
gacccggtat tgaaaaagt tgacttccac ctgaagaccg tcgaaactta cgacgtcacc       180
ttcagcggtt atcgtggcca gcgtatcaaa ggttggctgc tggtaccgaa actggcggaa     240
gagaaactgc cgtgtgttgt tcagtacatt ggttacaacg gtggccgtgg tttcccgcac     300
gactggctgt tctggccgtc tatgggttac atctgcttcg ttatggacac ccgtggtcag     360
ggtagcggtt ggatgaaggg tgatactccg gactacccgg aaggtccggt ggacccgcag     420 taccccgggct tcatgacgcg cggcatcctg atcctggca cctattacta ccgtcgtgtg     480
tttgtcgatg ccgtgcgcgc cgttgaagcc gctatcagct tcccacgcgt cgattctcgt     540
aaagtggtag ttgctggtgg ctctcaaggt ggcggcattg cactggcagt ttccgcgctg     600
tccaaccgtg ttaaagcccct gctgtgcgat gttccgttcc tgtgccactt ccgtcgtgcg     660
gtacagctgg tggacaccca cccgtacgta gaaattacga acttcctgaa aacccatcgt     720
gataaagaag agatcgtatt ccgtaccctg tcttactttg atggcgttaa ttttgcggct     780
cgtgcaaaag taccggcgct gttcagcgta ggtctgatgg acactattttg tccgccgtct     840 accgtattcg cagcctacaa ccactacgct ggtccgaaag aaatccgcat ctacccgtac    900
aacaaccacg aaggtggtgg ttcttttccag gcaatcgaac aggttaaatt cctgaaacgc    960
ctgttcgaag aaggctaa                                                  978

<210> SEQ ID NO 48
<211> LENGTH: 978
<212> TYPE: DNA
<213> ORGANISM: Thermotoga maritima

<400> SEQUENCE: 48
atggccttct tcgatttacc actcgaagaa ctgaagaaat atcgtccaga gcggtacgaa      60
gagaaagact tcgatgagtt ctgggaagag acactcgcag agagcgaaaa gttcccctta    120
gaccccgtct tcgagaggat ggagtctcac ctcaaaacag tcgaagcgta cgatgtcacc    180
ttctccggat acaggggaca gaggatcaaa gggtggctcc ttgttccaaa actggaagaa    240
```

```
gaaaaacttc cctgcgttgt gcagtacata ggatacaacg gtggaagagg attccctcac    300
gactggctgt tctggccttc tatgggttac atatgtttcg tcatggatac tcgaggtcag    360
ggaagcggct ggctgaaagg agacacaccg gattaccctg agggtcccgt tgaccctcag    420
tatccaggat tcatgacaag aggaatactg gatcccagaa cttactacta cagacgagtc    480
ttcacggacg ctgtcagagc cgttgaagct gctgcttctt ttcctcaggt agatcaagaa    540
agaatcgtga tagctggagg cagtcagggt ggcggaatag cccttgcggt gagcgctctc    600
tcaaagaaag caaaggctct tctgtgcgat gtgccgtttc tgtgtcactt cagaagagca    660
gtacagcttg tggatacgca tccatacgcg gagatcacga actttctaaa gacccacaga    720
gacaaggaag aaatcgtgtt caggactctt tcctatttcg atggagtgaa cttcgcagcc    780
agagcgaaga tccctgcgct gttttctgtg ggtctcatgg acaacatttg tcctccttca    840
acggttttcg ctgcctacaa ttactacgct ggaccgaagg aaatcagaat ctatccgtac    900
aacaaccacg agggaggagg ctcttttccaa gcggttgaac aggtgaaatt cttgaaaaaa    960
ctatttgaga aaggctaa                                                   978

<210> SEQ ID NO 49
<211> LENGTH: 49
<212> TYPE: DNA
<213> ORGANISM: Artificial sequence
<220> FEATURE:
<223> OTHER INFORMATION: Primer

<400> SEQUENCE: 49
taactgcagt aaggaggaat aggacatggg gttcttcgac ctgcctctg                 49

<210> SEQ ID NO 50
<211> LENGTH: 38
<212> TYPE: DNA
<213> ORGANISM: Artificial sequence
<220> FEATURE:
<223> OTHER INFORMATION: Primer

<400> SEQUENCE: 50
tgatctagat tagcccttct caaacagttt ctttcagg                             38

<210> SEQ ID NO 51
<211> LENGTH: 1012
<212> TYPE: DNA
<213> ORGANISM: Artificial sequence
<220> FEATURE:
<223> OTHER INFORMATION: Synthetic construct

<400> SEQUENCE: 51
taactgcagt aaggaggaat aggacatggc gttcttcgac ctgcctctgg aagaactgaa    60
gaaataccgt ccagagcgtt acgaagagaa ggacttcgac gagttctggg aggaaactct    120
ggcggagagc gaaaagtttc cgctggaccc agtgttcgag cgtatggaat ctcacctgaa    180
aaccgtggag gcatatgacg ttacttttc tggttaccgt ggccagcgta tcaaaggctg    240
gctgctggtt ccgaaactgg aggaagaaaa actgccgtgc gtagttcagt acatcggtta    300
caacggtggc cgtggctttc gcacgattg gctgttctgg ccgtctatgg gctacatttg    360
cttcgtcatg gatactcgtg gtcagggttc cggctggctg aaaggcgata ctccggatta    420
tccggagggc ccggtagacc cgcagtaccc tggcttcatg acgcgtggta ttctggatcc    480
gcgtacctat tactatcgcc gcgttttta cgatgcagtt cgtgccgtag aggccgcggc    540
ttctttccct caggttgacc aggagcgtat tgttatcgct ggtggctccc agggtggcgg    600
```

```
catcgccctg gcggtatctg cgctgagcaa gaaagctaag gcactgctgt gtgacgtccc    660
gttcctgtgt cacttccgtc gcgctgttca gctggtagat acccatccgt acgcggagat    720
tactaacttc ctgaaaactc accgcgacaa agaagaaatc gttttccgca ccctgtccta    780
tttcgacggc gttaacttcg cggctcgtgc aaaaattccg gcactgttct ctgttggtct    840
gatggacaac atctgccctc cttctaccgt tttcgcggca tataactatt atgcgggtcc    900
gaaagaaatc cgtatctatc cgtacaacaa ccacgaaggc ggtggtagct ttcaggctgt    960
tgaacaagtg aaattcctga gaaactgtt tgagaagggc taatctagat ca            1012

<210> SEQ ID NO 52
<211> LENGTH: 50
<212> TYPE: DNA
<213> ORGANISM: artificial sequence
<220> FEATURE:
<223> OTHER INFORMATION: primer

<400> SEQUENCE: 52
taactgcagt aaggaggaat aggacatggc cttcttcgat ttacccactc                50

<210> SEQ ID NO 53
<211> LENGTH: 38
<212> TYPE: DNA
<213> ORGANISM: artificial sequence
<220> FEATURE:
<223> OTHER INFORMATION: primer

<400> SEQUENCE: 53
tgatctagat tagcctttct caaatagttt tttcaaga                              38

<210> SEQ ID NO 54
<211> LENGTH: 1012
<212> TYPE: DNA
<213> ORGANISM: Thermotoga maritima

<400> SEQUENCE: 54
taactgcagt aaggaggaat aggacatggc cttcttcgat ttaccactcg aagaactgaa     60
gaaatatcgt ccagagcggt acgaagagaa agacttcgat gagttctggg aagagacact    120
cgcagagagc gaaaagttcc ccttagaccc cgtcttcgag aggatggagt ctcacctcaa    180
aacagtcgaa gcgtacgatg tcaccttctc cggatacagg ggacagagga tcaaagggtg    240
gctccttgtt ccaaaactgg aagaagaaaa acttccctgc gttgtgcagt acataggata    300
caacggtgga gaggattcc ctcacgactg gctgttctgg ccttctatgg gttacatatg    360
tttcgtcatg gatactcgag gtcagggaag cggctggctg aaaggagaca caccggatta    420
ccctgagggt cccgttgacc ctcagtatcc aggattcatg acaagaggaa tactggatcc    480
cagaacttac tactacagac gagtcttcac ggacgctgtc agagccgttg aagctgctgc    540
ttcttttcct caggtagatc aagaaagaat cgtgatagct ggaggcagtc agggtggcgg    600
aatagccctt gcggtgagcg ctctctcaaa gaaagcaaag gctcttctgt gcgatgtgcc    660
gtttctgtgt cacttcagaa gagcagtaca gcttgtggat acgcatccat acgcggagat    720
cacgaacttt ctaaagaccc acagagacaa ggaagaaatc gtgttcagga ctcttttccta    780 tttcgatgga gtgaacttcg cagccagagc gaagatccct gcgctgtttt ctgtgggtct    840
catggacaac atttgtcctc cttcaacggt tttcgctgcc tacaattact acgctggacc    900
gaaggaaatc agaatctatc cgtacaacaa ccacgaggga ggaggctctt ccaagcggt    960 tgaacaggtg aaattcttga aaaaactatt tgagaaaggc taatctagat ca            1012
```

```
<210> SEQ ID NO 55
<211> LENGTH: 47
<212> TYPE: DNA
<213> ORGANISM: Artificial Sequence
<220> FEATURE:
<223> OTHER INFORMATION: Primer

<400> SEQUENCE: 55
taagaattct aaggaatagg acatggcgtt tcttcgacct gcctctg         47

<210> SEQ ID NO 56
<211> LENGTH: 36
<212> TYPE: DNA
<213> ORGANISM: Artificial Sequence
<220> FEATURE:
<223> OTHER INFORMATION: Primer

<400> SEQUENCE: 56
aaactgcagt tagcccttct caaacagttt cttcag                     36

<210> SEQ ID NO 57
<211> LENGTH: 975
<212> TYPE: DNA
<213> ORGANISM: Artificial Sequence
<220> FEATURE:
<223> OTHER INFORMATION: Codon optimized sequence

<400> SEQUENCE: 57
atggcgttct tcgacctgcc tctggaagaa ctgaagaaat accgtccaga gcgttacgaa    60
gagaaggact cgacgagtt ctgggaggaa actctggcgg agagcgaaaa gtttccgctg    120
gacccagtgt tcgagcgtat ggaatctcac ctgaaaaccg tggaggcata tgacgttact    180
ttttctggtt accgtggcca gcgtatcaaa ggctggctgc tggttccgaa actggaggaa    240
gaaaaactgc cgtgcgtagt tcagtacatc ggttacaacg gtggccgtgg ctttccgcac    300
gattggctgt tctggccgtc tatgggctac atttgcttcg tcatggatac tcgtggtcag    360
ggttccggct ggctgaaagg cgatactccg gattatccgg agggcccggt agacccgcag    420
taccctggct tcatgacgcg tggtattctg gatccgcgta cctattacta tgccgcgtt    480 tttaccgatg cagttcgtgc cgtagaggcc gcggcttctt tccctcaggt tgaccaggag    540
cgtattgtta tcgctggtgg ctcccagggt ggcggcatcg ccctggcggt atctgcgctg    600
agcaagaaag ctaaggcact gctgtgtgac gtcccgttcc tgtgtcactt ccgtcgcgct    660
gttcagctgg tagatacca tccgtacgcg gagattacta acttcctgaa aactcaccgc    720
gacaaagaag aaatcgtttt ccgcacctg tcctatttcg acggcgttaa cttcgcggct    780
cgtgcaaaaa ttccggcact gttctctgtt ggtctgatgg acaacatctg ccctccttct    840
accgttttcg cggcatataa ctattatgcg ggtccgaaag aaatccgtat ctatccgtac    900
aacaaccacg aaggcggtgg tagctttcag gctgttgaac aagtgaaatt cctgaagaaa    960
ctgtttgaga agggc                                                   975

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
ggacaacatc gtgcctcctt cta                                            23
```

-continued

```
<210> SEQ ID NO 59
<211> LENGTH: 23
<212> TYPE: DNA
<213> ORGANISM: Artificial Sequence
<220> FEATURE:
<223> OTHER INFORMATION: Primer

<400> SEQUENCE: 59
tagaaggagg cacgatgttg tcc                                              23

<210> SEQ ID NO 60
<211> LENGTH: 23
<212> TYPE: DNA
<213> ORGANISM: Artificial Sequence
<220> FEATURE:
<223> OTHER INFORMATION: Primer

<400> SEQUENCE: 60
ggacaacatc gcgcctcctt cta                                              23

<210> SEQ ID NO 61
<211> LENGTH: 23
<212> TYPE: DNA
<213> ORGANISM: Artificial Sequence
<220> FEATURE:
<223> OTHER INFORMATION: Primer

<400> SEQUENCE: 61
tagaaggagg cgcgatgttg tcc                                              23

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
ggacaacatc tcacctcctt cta                                              23

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
tagaaggagg tgagatgttg tcc                                              23

<210> SEQ ID NO 64
<211> LENGTH: 23
<212> TYPE: DNA
<213> ORGANISM: Artificial Sequence
<220> FEATURE:
<223> OTHER INFORMATION: Primer

<400> SEQUENCE: 64
ggacaacatc accctcctt cta                                               23

<210> SEQ ID NO 65
<211> LENGTH: 23
<212> TYPE: DNA
<213> ORGANISM: Artificial Sequence
<220> FEATURE:
<223> OTHER INFORMATION: Primer
```

```
<400> SEQUENCE: 65
tagaaggagg ggtgatgttg tcc                                    23
```